United States Patent
Ehrnsperger et al.

(10) Patent No.: US 6,811,842 B1
(45) Date of Patent: Nov. 2, 2004

(54) LIQUID TRANSPORT MEMBER FOR HIGH FLUX RATES BETWEEN TWO PORT REGIONS

(75) Inventors: Bruno Johannes Ehrnsperger, Frankfurt (DE); Mattias Schmidt, Idstein (DE); Karl Michael Schumann, Cincinnati, OH (US); Fred Naval Desai, Fairfield, OH (US); Gary Dean Lavon, Oberursel (DE); Gerald Alfred Young, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,187

(22) PCT Filed: Jun. 29, 1999

(86) PCT No.: PCT/US99/14654

§ 371 (c)(1),
(2), (4) Date: Dec. 20, 2000

(87) PCT Pub. No.: WO00/00143

PCT Pub. Date: Jan. 6, 2000

(51) Int. Cl.$^7$ .................. B01D 63/00; A61F 13/15
(52) U.S. Cl. .............. 428/34.1; 428/304.4; 428/310.5; 210/321.6; 604/385.101
(58) Field of Search ................. 428/34.1, 35.2, 428/35.6, 35.7, 36.1, 36.2, 36.5, 36.9, 36.91, 304.4, 310.5, 311.11, 311.51, 311.71, 312.2, 313.3, 316.6; 604/327, 358, 365, 366, 367, 369, 370, 372, 374, 378, 385.01, 385.101; 210/321.6

(56) References Cited

U.S. PATENT DOCUMENTS

| | | | |
|---|---|---|---|
| 4,220,152 A | * | 9/1980 | Dresback .............. 424/439 |
| 4,820,293 A | | 4/1989 | Kamme |
| 5,082,723 A | | 1/1992 | Gross et al. |
| 5,108,383 A | | 4/1992 | White |
| 5,387,207 A | | 2/1995 | Dyer et al. |
| 5,563,179 A | | 10/1996 | Stone et al. |
| 5,728,292 A | | 3/1998 | Hashimoto et al. |
| 5,733,581 A | | 3/1998 | Barboza et al. |
| 6,579,457 B1 | * | 6/2003 | Ehrnsperger et al. .... 210/321.6 |
| 6,673,057 B1 | * | 1/2004 | Ehrnsperger et al. . 604/385.101 |

FOREIGN PATENT DOCUMENTS

| | | |
|---|---|---|
| EP | 0 365 565 B1 | 5/1990 |
| EP | 0 439 890 A1 | 8/1991 |
| EP | 0 773 058 A1 | 5/1997 |
| EP | 0 780 148 A1 | 6/1997 |
| EP | 0 810 078 A1 | 12/1997 |
| WO | WO 95/28139 A1 | 10/1995 |
| WO | WO 97/35656 A1 | 10/1997 |
| WO | WO 97/47375 A1 | 12/1997 |

* cited by examiner

*Primary Examiner*—Harold Pyon
*Assistant Examiner*—Alicia Chevalier
(74) *Attorney, Agent, or Firm*—Matthew P. Fitzpatrick; Ian S. Robinson; Ken K. Patel

(57) ABSTRACT

The present invention is a Liquid transport member with significantly improved liquid handling capability, which has at least one bulk region and a wall region that completely circumscribes said bulk region, and which comprises a port region, whereby the bulk region has an average fluid permeability $k_b$, which is higher than the average fluid permeability $k_p$ of the port regions.

48 Claims, 23 Drawing Sheets

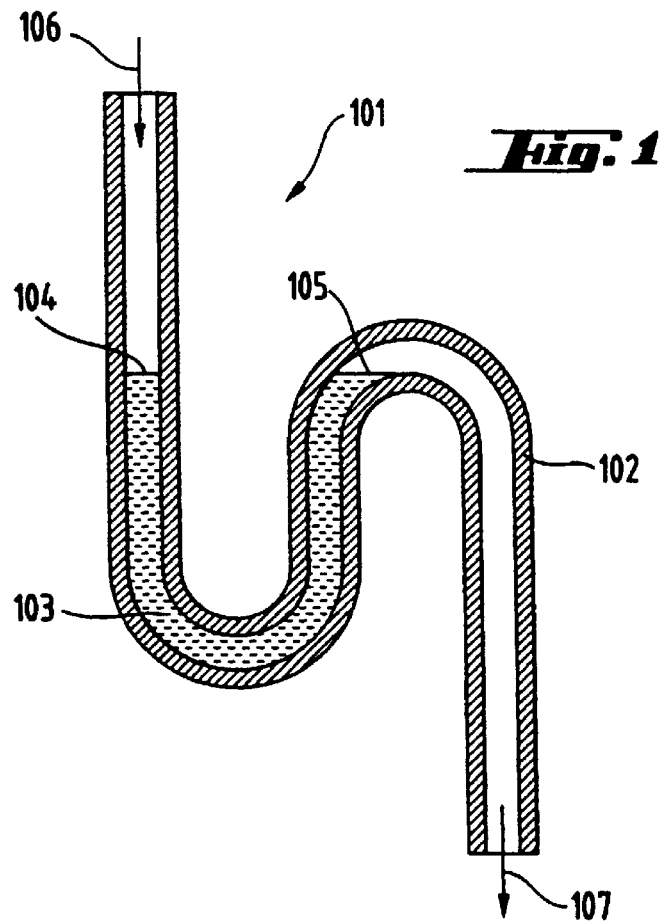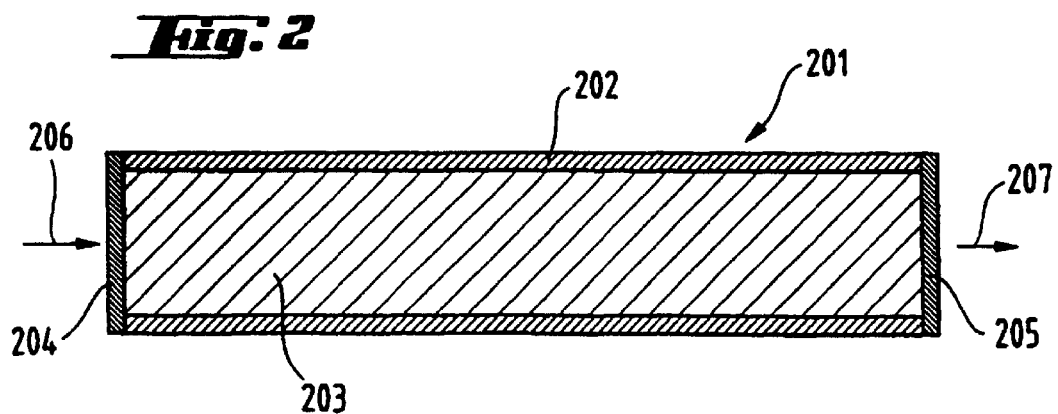

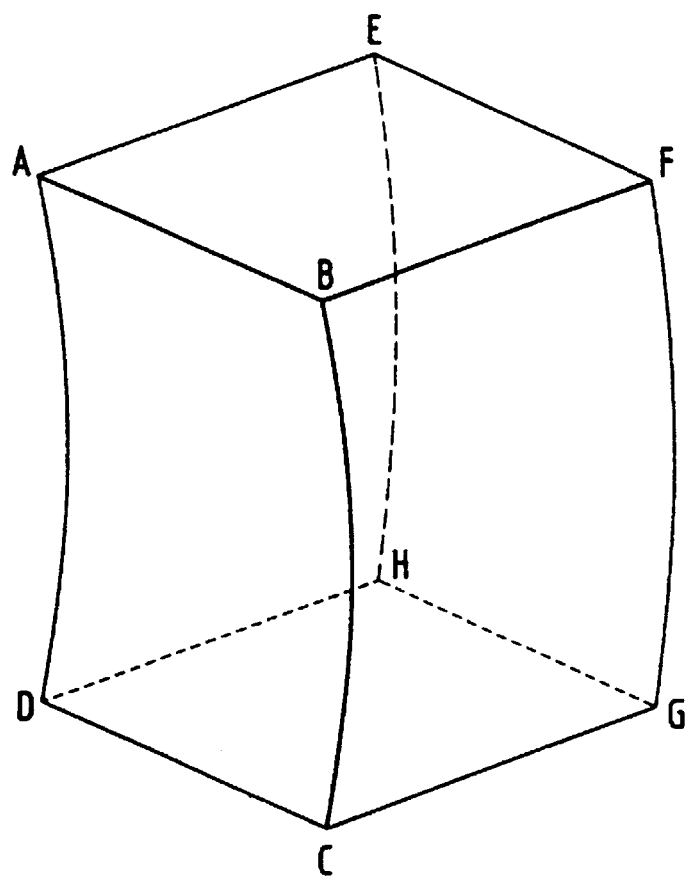
Fig. 5A
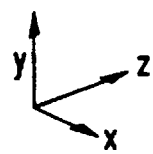

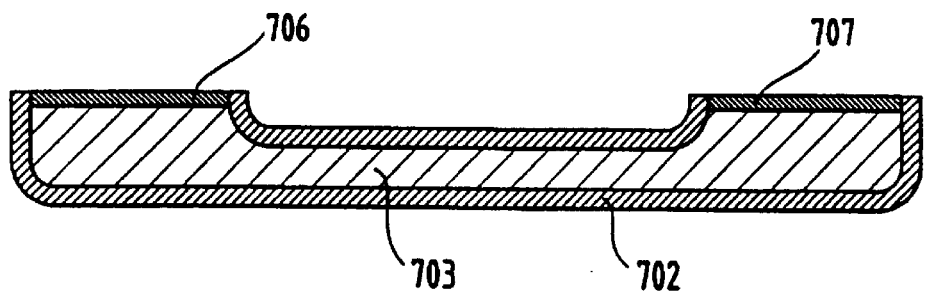
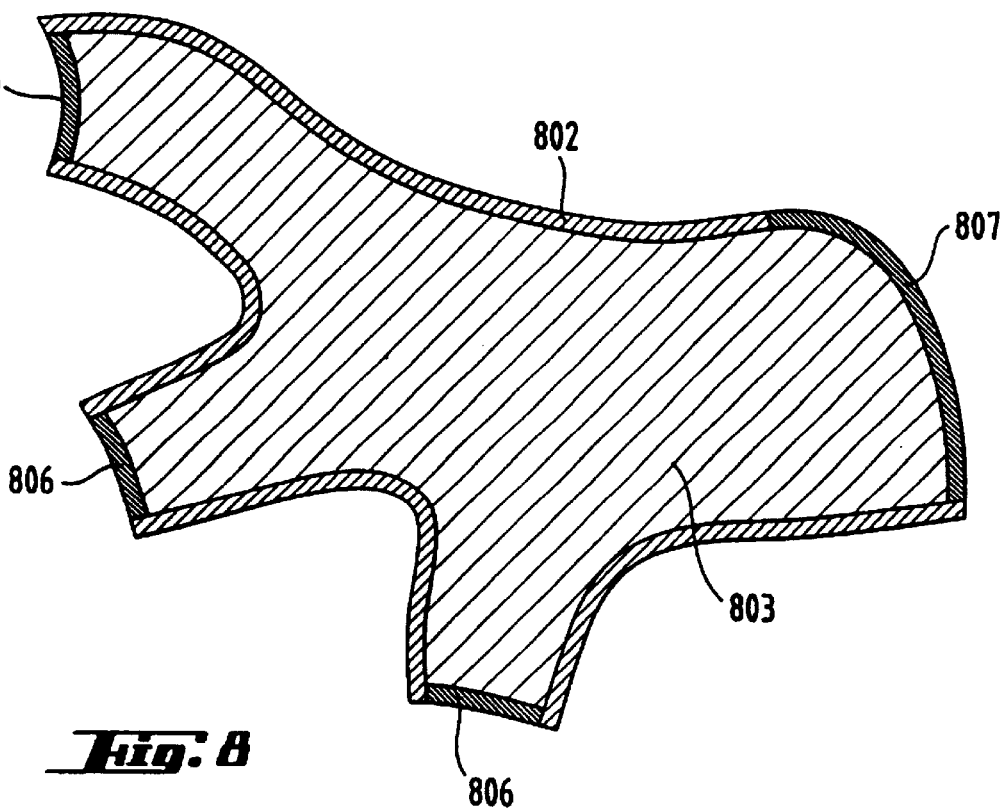

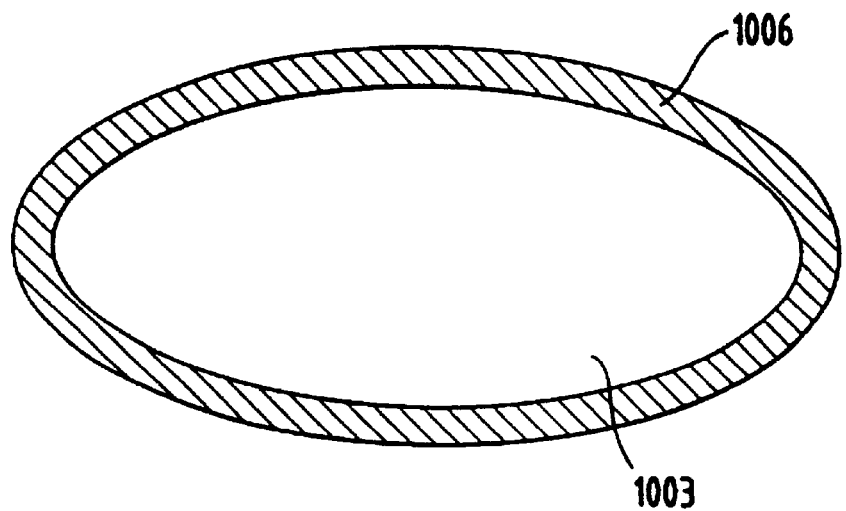

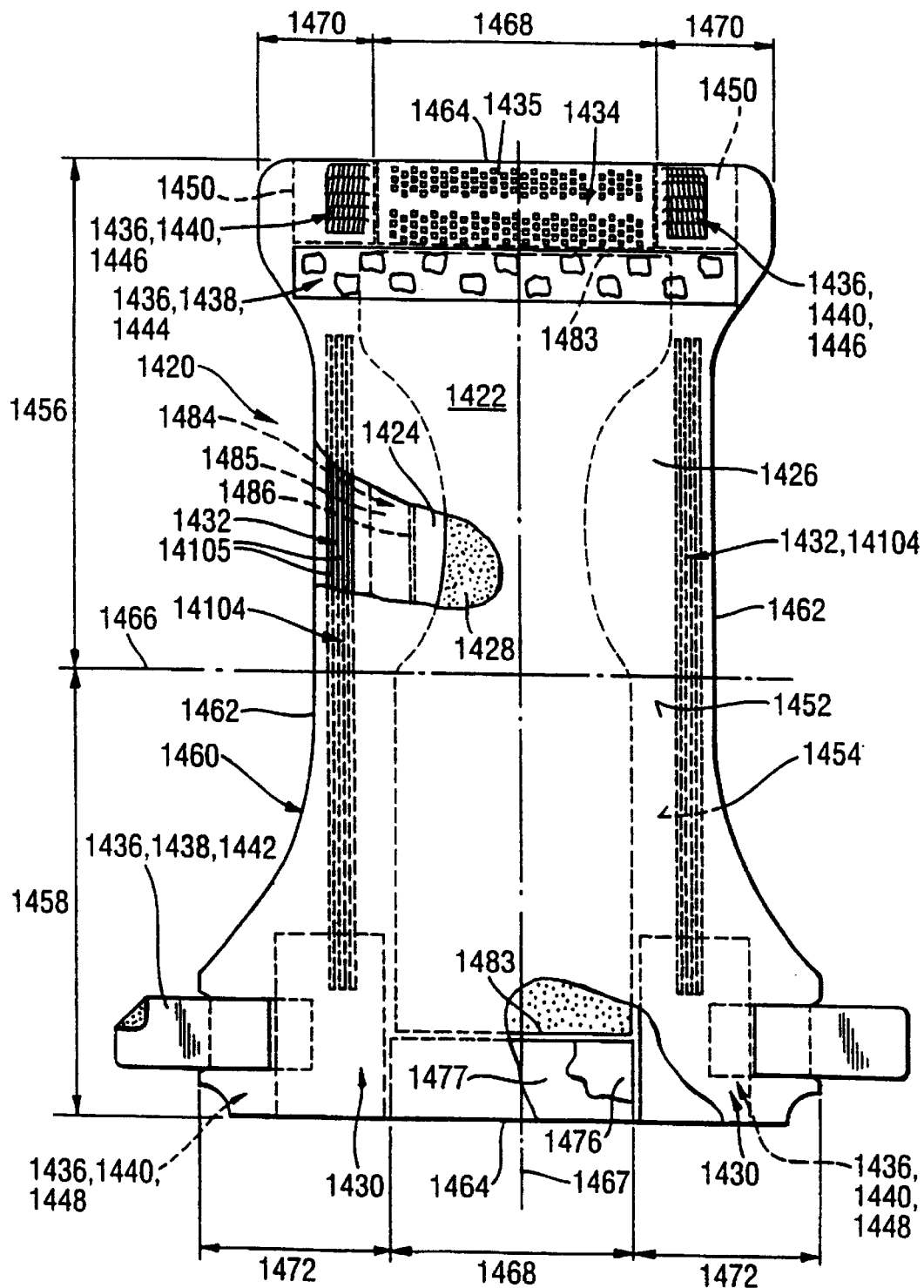

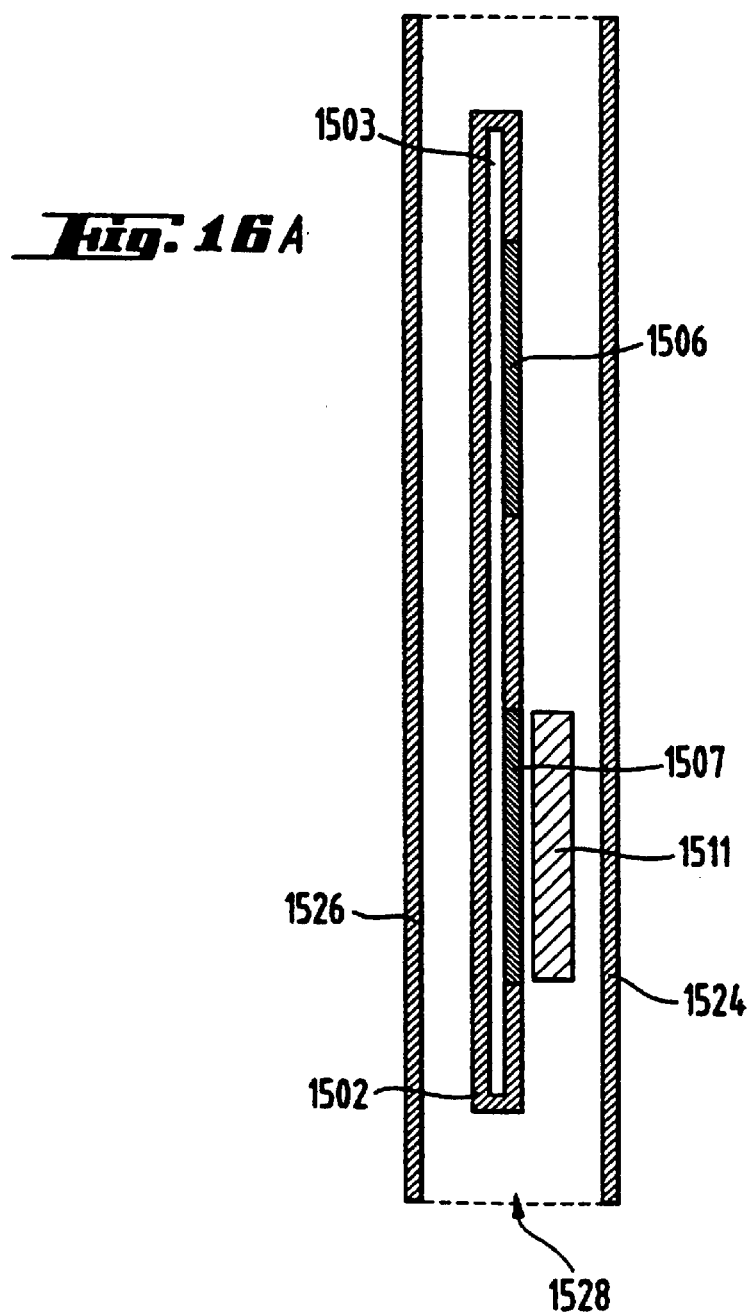

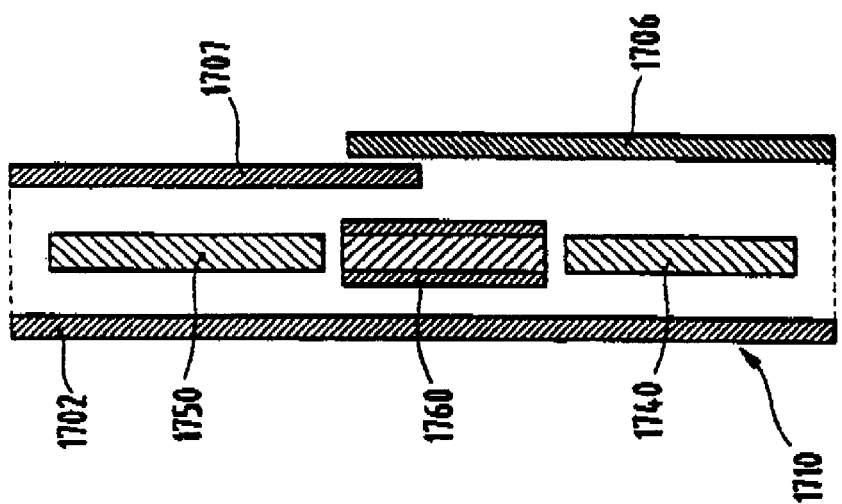
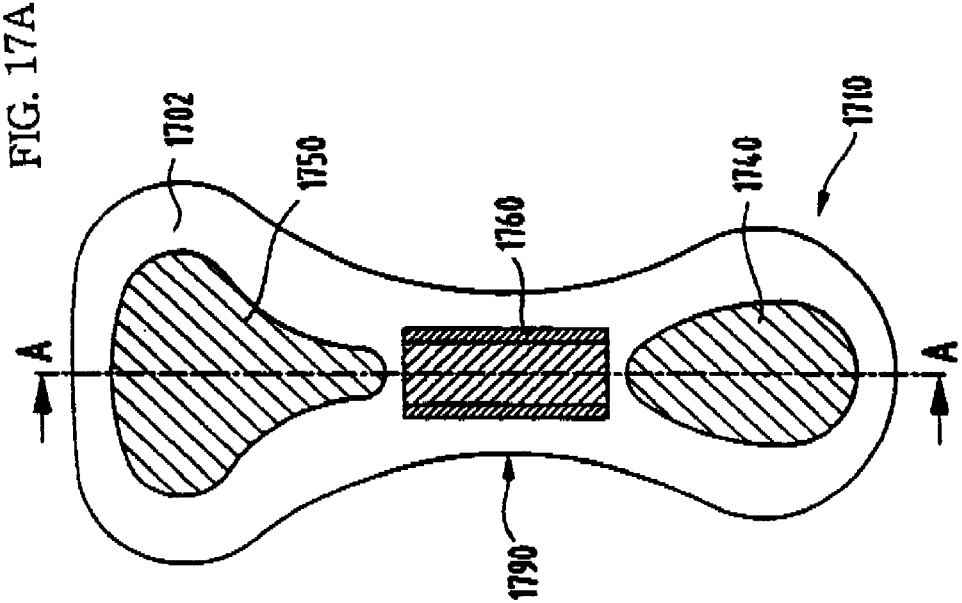

LIQUID TRANSPORT MEMBER FOR HIGH FLUX RATES BETWEEN TWO PORT REGIONS

FIELD OF THE INVENTION

The present invention relates to liquid transport members useful for a wide range of applications requiring high flow and/or flux rate, wherein the liquid can be transported through such a member, and/or be transported into or out of such a member. Such members are suitable for many applications, as—without being limited to—disposable hygiene articles, water irrigation systems, spill absorbers, oil/water separators and the like. The invention further relates to liquid transport systems comprising said liquid transport members and articles utilizing these.

BACKGROUND

The need to transport liquids from one location to another is a well known problem.

Generally, the transport will happen from a liquid source through a liquid transport member to a liquid sink, for example from a reservoir through a pipe to another reservoir. There can be differences in potential energy between the reservoirs (such as hydrostatic height) and there can be frictional energy losses within the transport system, such as within the transport member, in particular if the transport member is of significant length relative to the diameter thereof.

For this general problem of liquid transport, there exist many approaches to create a pressure differential to overcome such energy differences or losses so as to cause the liquids to flow. A widely used principle is the use of mechanical energy such as pumps. Often however, it will be desirable to overcome such energy losses or differences without the use of pumps, such as by exploiting hydrostatic height differential (gravity driven flow), or via capillary effects (often referred to as wicking).

In many of such applications, it is desirable to transport the liquids at high rates, i.e. high flow rate (volume per time), or high flux rate (volume per time per unit area of cross-section).

Examples for applications of liquid transport elements or members can be found in fields like water irrigation such as described in EP-A-0.439.890, or in the hygiene field, such as for absorbent articles like baby diapers both of the pull-on type or with fastening elements like tapes, training pants, adult incontinence products, feminine protection devices.

A well known and widely used execution of such liquid transport members are capillary flow members, such as fibrous materials like blotting paper, wherein the liquid can wick against the gravity. Typically such materials are limited in their flow and/or flux rates, especially when wicking height is added as an additional requirement. An improvement particularly towards high flux rates at wicking heights particularly useful for example for application in absorbent articles has been described in EP-A-0.810.078.

Other capillary flow members can be non-fibrous, but yet porous structures, such as open celled foams. In particular for handling aqueous liquid, hydrophilic polymeric foams have been described, and especially hydrophilic open celled foams made by the so called High Internal Phase Emulsion (HIPE) polymerization process have been described in U.S. Pat. No. 5,563,179 and U.S. Pat. No. 5,387,207.

However, in spite of various improvements made on such executions, there is still a need to get significant increase in the liquid transport properties of liquid transport members.

In particular, it would be desired to obtain liquid transport members, that can transport liquid against gravity at very high flux rates.

In situations wherein the liquid is not homogeneous in composition (such as a solution of salt in water), or in its phases (such as a liquid/solid suspension), it can be desired to transport the liquid in its totality, or only parts thereof. Many approaches are well known for their selective transport mechanism, such as in the filter technology.

For example, filtration technology exploits the higher and lower permeability of a member for one material or phase compared to another material or phase. There is abundance of art in this field, in particular also relating to the so called micro-, ultra-, or nano-filtration. Some of the more recent publications are:

U.S. Pat. No. 5,733,581 relating to melt-blown fibrous filter;

U.S. Pat. No. 5,728,292 relates to non-woven fuel filter;

WO-A-97/47375 relating to membrane filter systems;

WO-A-97/35656 relating to membrane filter systems;

EP-A-0.780.148 relating to monolithic membrane structures;

EP-A-0.773.058 relating to oleophilic filter structures.

Such membranes are also disclosed to be used in absorbent systems.

In U.S. Pat. No. 4,820,293 (Kamme) absorbent bodies are disclosed, for being used in compresses, or bandages, having a fluid absorbent substance enclosed in a jacket made of one essentially homogeneous material. Fluid can enter the body through any part of the jacket, and no means is foreseen for liquid to leave the body.

Therein, fluid absorbent materials can have osmotic effects, or can be gel-forming absorbent substances enclosed in semipermeable membranes, such as cellulose, regenerated cellulose, cellulose nitrate, cellulose acetate, cellulose acetate butyrate, polycarbonate, polyamide, fiberglass, polysulfone, of polytetrafluoroethylene, having pore sizes of between 0.001 $\mu$m and 20 $\mu$m, preferably between 0.005 $\mu$m and 8 $\mu$m, especially about 0.01 $\mu$m.

In such a system, the permeability of the membrane is intended to be such that the absorbed liquid can penetrate, but such that the absorbent material is retained.

It is therefore desired to use membranes having a high permeability k and a low thickness d, so as to achieve a high liquid conductivity k/d of the layer, as being described herein after.

This can be achieved by incorporation of promoters with higher molecular weight (e.g. polyvinyl pyrrolidone with a molecular weight of 40,000), such that the membranes can have larger pores leading to larger membrane permeability k. The maximum pore size stated therein to be useful for this application is less than 0.5 $\mu$m, with pore sizes of about 0.01 $\mu$m or less being preferred. The exemplified materials allow the calculation of k/d values in the range of 3 to $7*10^{-14}$ m.

As this system is quite slow, the absorbent body can further comprise for rapid discharge of fluids a liquid acquisition means, such as conventional acquisition means to provide interim storage of the fluids before these are slowly absorbed.

A further application of membranes in absorbent packets is disclosed in U.S. Pat. No. 5,082,723, EP-A-0.365.565, or U.S. Pat. No. 5,108,383 (White; Allied-Signal).

Therein, an osmotic promoter, namely a high-ionic strength material such as NaCl, or other high osmolality material like glucose or sucrose is placed inside a membrane such as made from cellulosic films. As with the above disclosure, fluid can enter the body through any part of the jacket, and no means is foreseen for liquid to leave the body. When these packets are contacted by aqueous liquids, such as urine, the promoter materials provide an osmotic driving force to pull the liquid through the membranes. The membranes are characterized by having a low permeability for the promoter, and the packets achieve typical rates of 0.001 ml/cm$^2$/min. When calculating membrane conductivity k/d values for the membranes disclosed therein, values of about 1 to $2*10^{-15}$ m result. An essential property of membranes useful for such applications is their "salt retention", i.e. whilst the membranes should be readily penetrable by the liquid, they must retain a substantial amount of the promoter material within the packets. This salt retention requirements provides a limitation in pore size which will limit liquid flux.

U.S. Pat. No. 5,082,723 (Gross et al.) discloses an osmotic material like NaCl which is enclosed by superabsorbent material, such as a copolymer of acrylic acid and sodium acrylate, thereby aiming at improving absorbency, such as enhanced absorptive capacity on a "gram per gram" basis and absorption rate.

Overall, such fluid handling members are used for improved absorbency of liquids, but have only very limited fluid transport capability.

Thus, there remains still a need to improve the liquid transport properties, in particular to increase the flow and/or flux rates in liquid transport systems.

Hence it is an object of the present invention to provide a liquid transport member composed of at least two regions exhibiting a difference in permeability.

It is a further object to provide liquid transport members exhibiting improved liquid transport, as expressed in significantly increased liquid flow rates, and especially liquid flux rates, i.e. the amount of liquid flowing in a time unit through a certain cross-section of the liquid transport member.

It is a further object of the present invention to allow such liquid transport against gravity.

It is a further object of the present invention to provide such an improved liquid transport member for fluids with a wide range of physical properties, such as for aqueous (hydrophilic) or non-aqueous, oily or lipophilic liquids.

It is a further object of this invention to provide liquid transport systems, comprising in addition to the liquid transport member a liquid sink and/or liquid source.

It is an even further object of the present invention to provide any of the above objects for being used in absorbent structures, such as can be useful in hygienic absorbent products, such as baby diapers, adult incontinence products, feminine protection products.

It is an even further object of the present invention to provide any of the above objects for use as water irrigation systems, spill absorber, oil absorber, water/oil separators.

SUMMARY OF THE INVENTION

The present invention is a liquid transport member which comprises at least one bulk region and a wall region that completely circumscribes the bulk region, and whereby the wall region further comprises at least one inlet port region and at least one outlet port region, whereby the bulk region has an average fluid permeability $k_b$ which is higher than the average fluid permeability $k_p$ of the port regions. Preferably, the bulk region has a fluid permeability of at least $10^{-11}$ m$^2$, or of at least $10^{-8}$ m$^2$, more preferably of at least $10^{-7}$ m$^2$, most preferably of at least $10^{-5}$ m$^2$, and the port regions bulk region have a fluid permeability of at least $10^{-11}$ m$^2$, preferably of at least $10^{-8}$ m$^2$, more preferably of at least $10^{-7}$ m$^2$, most preferably of at least $10^{-5}$ m$^2$ The liquid transport member can have port regions having a ratio of fluid permeability to thickness in the direction of fluid transport, $k_p/d_p$ of at least $3*10^{-15}$ m, preferably of at least $7*10^{-14}$ m, more preferably of at least $3*10^{-10}$ m, even more preferably of at least $8*10^{-8}$ m, or even of at least $5*10^{-7}$ m, and most preferably of at least $10^{-5}$ m.

In preferred embodiments the present invention is a liquid transport member wherein a first region of the member comprises materials which are in contact with an additional element, which extends into a neighbouring second region without extending the functionality of the first region. A particular embodiment comprises an additional element extending from the wall region into the outer region, preferably having a capillary pressure for absorbing the liquid that is lower than the bubble point pressure of said member. This additional element may comprise a softness layer.

In a further preferred embodiment, the ratio of permeability of the bulk region and the permeability of the port region is at least 10, preferably at least 100, more preferably at least 1000, and even more preferably at least 100 000.

In yet a further preferred embodiment, the member has a bubble point pressure when measured with water as test liquid having a surface tension of 72 mN/m of at least 1 kPa, preferably of at least 2 ka, more preferably at least 4.5 ka, even more preferably 8.0 kPa most preferably 50 kPa.

In a further preferred embodiment, the port region has a bubble point pressure when measured with water as test liquid having a surface tension of 72 mN/m of at least 1 kPa, preferably of at least 2 kPa, more preferably at least 4.5 kPa, even more preferably 8.0 kPa, most preferably 50 kpa, or when measured with an aqueous test solution having a surface tension of 33 mN/m of at least 0.67 kPa, preferably at least 1.3 kPa, more preferably at least 3.0 kPa, even more preferably at least 5.3 kPa, most preferably at least 33 kPa.

In a particular embodiment, the liquid transport member according to the present invention looses at least 3% of the initial weight liquid, when submitted to the Closed System test, as described hereinafter.

In a further preferred embodiment, the bulk region has a larger average pore size than said port regions, such that the ratio of average pore size of the bulk region and the average pore size of the port region is preferably at least 10, more preferably at least 50, even more preferably at least 100, or even at least 500, and most preferably at least 1000.

In another preferred embodiment, the bulk region has an average pore size of at least 200 μm, preferably at least 500 μm, more preferably of at least 1000 μm, and most preferably of at least 5000 μm.

In another preferred embodiment, the bulk region has a porosity of at least 50%, preferably at least 80%, more preferably at least 90%, even more preferably of at least 98%, and most preferably of at least 99%.

In another preferred embodiment, the port region has a porosity of at least 10%, more preferably at least 20%, even more preferably of at least 30%, and most preferably of at least 50%.

In another preferred embodiment, the port regions have an average pore size of no more than 100 μm, preferably no more than 50 μm, more preferably of no more than 10 μm, and most preferably of no more than 50 μm. It is also preferred, that the port regions have a pore size of at least 1 μm, more preferably at least 3 μm.

In another preferred embodiment, the port regions have an average thickness of no more than 100 μm, preferably no more than 50 μm, more preferably of no more than 10 μm, and most preferably of no more than 5 μm.

In another preferred embodiment, the bulk regions and the wall regions have a volume ratio (bulk to wall region) of at least 10, preferably at least 100, more preferably at least 1000, and even more preferably at least 10000.

In another specific embodiment in particular for transporting aqueous liquids, the port region is hydrophilic, and preferably is made of materials having a receding contact angle for the liquid to be transported less than 70 degrees, preferably less than 50 degrees, more preferably less than 20 degrees, and even more preferably less than 10 degrees. Preferably, the port regions do not substantially decrease the liquid surface tension of the liquid that is to be transported.

In another specific embodiment in particular for transporting oily liquids, the port region is oleophilic, and preferably is made of materials having a receding contact angle for the liquid to be transported less than 70 degrees, preferably less than 50 degrees, more preferably less than 20 degrees, and even more preferably less than 10 degrees.

In another specific embodiment, the liquid transport member can be expandable upon contact with, and collapsible upon removal of liquid.

In other specific embodiments, the member can have a sheet-like, or cylindrical shape, optionally the cross-section of the member along the direction of liquid transport is not constant. Further, port regions can have a larger area than the average cross-section of the member along the direction of liquid transport, preferably port regions have an area that is larger than the average cross-section of the member along the direction of liquid transport by at least a factor of 2, preferably a factor of 10, most preferably a factor of 100.

In another specific embodiment, the member comprises bulk or port material which can expand and recollapse during liquid transport, and preferably has a volume expansion factor of at least 5 between the original state and when being activated, i.e. fully immersed in liquid.

In another specific embodiment, the bulk region comprises a material selected from the groups of fibers, particulates, foams, spirals, films, corrugated sheets, or tubes.

In another specific embodiment, the wall region comprises a material selected from the groups of fibers, particulates, foams, spirals, films, corrugated sheets, tubes, woven webs, woven fiber meshes, apertured films, or monolithic films.

In another specific embodiment, the bulk or wall region may an open cell reticulated foam, preferably a foam selected from the group of cellulose sponge, polyurethane foam, HIPE foams.

In another specific embodiment, the liquid transport member comprises fibers, which are made of polyolefins, polyesters, polyamids, polyethers, polyacrylics, polyurethanes, metal, glass, cellulose, cellulose derivatives.

In yet another embodiment, the liquid transport member is made by a porous bulk region that is wrapped by a separate wall region. In a special embodiment, the member may comprise water soluble materials, for example to increase permeability or pore size upon contact with the liquid in the bulk or port regions.

In further specific embodiments, the liquid transport member is initially wetted by or essentially filled with liquid, or is under vacuum.

A liquid transport member can be particularly suitable to transport of water-based liquids, of viscoelastic liquids, or for bodily exudates such as urine, blood, menses, feces or sweat.

A liquid transport member can also be suitable for transport of oil, grease, or other non-water based liquids, and it can be particularly suitable for selective transport of oil or grease, but not water based liquids. In a special application, the port regions may be hydrophobic.

In yet another specific embodiment, the properties or parameter of any of the regions of the member or of the member itself need not to be maintained during the transport of the member from its production to the intended use, but these are established just prior to or at the time of liquid handling. This may be achieved by having an activation of the member, such as contact with the transported liquid, pH, temperature, enzyme, chemical reaction, salt concentration or mechanical activation. The port region may further comprise a stimulus activatable membrane material, such as a membrane changing its hydrophilicity upon a temperature change.

Another aspect of the present invention concerns the combination of a liquid transport member with a source of liquid and/or the sink of liquid, with at least one of these being positioned outside of the member.

In a specific embodiment, a liquid transport system, comprising a liquid transport member according to the present invention, wherein the system has an absorption capacity of at least 5 g/g, preferably at least 10 g/g, more preferably at least 20 g/g, on the weight basis of the sink material when measured in the Demand Absorbency Test.

In yet another specific embodiment, the liquid transport system contains a sink material that has an absorption capacity of at least 10 g/g, preferably at least 20 g/g and more preferably at least 50 g/g on the basis of the weight of the sink material, when submitted to the Teabag Centrifuge Capacity Test. In a further embodiment, the sink material that has an absorbent capacity of at least 5 g/g, preferably at least 10 g/g, more preferably of at least 50 g/g when measured in the Capillary Suction Test at a pressure up to the bubble point pressure of the port region, and which has an absorbent capacity of less than 5 g/g, preferably less than 2 g/g, more preferably less than 1 g/g, and most preferably of less than 0.2 g/g when measured in the Capillary Suction Test at a pressure exceeding the bubble point pressure of the region.

In certain specific embodiments, the liquid transport member also contains superabsorbent materials or foam made according to the High Internal Phase Emulsion polymerization.

An even further aspect of the present invention relates to an article comprising a liquid transport member or a liquid transport system according to the present invention, such as an absorbent article or a disposable absorbent article comprising a liquid transport member. An application, which can particularly benefit from using members according to the present invention is a disposable absorbent hygiene article, such a baby or adult incontinence diaper, a feminine protection pad, a pantiliner, a training pant. Other suitable applications can be found for a bandage, or other health care absorbent systems. In another aspect, the article can be a water transport system or member, optionally combining transport functionality with filtration functionality, e.g. by purifying water which is transported. Also, the member can be useful in cleaning operation, so as by removing liquids or as by releasing fluids in a controlled manner. A liquid transport member according to the present invention can also be a oil or grease absorber, or can be used for separation of oily and aqueous liquids.

Yet another aspect of the present invention relates to the method of making a liquid transport member, wherein the method comprises the steps of
- a) providing a bulk or inner material;
- b) providing a wall material comprising a port region;
- c) completely enclosing said bulk region material by said wall material;
- d) providing a transport enablement means selected from
  - d1) vacuum;
  - d2) liquid filling;
  - d3) expandable elastics/springs.

Optionally, the method can comprise the step of
- e) applying activation means of
  - e1) liquid dissolving port region;
  - e2) liquid dissolving expandable elastication/springs.
  - e3) removable release element;
  - e4) removable sealing packaging.

In another embodiment, the method may comprise the steps of
- a) wrapping a highly porous bulk material with a separate wall material that contains at least one permeable port region,
- b) completely sealing the wall region,
- and c) evacuating the member essentially of air.

In an further specific embodiment, the method further comprises the step wetting the member, or partially or essentially completely filling the member with liquid.

In an further specific embodiment, the method additionally comprises the step of sealing the member with a liquid dissolvable layer at least in the port regions.

BRIEF DESCRIPTION OF THE DRAWINGS

FIG. 1: Schematic diagram of conventional open siphon.

FIG. 2: Schematic diagram of a liquid transport member according to the present invention.

FIG. 7: Schematic diagram of an embodiment of liquid transport member according to the present invention.

FIG. 8: Schematic diagram of an embodiment of liquid transport member according to the present invention.

FIG. 10: Schematic diagram of an embodiment of liquid transport member according to the present invention.

FIG. 14: Schematic diagram of an absorbent article.

FIGS. 17A, B to 18A, B, C, D: Specific embodiments of liquid transport member.

DETAILED DESCRIPTION OF THE INVENTION

General Definitions

Figure 3A:
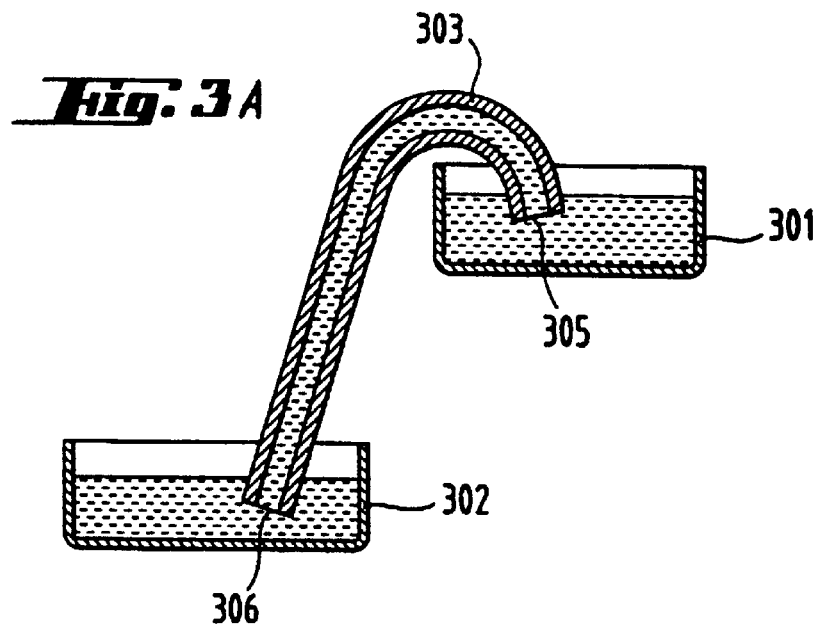
FIGS. 3 A, B: Conventional Siphon system, and liquid transport member according to the present invention.
Figure 3B:
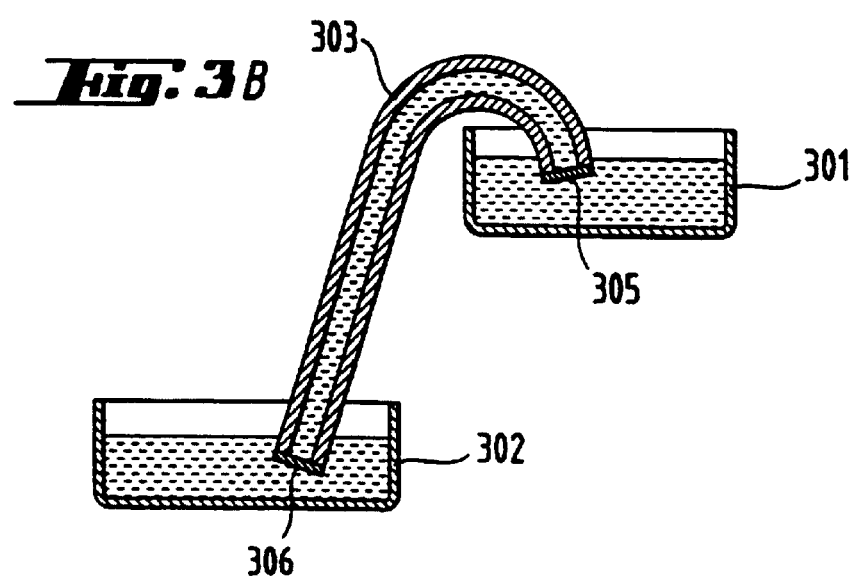

As used herein, a "liquid transport member" refers to a material or a composite of materials, which is able to transport liquids. Such a member contains at least two regions, an "inner" region, for which the term "bulk" region can be used interchangeably, and a wall region comprising at least one "port" region. The terms "inner" and "outer" refer to the relative positioning of the regions, namely meaning, that the outer region generally circumscribes the inner region, such as a wall region circumscribing a bulk region.

As used herein, the term "Z-dimension" refers to the dimension orthogonal to the length and width of the liquid transport member or article. The Z-dimension usually corresponds to the thickness of the liquid transport member or the article. As used herein, the term "X-Y dimension" refers to the plane orthogonal to the thickness of the member, or article. The X-Y dimension usually corresponds to the length and width, respectively, of the liquid transport member, or article. The term layer also can apply to a member, which—when describing it in spherical or cylindrical co-ordinates—extends in radial direction much less than in the other ones. For example, the skin of a balloon would be considered a layer in this context, whereby the skin would define the wall region, and the air filled center part the inner region.

As use herein, the term "layer" refers to a region whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, it should also be understood that the term "upper" refers to members, articles such as layers, that are positioned upwardly (i.e. oriented against the gravity vector) during the intended use. For example, for a liquid transport member intended to transport liquid from a flowerd reservoir to an "upper" one, this is meant to be transport against gravity.

All percentages, ratios and proportions used herein are calculated by weight unless otherwise specified.

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes, but is not limited to, urine, menses and vaginal discharges, sweat and feces.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an nvironmentally compatible manner).

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

A member or material can be described by having a certain structure, such as a porosity, which is defined by the ratio of the volume of the solid matter of the member or material to the total volume of the member or material. For example, for a fibrous structure made of polypropylene fibers, the porosity can be calculated from the specific weight (density) of the structure, the caliper and the specific weight (density) of the polypropylene fiber:

$$V_{void}/V_{total} = (1-\rho_{bulk}/\rho_{material})$$

The term "activatable" refers to the situation, where a certain ability is restricted by a certain means, such that upon release of this means a reaction such as a mechanical response happens. For example, if a spring is held together by a clamp (and thus would be activatable), releasing of the clamp results in activating the expansion of the spring. For such springs or other members, materials or systems having an elastic behavior, the expansion can be defined by the elastic modulus, as well known in the art.

Basic Principles and Definitions

Liquid transport mechanism in conventional capillary flow systems.

Without wishing to be bound by any of the following explanations, the basic functioning mechanism of the present invention can be best explained by comparing it to conventional materials.

In materials, for which the liquid transport is based on capillary pressure as the driving force, the liquid is pulled into the pores that were initially dry, by the interaction of the liquid with the surface of the pores. Filling the pores with liquid replaces the air in these pores. If such a material is at least partially saturated and if further a hydrostatic, capillary, or osmotic suction force is applied to at least one region of that material, liquid will be desorbed from this material if the suction pressure is larger than the capillary pressure that retains the liquid in the pores of the materials (refer e.g., to "Dynamics of fluids in porous media" by J. Bear, Haifa, publ. Dover Publications Inc., NY, 1988).

Upon desorption, air will enter the pores of such conventional capillary flow materials. If additional liquid is available, this liquid can be pulled into the pores again by capillary pressure. If therefore a conventional capillary flow material is connected at one end to a liquid source (e.g., a reservoir) and on the other end to a liquid sink (e.g., a hydrostatic suction), the liquid transport through this material is based on the absorption/desorption and re-absorption cycle of the individual pores with the capillary force at the liquid/air-interface providing the internal driving force for the liquid through the material.

This is in contrast to the transport mechanism for liquids through transport members according to the present invention.

Siphon Analogy

A simplifying explanation for the functioning of the present invention can start with comparing it to a siphon (refer to FIG. 1), well known from drainage systems as a tubing in form of a laying "S" (101). The principle thereof is, that—once the tubing (102) is filled with liquid (103)—upon receipt of further liquid (as indicated by 106)—entering the siphon at one end, almost immediately liquid leaves the siphon at the other end (as indicated by 107), as—because the siphon is being filled with incompressible liquid—the entering liquid is immediately displacing liquid in the siphon forcing the liquid at the other end to exit the siphon, if there is a pressure difference for the liquid between the point of entry and the point of exit of said siphon. In such a siphon, liquid is entering and leaving the system through an open surface inlet and outlet "port regions" (104 and 105 respectively).

The driving pressure to move liquid along the siphon can be obtained via a variety of mechanisms. For example, if the inlet is at a higher position than the outlet, gravity will generate a hydrostatic pressure difference generating liquid flow through the system.

Alternatively, if the outlet port is higher than the inlet port, and the liquid has to be transported against gravity, the liquid will flow through this siphon only if an external pressure difference larger than hydrostatic pressure difference is applied. For example, a pump could generate enough suction or pressure to move liquid through this siphon. Thus, liquid flow through a siphon or pipe is caused by an overall pressure difference between its inlet and outlet port region. This can be described by well known models, such as expressed in the Bernoulli equation.

The analogy of the present invention to this principle is schematically depicted in FIG. 2 as one specific embodiment. Therein, the liquid transport member (201) does not need to be s-shaped, but can be a straight tube (202). The liquid transport member can be filled with liquid (203), if the inlet and outlet of the transport member are covered by inlet port materials (204) and outlet port materials (205). Upon receipt of additional liquid (indicated by 206) which readily penetrates through the inlet port material (204), liquid (207) will immediately leave the member through the outlet region (205), via the outlet port material.

Thus, a key difference in principle is, that the inlet and/or outlet ports are not open surfaces, but have special permeability requirements as explained in more detail hereinafter, which prevent air or gas from penetrating into the transport member, thus the transport member remains filled with liquid.

A liquid transport member according to the present invention can be combined with one or more liquid source(s) and/or sink(s) to form a liquid transport system. Such liquid sources or sinks can be attached to the transport member such as at inlet and/or outlet regions or the sink or the source can be integral with the member. A liquid sink can be—for example—integral with the transport member, when the transport member can expand its volume thereby receiving the transported liquid.

A further simplifying analogy to a siphon system in comparison to a Liquid Transport System can be seen in FIGS. 3A (siphon) and 3B (present invention). When connecting a liquid (source) reservoir (301) with a lower (in the direction of gravity) liquid (sink) reservoir (302) by a conventional tube or pipe with open ends (303) in the shape of an inverted "U" (or "J"), liquid can flow from the upper to the lower reservoir only if the tube is kept full with liquid by having the upper end immersed in liquid. If air can enter the pipe such as by removing the upper end (305) from the liquid, the transport will be interrupted, and the tube must be refilled to be functional again.

A liquid transport member according to the present invention would look very similar in an analog arrangement, except for the ends of the transport member, inlet (305) and outlet port (306), comprising inlet and outlet port materials with special permeability requirements as explained in more detail hereinafter instead of open areas. The inlet and outlet materials prevent air or gas from penetrating into the transport member, and thereby maintain the liquid transport capability even if the inlet is not immersed into the liquid source reservoir. If the transport member is not immersed into the liquid source reservoir, liquid transport will obviously stop, but can commence immediately upon re-immersion.

In broader terms, the present invention is concerned with liquid transport, which is based upon direct suction rather than on capillarity. Therein, the liquid is transported through a region through which substantially no air (or other gas) should enter this member (or at least not in a significant amount). The driving force for liquid flowing through such a member can be created by a liquid sink and liquid source in liquid communication with the member, either externally, or internally.

There is a multitude of embodiments of the present invention, some of which will be discussed in more detail hereinafter. For example, there can be members where the inlet and/or outlet port materials are distinctly different from the inner or bulk region, or there can be members with gradual change in properties, or there can be member executions wherein the source or sink is integral with the transport member, or wherein the entering liquid is different in type or properties from the liquid leaving the member.

Yet, all embodiments rely on the inlet or outlet port region having a different permeability for the transported liquid as well as for surrounding gas such as air than the inner/bulk region.

Within the context of the present invention, the term "liquid" refers to fluids consisting of a continuous liquid phase, optionally comprising a discontinuous phase such as an immiscible liquid phase, or solid or gases, so as to form suspension, emulsions or the like. The liquid can be homogeneous in composition, it can be a mixture of miscible liquids, it can be a solution of solids or gases in a liquid, and the like. Non-limiting examples for liquids that can be transported through members according to the present invention include water, pure or with additives or contaminants, salt solutions, urine, blood, menstrual fluids, fecal material over a wide ranged of consistencies and viscosities, oil, food grease, lotions, creams, and the like.

The term "transported liquid" or "transport liquid" refers to the liquid which is actually transported by the transport member, i.e., this can be the total of a homogeneous phase, or it can be the solvent in a phase comprising dissolved matter, e.g., the water of a aqueous salt solution, or it can be one phase in a multiphase liquid, or it can be that the total of the multicomponent or multiphase liquid. Henceforth, it will become readily apparent for which liquid the respective liquid properties, e.g., the surface energy, viscosity, density, etc., are relevant for various embodiments.

Whilst often the liquid entering the liquid transport member will be the same or of the same type as the liquid leaving the member or being stored therein, this does not necessarily need to be the case. For example when the liquid transport member is filled with an aqueous liquid, and—upon appropriate design—an oily liquid is received by the member, the aqueous phase may leave the member first. In this case, the aqueous phase could be considered "replaceable liquid".

Geometric Description of Transport Member Regions

Figure 4:
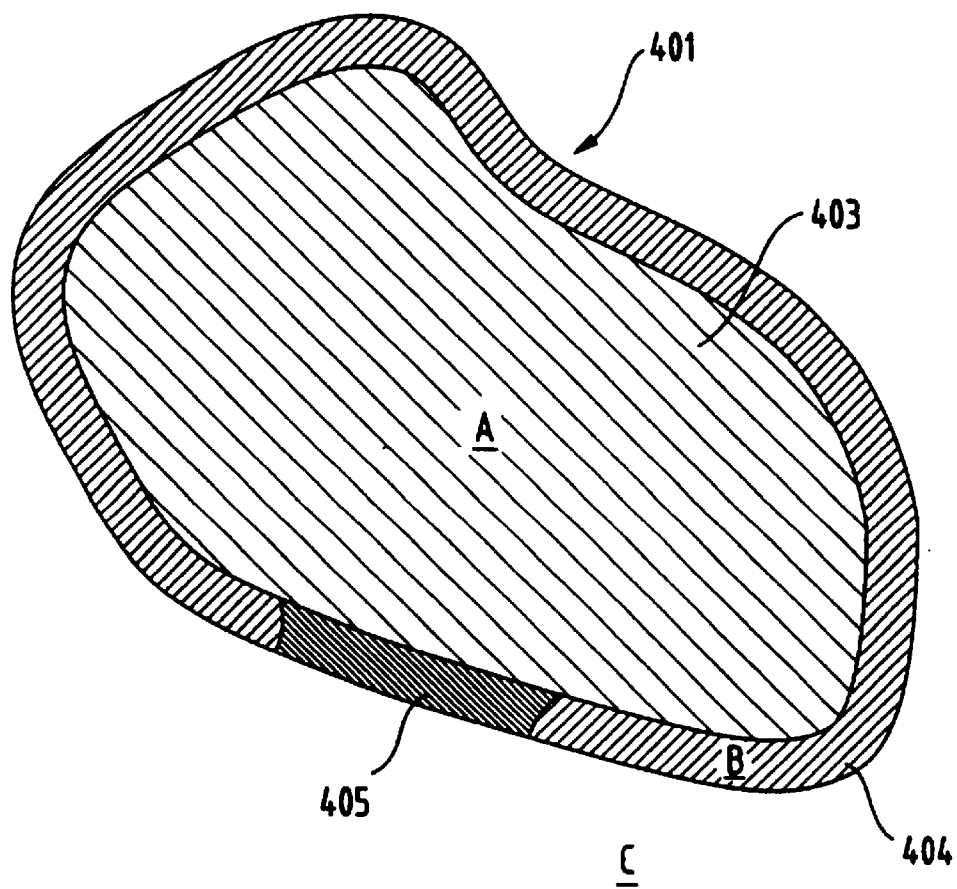
FIG. 4: Schematic cross-sectional view through a liquid transport member.

A liquid transport member in the sense of the present invention has to comprise at least two regions—a "bulk region" and a "wall region" comprising at least one liquid permeable "inlet port region" and one "outlet port region". The geometry, and especially the requirement of the wall region completely circumscribing the bulk region is defined by the following description (refer to FIG. 4), which considers a transport member at one point in time.

The bulk/inner region (403) and the wall region (404) are distinctively different and non-overlapping geometric regions with regard to each other as well as with regard to the outside region (i.e. "the rest of the universe"). Thus, any point can only belong to one of the regions.

The bulk region (403) is connected, i.e. for any two points A' and A" inside the bulk region (403), there is at least one continuous (curved or straight) line connecting the two points without leaving the bulk region (403).

For any point A inside the bulk region (403), all straight rodlike rays having a circular thickness of at least 2 mm diameter intersect the wall region (404). A straight ray has the geometrical meaning of a cylinder of infinite length in analogy to point A being a light source, and the rays being rays of light, however, these rays need to have a minimum geometrical "thickness" (as otherwise a line can pass through the pore opening of the port regions (405)). This geometrical thickness is set at 2 mm—which of course has to be considered in an approximation in the proximity of the point A (not having a three-dimensional extension to be matched with such a rodlike ray).

The wall region (404) completely circumscribes the bulk region (403). Thus, for any points A"—belonging to the bulk region (403)—and C—belonging to the outer region—any continuous curved rod (in analogy to a continuous curved line but having circular thickness of 2 mm diameter), intersects the wall region (404).

A port region (405) connects a bulk region (403) with the outside region, and there exists at least one continuous curved rod connecting any point A" from the bulk region with any point C from the "outside region", having a circular thickness of 2 mm, that intersects the port region (405).

The term "region" refers to three-dimensional regions, which can be of any shape. Often, but not necessarily, the thickness of the region can be thin, such that the region appears like a flat structure, such as a thin film. For example, membranes can be employed in a film form, which—depending on the porosity—can have a thickness of 100 $\mu$m or much less, thus being much smaller than the extension of the membrane perpendicular thereto (i.e. length and width dimension).

A wall region may be arranged around a bulk region for example in an overlapping arrangement, i.e. that certain parts of the wall region material contact each other and are connected to each other such as by sealing. Then, this sealing should have no openings which are sufficiently large to interrupt the functionality of the member, i.e. the sealing line could be considered to belong either to an (impermeable) wall region, or a wall region.

Whilst a region can be described by having at least one property to remain within certain limits so as to define the common functionality of the subregions of this region, other properties may well change within these sub-regions.

Within the current description, the term "regions" should be read to also encompass the term "region", i.e., if a member comprises certain "regions", the possibility of comprising only one such region should be included in this term, unless otherwise explicitly mentioned.

The "port" and "bulk/inner" regions can be readily distinguished from one another, such as a void space for one region and a membrane for another, or these regions can have a gradual transition with respect to certain relevant parameters as will be described hereinafter. Hence it is essential, that a transport member according to the present invention has at least one region satisfying the requirements for the "inner region" and one region satisfying the requirements for the "wall region", (which in fact can have an very small thickness relative to its extension in the other two dimensions, and thus appear more as a surface than a volume). The wall region comprises at least an inlet and an outlet region.

Thus, for a liquid transport member, the transport path can be defined as the path of a liquid entering a port region and the liquid exiting a port region, whereby the liquid transport path runs through the bulk region. The transport path can also be defined by the path of a liquid entering a port region and then entering a fluid storage region which is integral within the inner region of the transport member, or alternatively defined as the path of a liquid from a liquid releasing source region within the inner region of the transport member to an outlet port region.

The transport path of an liquid transport member can be of substantial length, a length of 100 m or even more can be contemplated, alternatively, the liquid transport member can also be of quite short length, such as a few millimeters or even less. Whilst it is a particular benefit of the present invention to provide high transport rates and also enable large amounts of liquid to be transported, the latter is not a requirement. It can also be contemplated, that only small amounts of liquid are transported over relatively short times, for example when the system is used to transmit signals in the form of liquids in order to trigger a certain response to the signal at an alternative point along the transport member.

In this case, the liquid transport member may function as a real-time signaling device. Alternatively, the transported liquid may perform a function at the outlet port, such as activating a void to release mechanical energy and create a three-dimensional structure. For example, the liquid transport member may deliver a triggering signal to a responsive device comprising a compressed material that is held in vacuum compression within a bag, at least a portion of which is soluble (e.g., in water). When a threshold level of the signaling liquid (e.g., water) delivered by the liquid transport member dissolves a portion of the water soluble region and discontinuously releases the vacuum, the compressed material expands to form a three dimensional structure. The compressed material, for example, may be a resilient plastic foam that has a shaped void of sufficient volume to capture bodily waste. Alternatively, the compressed material may be an absorbent material that functions as a pump by drawing fluid into its body as it expands (e.g., may function as a liquid sink as described below).

The liquid transport can take place along a single transport path or along multiple paths, which can split or re-combine across the transport member.

Generally, the transport path will define a transport direction, allowing definition of the transport cross sectional plane which is perpendicular to said path. The inner/bulk region configuration will then define the transport cross sectional area, combining the various transport paths.

For irregularly shaped transport members and respective regions thereof, it might be necessary to average the transport cross-section over the length of the one or more transport path(s) either by using incremental approximations or differential approximations as well known from geometrical calculations.

It is conceivable, that there will be transport members, wherein the inner region and port regions are readily separable and distinguishable. In other instances, it might take more effort to distinguish and/or to separate the different regions.

Thus, when the requirements are described for certain regions, this should be read to apply to certain materials within these regions. Thereby, a certain region can consist of one homogeneous material, or a region can comprise such a homogeneous material. Also, a material can have varying properties and/or parameters, and thus comprise more than one region. The following description will focus on describing the properties and parameters for the functionally defined regions.

General Functional Description of Transport Member

As briefly mentioned in the above, the present invention is concerned with a liquid transport member, which is based upon direct suction rather than on capillarity. Therein, the liquid is transported through a region into which substantially no air (or other gas) should enter (at all or at least not in a significant amount). The driving force for liquid flowing through such a member can be created by a liquid sink and/or liquid source in liquid communication with the transport member, either externally, or internally.

The direct suction is maintained by ensuring that substantially no air or gas enters the liquid transport member during transport. This means, that the wall regions including the port regions should be substantially air impermeable up to a certain pressure, namely the bubble point pressure as will be discussed in more detail.

Thus, a liquid transport member must have a certain liquid permeability (as described hereinafter). A higher liquid permeability provides less flow resistance, and thus is preferred from this point of view.

In addition, the liquid transport member should be substantially mpermeable for air or gas during the liquid transport.

However, for conventional porous liquid transport materials, and in articular those materials, that function based on capillary transport mechanisms, liquid transport is generally controlled by the interaction of pore size and permeability, such that open, highly permeable structures will generally be comprised of relatively large pores. These large pores provide highly permeable structures, however these structures have very limited wicking heights for a given set of respective surface energies, i.e., a given combination of type of material and liquids. Pore size can also affect liquid retention under normal use conditions.

In contrast to such conventional capillary governed mechanisms, in the present invention, these conventional limitations have been overcome, as it has been surprisingly found, that materials exhibiting a relative lower permeability can be combined with materials exhibiting a relative higher permeability, and the combination provides significant synergistic effects.

In particular, it has been found, that when a highly liquid permeable material having large pores is surrounded by material having essentially no air permeability up to a certain pressure, the already referred to bubble point pressure, but having also relatively low liquid permeability, the combined liquid transport member will have a high liquid permeability and a high bubble point pressure at the same time, thus allowing very fast liquid transport even against an external pressure.

Accordingly, the liquid transport member has an inner region with a liquid permeability which is relatively high to provide maximum liquid transport rate. The permeability of a port region, which can be a part of the wall region circumscribing the bulk region, is substantially less. This is achieved by port regions having a membrane functionality, designed for the intended use conditions. The membrane is permeable to liquids, but not to gases or vapors. Such a property is generally expressed by the bubble point pressure parameter, which is—in short—defined by the pressure up to which gas or air does not penetrate through a wetted membrane.

As will be discussed in more detail, the property requirements have to be fulfilled at the time of liquid transport. It can be, however, that these are created or adjusted by activating a transport member, e.g., prior to usage, which—without or prior to such activation—would not satisfy the requirements but does so after activation. For example, a member can be elastically compressed or collapsed, and expand upon wetting to then create a structure with the required properties.

Generally, for considering how fast and how much liquid can be transported over a certain height (i.e. against a certain hydrostatic pressure) capillary flow transport is dominated by surface energy effects mechanisms and pore structure, which is determined by number of pores, as well as the shape, size, and also pore size distribution.

If, for example, in conventional capillary flow systems or members which are based on capillary pressure as the driving force, liquid is removed at one end of a capillary system such as by a suction means, this liquid is desorbed out of the capillaries closest to this suction device, which are then at least partially filled by air, and which are then refilled through capillary pressure by liquid from adjacent capillaries, which are then filled by liquid from following adjacent capillaries and so on.

Thus, liquid transport through a conventional capillary flow structure is based upon absorption—desorption and re-absorption cycle of the individual pores.

The flow respectively flux is determined by the average permeability along the pathway and by the suction at the end of the transport path. Such a local suction will generally also be dependent on the local saturation of the material, i.e. if the suction device is able to reduce the saturation of the region close to it, the flow/flux will be higher.

However, even if said suction at the end of the transport path is higher than the capillary pressure inside the capillary structure, the internal driving force for liquid is given by the capillary pressure thus limiting liquid transport rates. In addition, such capillary flow structures cannot transport liquid against gravity for heights larger than the capillary pressure, independent of the external suction.

A specific idealized execution of such porous liquid transport members are so-called "capillary tubes", which can be described as parallel pipes with the inner tube diameter and wall thickness defining the overall openness (or porosity) of the system. Such systems will have a relative large flux against a certain height if these are "monoporous", i.e., if the pores have the same, optimal pore size. Then the flow is determined by the pore structure, the surface energy relation, and the cross-sectional area of the porous system, and can be estimated by well know approximations.

Realistic porous structures, such as fibrous or foam type structures, will not transport like the ideal structures of capillary tubes. Realistic porous structures have pores that are not aligned, i.e. not straight, as the capillary tubes and the pore sizes are also non-uniform. Both of these effects often reduce the transport efficiency of such capillary systems.

For one aspect of the present invention, however, there are at least two regions within the transport member with different pore sizes, namely the one or more port region(s) having smaller pore sizes (which in conventional systems would result in very low flow rates) and the inner region having a substantially larger pore sizes (which in conventional systems would result in very low achievable transport heights).

For the present invention, however, the overall flow and transport height through the transport member are synergistically improved by the high permeability of the inner region (which therefore can be relatively long whilst having small cross-sectional areas), and by the relatively high bubble point pressure of the port regions (which can have sufficiently large surfaces, and/or small thickness). In this aspect of the invention, the high bubble point pressure of the port regions is obtained by the capillary pressure of the small pores of said port region, which will—once wetted—prevent air or gas from entering the transport member.

Thus, very high fluid transport rates can be achieved through relatively small cross-sectional areas of the transport member.

In another aspect, the present invention is concerned with liquid transport members, which—once activated, and/or wetted—are selective with regards to the fluids they transport. The port regions of the transport member are—up to a certain limit as can be expressed by the bubble point pressure—closed for the ambient gas (like air), but relatively open for the transport liquid (like water).

The port regions do not require a specific directionality of their properties, i.e. the materials used therein can be used in either orientation of liquid flow there through. Nor is it a requirement for the membranes to have different properties (such as permeability) with regard to certain parts or components of the liquid. This is in contrast to the membranes such as described for osmotic absorbent packets in U.S. Pat. No. 5,108,383 (White et al.), where the membranes have to have a low permeability for the promoter material, such a salt, respectively salt-ions.

Bulk Region

In the following section, the requirements as well as specific executions for the "inner region" or "bulk region" will be described.

A key requirement for the bulk region is to have a low average flow resistance, such as expressed by having a permeability k of at least $10^{-11}$ m$^2$, preferably more than $10^{-8}$ m$^2$, more preferably more than $10^{-7}$ m$^2$, and most preferably more than $10^{-5}$ m$^2$.

One important means to achieve such high permeabilities for the inner regionscan be achieved by utilizing material providing relatively high porosity.

Such a porosity, which is commonly defined as the ratio of the volume of the materials that makes up the porous materials to the total volume of the porous materials, and as determined via density measurements commonly known, should be at least 50%, preferably at least 80%, more preferably at least 90%, or even exceeding 98%, or 99%. In the extreme of the inner region essentially consisting of a single pore, void space, the porosity approaches or even reaches 100%. Another important means to achieve such high permeabilities for the inner regions is using materials with large pores.

The inner region can have pores, which are larger than about 200 $\mu$m, 500 $\mu$m, 1 mm or even 9 mm in diameter or more. For certain applications, such as for irrigation or oil separation, the inner region can have pores as large as 10 cm—e.g., when the inner region is a void tube.

Such pores may be smaller prior to the fluid transport, such that the inner region may have a smaller volume, and expand just prior or at the liquid contact. Preferably, if such pores are compressed or collapsed, they should be able to expand by a volumetric expansion factor of at least 5, preferably more than 10. Such an expansion can be achieved by materials having an elastic modulus of more than the external pressure which, however, must be smaller than the bubble point pressure.

High porosities can be achieved by a number of materials, well known in the art as such. For example fibrous members can readily achieve such porosity values. Non-limiting examples for such fibrous materials that can be comprised in the bulk region are high-loft non-wovens, e.g., made from polyolefin or polyester fibers as used in the hygienic article field, or car industry, or for upholstery or HVAC industry. Other examples comprise fiber webs made from cellulosic fibers.

Such porosities can further be achieved by porous, open celled foam structures, such as—without intending any limitation—for example pulyurethane reticulated foams, cellulose sponges, or open cell foams as made by the High Internal Phase Emulsion Polymerization process (HIPE foams), all well known from a variety of industrial applications such as filtering technology, upholstery, hygiene and so on.

Such porosities can be achieved by wall regions (such as explained in more detail hereinafter) which circumscribe voids defining the inner region, such as exemplified by pipes. Alternatively, several smaller pipes can be bundled.

Such porosities can further be achieved by "space holders", such as springs, spacer, particulate material, corrugated structures and the like.

The inner region pore sizes or permeabilities can be homogeneous throughout the inner region, or can be inhomogeneous.

It is not necessary, that the high porosity of the inner region is maintained throughout all stages between manufacture and use of the liquid transport member, but the voids within the inner region can be created shortly before or during its intended use.

For example, bellow like structures held together by suitable means can be activated by a user, and during its expansion, the liquid penetrates through a port region into the expanding inner region, thereby filling the transport member completely or at least sufficiently to not hinder the liquid flow.

Alternatively, open celled foam materials, such as described in (U.S. Pat. No. 5,563,179 or U.S. Pat. No. 5,387,207) have the tendency to collapse upon removal of water, and the ability to re-expand upon re-wetting. Thus, such foams can be transported from the manufacturing site to the user in a relatively dry, and hence thin (or low-volume), and only upon contact with the source liquid increase their volume so as to satisfy the void permeability requirements.

The inner regions can have various forms or shapes. The inner region can be cylindrical, ellipsoidal, sheet like, stripe like, or can have any irregular shape.

The inner regions can have constant cross-sectional area, with constant or varying cross-sectional shape, like rectangular, triangular, circular, elliptical, or irregular. A cross-sectional area is defined for the use herein as a cross-section of the inner region, prior to addition of source liquid, when measured in the plane perpendicular to the flow path of the transport liquid, and this definition will be used ta determine the average inner region cross-sectional area by averaging the individual cross-sectional areas all over the flow path(s).

The absolute size of the inner region should be selected to suitably match the geometric requirements of the intended use. Generally, it will be desirable to have the minimum dimension for the intended use. A benefit of the designs according to the present invention is to allow much smaller cross-sectional areas than conventional materials. The dimensions of the inner region are determined by the permeability of said inner region, which can be very high, due to possible large pores, as the inner region does not have to be designed under the contradicting requirements of high flux (i.e. large Pores) and high vertical liquid transport (i.e. small pores). Such large pemeabilities allow much smaller cross-sections, and hence very different designs.

Also the length of the inner region can be significantly larger than for conventional systems, as also with regard to this parameter the novel transport member can bridge longer distances and also greater vertical liquid transport heights.

The inner region can be essentially non-deformable, i.e., maintains its shape, form, volume under the normal conditions of the intended use. However, in many uses, it will be desirable, that the inner region allows the complete member to remain soft and pliable.

The inner region can change its shape, such as under deforming forces or pressures during use, or under the influence of the fluid itself. The deformability or absence thereof can be achieved by selection of one or more materials in the inner region (such as a fibrous member), or can be essentially determined by the circumscribing regions, such as by the wall regions of the transport member. One such approach is to utilize elastomeric materials as the wall material.

The voids of the inner region can be confined by wall regions only, or the inner region can comprise internal separations therein.

If, for example, the inner region is made up of parallel pipes, with impermeable cylindrical walls, these would be considered to be such internal separations, thereby possibly creating pores which are unitary with the inner, hollow opening of the pipes, and possibly other pores created by the interstitial spaces between the pipes. If, as a further example, the inner region comprises a fibrous structure, the fiber material can be considered to form such internal separations.

The internal separations of the inner region can have surface energies adapted to the transported liquid. For example, in order to ease weuting and/or transport of aqueous liquids, the separations or parts thereof can be hydrophilic. Thus, in certain embodiments relating to the transport of aqueous liquids, it is preferred to have the separations of the inner regions to be wettable by such liquids, and even more preferred to have adhesion tensions of more than 65 mN/m, more preferably more than 70 mN/m. In case of the transported liquid is oil based, the separations or parts thereof can be oleo- or lipophilic.

The confining separations of the inner region may further comprise materials which significantly change their properties upon wetting, or which even may dissolve upon wetting. Thus, the inner region may comprise an open cell foam material having a relatively small pore at least partially being made of soluble material, such as polyvinylalcohol or the like. The small porosity can draw in liquid at the initial phase of liquid transport, and then rapidly dissolve so as to then leave large voids filled with liquid.

Alternatively, such materials may fill larger pores, completely or partially, For example, the inner region can comprise soluble materials, such as poly(vinyl) alcohol or poly(vinyl) acetate. Such materials can fill the voids, or support a collapsed state of the voids before the member is contacted with liquid. Upon contact with fluid, such as water, these materials may dissolve and thereby create empty or expanded voids.

In one embodiment, the voids of the inner region (which can make up essentially the complete inner region) are essentially completely filled with an essentially incompressible fluid.

The term "essentially completely" refers to the situation, where sufficient void volume of the inner region is filled with the liquid such that a continuous flow path can be established.

Preferably, most of the void volume, preferably more than 90%, more preferably more than 95%, and even more preferably more than 99%, including 100%, is filled with the liquid. The inner region can be designed so as to enhance accumulation of gas or other liquid in parts of the region where it is less detrimental. The remainder of the voids can then be filled with other fluid, such as residual gas or vapors, or immiscible liquid like oil in an inner region filled with aqueous liquids, or can be solids, like particulates, fibers, films.

The liquid comprised in the inner region can be of the same type as the liquid being intended to be transported. For example, when water based liquids are the intended transported medium, the inner region of the transport member can be filled with water—or if oil is the intended transport liquid, the inner region can be filled with oil.

The liquid in the inner region can also be different—whereby these differences can be relatively small in nature (such as when the intended transport liquid is water, the inner region liquid can be an aqueous solution, and vice versa). Alternatively, the intended transport liquid can be quite different in its properties, when compared to the liquid which has been pre-filled into the inner region, such as when the source liquid is oil, which is transported through a pipe initially filled with water and closed by suitable inlet and outlet ports, whereby the water leaves the member by a suitable outlet port region, and the oil enters the member by a suitable inlet port region. In this specific embodiment, the total amount of transported liquid is limited by the amount which can be received within the member respectively the amount of liquid exchanged, unless there were, for example, outlet port regions comprising materials with properties compatible with the liquids so as to allow functionality with one or both of the liquids.

The liquid of the inner region and the liquid to be transported can be mutually soluble, such as salt solutions in water. For example, if the liquid transport member is intended for the transport of blood or menses, the inner region can be filled with water.

In another embodiment, the inner region comprises a vacuum, or a gas or vapor below the corresponding equilibrium, ambient or external, pressure at the respective temperatures, and volumetric conditions. Upon contact with the transported liquid, the liquid can enter into the inner region by the permeable port regions (as described hereinafter), and then fill the voids of the inner region to the required degree. Thereafter, the now filled inner region functions like a "pre-filled" region as described in the above.

The above functional requirements and structural embodiments of the inner region can be satisfied by a number of suitable structures. Without being limited in creating structures satisfying suitable inner regions, the following describes a range of preferred embodiments.

A simple and yet very descriptive example for an inner region is an empty tube defined by impermeable or semipermeable walls, as already discussed and depicted in FIG. 2. The diameter of such tubes can be relatively large compared to diameters commonly used for transport in capillary systems. The diameter of course depends highly on the specific system and intended use.

For example, for hygiene applications such as diapers, pore sizes of 2–9 mm or more have been found to function satisfactorily.

Also suitable is the combination of parallel tubes of a suitable diameter of from about 0.2 mm to several cm to a tube bundle, such as (in principle) known from other engineering design principles such as heat exchanger systems.

For certain applications, pieces of glass tubes can provide the right functionality, however, for certain applications such structures may have some mechanical strength constraints. Suitable tubes can also be made of silicon, rubber, PVC, etc., e.g., Masterflex 6404-17 by Norton, distributed by the Barnant Company, Barrington, Ill. 60010 U.S.

Yet another embodiment can be seen in the combination of mechanically expanding elements, such as springs or which can open void space in the structure if the expansion direction is oriented such that the appropriate pore size is also oriented along the flow path direction.

Such materials are well known in the art, and for example disclosed in U.S. Pat. No. 5,563,179, U.S. Pat. No. 5,387,207, U.S. Pat. No. 5,632,737 all relating to HIPE foam materials, or in U.S. Pat. No. 5,674,917 relating to absorbent foams, or in EP-A-0.340.763, relating to highly porous fibrous structures or sheets, such as made from PET fibers.

Other materials can be suitable even when they do not satisfy all the above requirements at the same time, if this deficiency can be compensated by other design elements.

Other materials having relatively large pores are highloft non-woven, filter materials as open cell foams from Recticel in Brussel, Belgium such as Bulpren, Filtren (Filtren TM10 blue, Filtren TM20 blue, Filtren TM30 blue, Filtren Firend 10 black, Filtren Firend 30 black, Filtren HC 20 grey, Filtren Firend HC 30 grex, Bulpren S10 black, Buipren S20 black, Bulpren S30 black).

Another material having relatively large pores—even though the porosity is not particularly high—is sand with particles larger than 1 mm, specifically sand with particles larger than 5 mm Such fibrous or other materials may, for example become very useful by being corrugated, however, excessive compression should be avoided. Excessive compression can result in a non-homogeneous pore size distribution with small pores within the inner material, and insufficiently open pores between the corrugations.

A further embodiment to exemplify a material with two pore size regions can be seen in PCT application US97/20840, relating to a woven loop structure.

The inner region may comprise absorbent materials, such as super absorbent gelling materials or other materials as described for being suitable as a liquid sink material herein after. Further, the promoter materials of Membrane Osmotic packets, (MOP) such as disclosed in U.S. Pat. No. 5,082,723 (White, Allied Signals) can be suitable for being used in the inner region.

The inner region may further be constructed form several materials, i.e. for example from combinations of the above.

The inner region may also comprise stripes, particulates, or other in-homogeneous structures generating large voids between themselves and acting as space holders.

As will be described in more details for the port regions, the fluids in the inner region must not prevent the port regions from being filled with the transport liquid.

Thus, the degree of vacuum, for example, or the degree of miscibility or immiscibility must not be such that liquids from the port region are drawn into the inner region without the port region(s) being refilled with transport liquid.

Wall Region

The liquid transport member according to the present invention comprises in addition to the inner regions a wall region circumscribing this inner region in the geometric definition as described hereinbefore. This wall region must comprise at least an inlet port region and an outlet port region, as described hereinafter. The wall region can further comprise materials, which are essentially impermeable to liquids and/or gases, thereby not interfering with the liquid handling functionality of the port regions, and also preventing ambient gases or vapors from penetrating into the liquid transport member.

Such walls can be of any structure or shape, and can re present the key structural element of the liquid transport member. Such walls can be in the shape of a straight or bent pipe, of a flexible pipe, or of cubical shape and so on. The walls can be thin, flexible films, circumscribing the inner region. Such walls can be expandable, either permanently via deformation or elastically via an elastomeric film, or upon activation.

Whilst the wall regions as such are an essential element for the present invention, this is particularly true for the port region comprised in such wall regions, and described in the following. The properties of the remaining parts of the wall regions can be important for the overall structure, for resilience, and other structural effects.

Port Region(s)

The port regions can generally be described to comprise materials which have different permeabilities for different fluids, namely they should be permeable for the transport liquid, but not for the ambient gas (like air), under otherwise same conditions (like temperature, or pressure, . . . ) and once they are wetted with/filled with the transport liquid or similarly functioning liquid.

Often, such materials are described as membranes with respective characteristic parameters.

In the context of this invention, a membrane is generally defined as a region, that is permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion.

For a given set of conditions, membranes will often have selective transport properties for liquids, gases or suspensions depending on the type of medium to be transported. They are therefore widely used in filtration of fine particles out of suspensions (e.g. in liquid filtration, air filtration). Other type of membranes show selective transport for different type of ions or molecules and are therefore found in biological systems (e.g. cell membranes, molecular sieves) or in chemical engineering applications (e.g. for reverse osmosis).

Microporous hydrophobic membranes will typically allow gas to permeate, while water-based liquids will not be transported through the membrane if the driving pressure is below a threshold pressure commonly referred to as "breakthrough" or "bridging" pressure.

In contrast, hydrophilic microporous membranes will transport water based liquids. Once wetted, however, gases (e.g. air) will essentially not pass through the membrane if the driving pressure is below a threshold pressure commonly referred to as "bubble point pressure".

Hydrophilic monolithic films will typically allow water vapor to permeate, while gas will not be transported rapidly through the membrane.

Similarly, membranes can also be used for non-water based liquids such as oils. For example, most hydrophobic materials will be in fact oleophilic. A hydrophobic microporous membrane will therefore be permeable for oil but not for water and can be used to transport oil, or also separate oil and water.

Membranes are often produced as thin sheets, and they can be used alone or in combination with a support layer (e.g. a nonwoven) or in a support element (e.g. a spiral holder). Other forms of membranes include but are not limited to polymeric thin layers directly coated onto another material, bags, corrugated sheets.

Further known membranes are "activatable" or "switchable" membranes that can change their properties after activation or in response to a stimulus. This change in properties might be permanent or reversible depending on the specific use. For example, a hydrophobic microporous layer may be coated with a thin dissolvable layer e.g. made from poly(vinyl)alcohol. Such a double layer system will be impermeable to gas. However, once wetted and the poly (vinyl)alcohol film has been dissolved, the system will be permeable for gas but still impermeable for aqueous liquids.

Conversely, if a hydrophilic membrane is coated by such a soluble layer, it might become activated upon liquid contact to allow liquid to pass through, but not air.

In another example, a hydrophilic microporous membrane is initially dry. In this state the membrane is permeable for air. Once wetted with water, the membrane is no longer air permeable. Another example for a reversible switching of a membrane in response to a stimulus is a microporous membrane coated with a surfactant that changes its hydrophilicity depending on temperature. For example the membrane will then be hydrophilic for warm liquid and hydrophobic for cold liquid. As a result, warm liquid will pass through the membrane while cold liquid will not. Other examples include but are not limited to microporous membranes made from an stimulus activated gel that changes its dimensions in response to pH, temperature, electrical fields, radiation or the like.

Properties of Port Regions

The port regions can be described by a number of properties and parameters.

A key aspect of the port region is the permeability.

The transport properties of membranes may in general be described by a permeability function using Darcy's law which is applicable to all porous systems:

$$q = 1/A * dV/dt = k/\eta * \Delta p/L$$

Thus, a volumetric flow dV/dt through the membrane is caused by an external pressure difference $\Delta p$ (driving pressure), and the permeability function k may depend on the type of medium to be transported (e.g. liquid or gas), a threshold pressure, and a stimulus or activation. Further relevant parameters impacting on the liquid transport are the cross-section A, the volume V respectively the change over time thereof, and the length L of the transport regions, and the viscosity $\eta$ of the transported liquid.

For porous membranes, the macroscopic transport properties are mainly depending on the pore size distribution, the porosity, the tortuosity and the surface properties such as hydrophilicity.

If taken alone, the permeability of the port regions should be high so as to allow large flux rates there through. However, as permeability is intrinsically connected to other properties and parameters, typical permeability values for port regions or port region materials will range from about $6*10^{-20}$ m$^2$, to $7*10^{-18}$ m$^2$, or $3*10^{-14}$ m$^2$, up to $1.2*10^{-10}$ m$^2$ or more.

A further parameter relevant for port regions and respective materials is the bubble point pressure, which can be measured according to the method as described hereinafter.

Suitable bubble point pressure values depend on the type of application in mind. The table below lists ranges of suitable port region bubble point pressure (bpp) for some applications, as determined for respective typical fluids: pplication bpp (kPa)

| Application | bpp (kPa) broad range | typical range |
|---|---|---|
| Diapers | 4.5 to 35 | 4.5 to 8 |
| Catamenials | 1 to 35 | 1 to 5 |
| Irrigation | <2 to >50 | 8 to 50 |
| Grease absorption | 1 to 20 | 1 to 5 |
| Oil Separation | <1 to about 50 | |

In a more general approach, it has been found useful, to determine the bpp for a material by using a standardized test liquid, as described in the test methods hereinafter.

Port Region Thickness and Size

The port region of a liquid transport member is defined as the part of the wall having the highest permeability. The port region is also defined by having the lowest relative permeability when looking along a path from the bulk region to a point outside the transport member.

The port region can be constructed by readily discernible materials, and then both thickness and size can be readily determined. The port region can, however, have a gradual transition of its properties either to other, impermeable regions of the wall region, or to the bulk region. Then the determination of the thickness and of the size can be made as described hereinafter. When looking at a segment of the wall region, such as depicted in FIG. 5A, this will have a surface, defined by the cornerpoints ABCD, which is oriented towards the inner or bulk region, and a surface EFGH oriented towards the outside of the member. Thus the thickness dimension is oriented along the lines AE, BF, and so on, i.e. when using Cartesian co-ordinates, along the z-direction. Analogously, the wall region will have the major extension along the two perpendicular directions, i.e. x-, and y- direction.

Figure 5B:
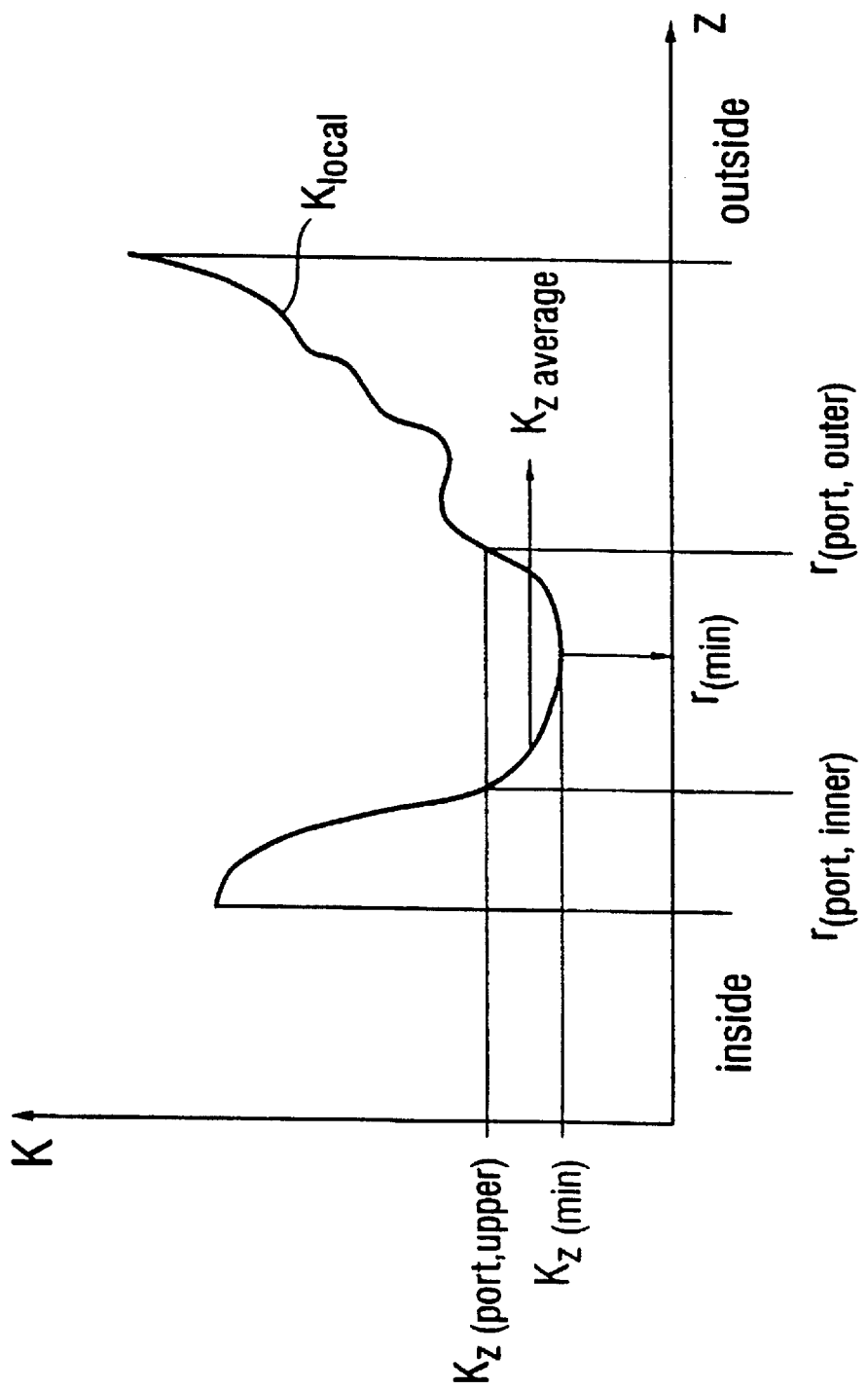
FIGS. 5 A, B, C: Schematic representation for the determination of port region thickness.

Then, the port region thickness can be determined as follows:

a) In case of essentially homogeneous port region properties at least in the direction through the thickness of the region, it is the thickness of a material having such a homogeneous permeability (such as with a membrane film);

b) It is the thickness of the membrane if this is combined with a carrier (be this carrier inside or outside of the membrane)—i.e. this refers to a non-continuous/step change function of the properties along this path.

c) For a material having a (determinable) continuous gradient permeability across any segment as in FIG. 5A, the following steps can be taken to reach a determinable thickness (refer to FIG. 5B):

c0) First, a permeability profile is determined along the z-axis, and the curve $k_{[local]}$ vs r is plotted; for certain members, the porosity or pore size curve can also be taken for this determination with appropriate changes of the subsequent procedure.

c1) Then the point of lowest permeability ($k_{min}$) is determined, and the corresponding length reading ($r_{[min]}$) is taken.

c2) As the third step, the "upper port region permeability" is determined as being 10 times the value of $k_{min}$ c3) As the curve has a minimum at $k_{min}$ there will be two corresponding $r_{inner}$ and $r_{outer}$, defining the inner and outer limit of the port region respectively.

c4) The distance between the two limits defines the thickness, and the average $k_{port\ average}$ will be determined across this].

If this approach fails due to indeterminable gradient permeability, porosity or pore size, the thickness of the port region will be set to 1 micrometer.

As indicated in the above, it will often be desirable to minimize the thickness of the port region, respectively the membrane materials comprised therein. Typical thickness values are in the range of less than 100 µm, often less than 50 µm, 10 µm, or even less than 5 µm.

Figure 5C:
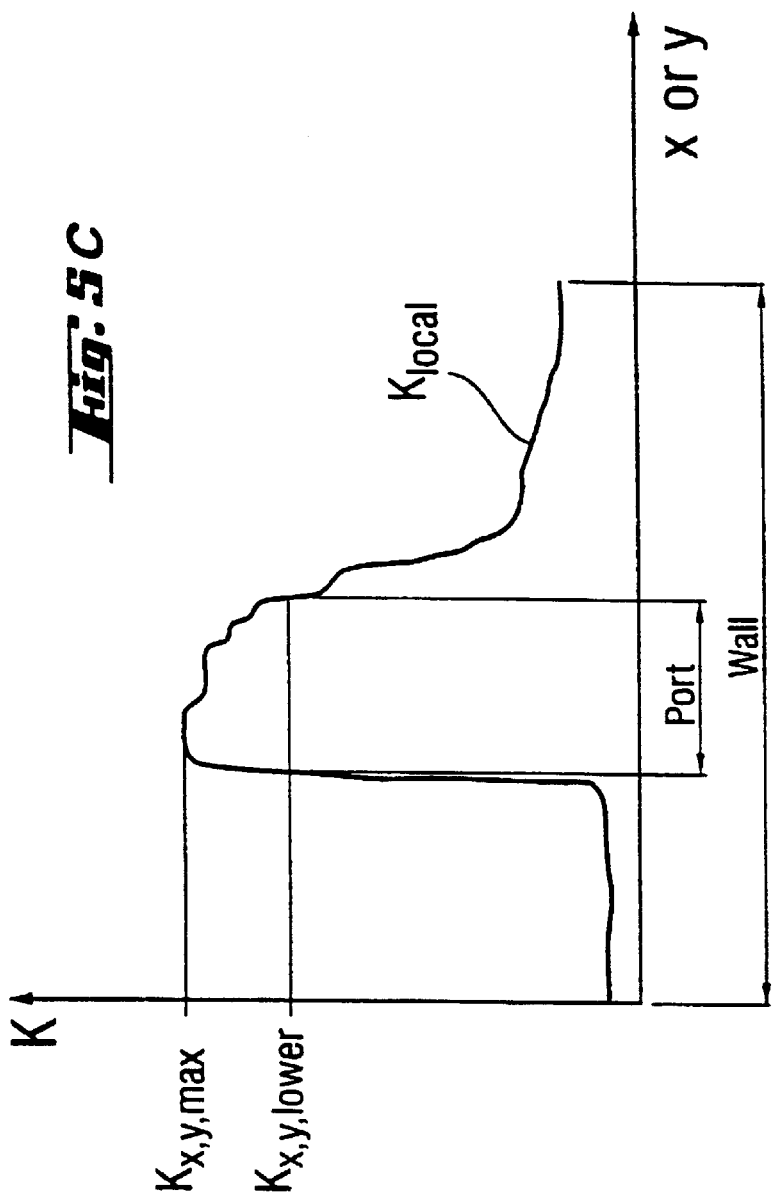

Quite analogously, the x-y extension of the port region can be determined. In certain liquid transport member designs it will be readily apparent, which part of the wall region are port regions. In other designs, with gradually changing properties across the wall region, the local permeability curves along the x- and y direction of the wall region can be determined, and plotted analogously to FIG. 5B as shown in FIG. 5C. In this instance, however, the maximum permeability in the wall region defines the port regions, hence the maximum will be determined, and the region having permeabilities of not less than a tenth of the maximum permeability surrounding this maximum is defined as the port region.

Yet another parameter useful for describing aspects of the port regions useful for the present invention is the permeability to thickness ratio, which in the context of the present invention is also referred to as "membrane conductivity".

This reflects the fact, that—for a given driving force—the amount of liquid penetrating through a material such as a membrane is on one side proportional to the permeability of the material, i.e. the higher the permeability, the more liquid will penetrate, and on the other side inversely proportional the thickness of the material.

Henceforth, a material having a lower permeability compared to the same material having a decrease in thickness, shows that thickness can compensate for this permeability deficiency (when regarding high rates a being desirable).

Thus, this parameter can be very useful for designing the port region materials to be used.

Suitable conductivity k/d depends on the type of application in mind. The table below lists ranges of typical k/d for some exemplary applications:

| Application | k/d ($10^{-9}$ m) broad range | typical range |
|---|---|---|
| Diapers | $10^{-6}$ to 1000 | 150 to 300 |
| Feminine protection | | 100 to 500 |
| Irrigation | — | 1 to 300 |
| Grease absorption | — | 100 to 500 |
| Oil Separation | | 1 to 500 |

Of course, the port regions have to be wettable by the transport fluid, and the hydrophilicity or lipophilicity should be designed appropriately, such as by using hydrophilic membranes in case of transporting aqueous liquids, or oleophilic membranes in case of lipophilic or oily liquids.

The surface properties in the port region can be permanent, or they can change with time, or usage conditions.

It is preferred, that the receding contact angle for the liquid to be transported is less than 70°, more preferably less than 50°, even more preferred less than 20° or even less than 10°. Further, often it is preferred, that the material has no negative impact on the surface tension of the transported liquid.

For example, a lipohilic membrane may be made from lipophilic polymers such as polyethylene or polypropylene and such membranes will remain liphophilic during use.

Another example is a hydrophilic material allowing aqueous liquids to be transported. If a polymer like polyethylene or polypropylene is to be used, this has to be hydrophilized, such as by surfactants added to the surface of the material or added to the bulk polymer, such as adding a hydrophilic polymer prior to forming the port material. In both instances, the imparted hydrophilicity may be permanent or not, e.g. it could be washed away with the transport liquid passing therethrough. However, as it is an important aspect of the present invention, that the port regions remain in a wetted state so as to prevent gas passing through, the lack of hydrophilizer will not be significant once the port regions are wetted.

Maintaining Liquid Filling of Membrane.

For a porous membrane to be functional once wetted (permeable for liquid, not-permeable for air) at least a continuous layer of pores of the membrane always need to be filled with liquid and not with gas or air. Thus, it can be desirable for particular applications to minimize the evaporation of the liquid from the membrane pores, either by a decrease of the vapor pressure in the liquid or by an increase the vapor pressure in the air. Possible ways to do this include—without any limitation:

Sealing of the membrane with a impermeable wrap to avoid evaporation between production and usage. Use of strong desiccants (e.g. $CaCl_2$) in the pores, or use of a liquid with low vapor pressure in the pores that mixes with the transported fluid, such a glycerin.

Alternatively, the port region may be sealed with soluble polymers, such as poly vinyl alcohol, or poly vinyl acetate, which are dissolved upon contact with liquids and which thereby activate the functionality of the transport member.

Apart from the liquid handling requirements, the port regions should satisfy certain mechanical requirements.

First, the port regions should not have any negative effect on the intended use conditions. For example when such members are intended in hygienic absorbent articles, the comfort and safety must not be negatively impacted.

Thus it will often be desirable, that the port regions are soft, and flexible, but this may not always be the case. However, the port region should be sufficiently strong to withstand practical use stress, such as tear stress or puncturing stress or the like.

In certain designs, it might be desirable for the port region materials to be extensible or collapsible, or bendable.

Even a single hole in the membrane (e.g. caused by puncturing during use), a failure in membrane sealing (e.g. owing to production), or the membrane tearing (e.g. due to in-use pressure being exerted) can under various conditions lead to a failure of the liquid transport mechanism. Whilst this can be used as a destructive test method to determine if a materials or member functions according to the present invention, and as described hereinafter, this is not desirable during its intended use. If air or another gas penetrates into the inner region, this may block the liquid flow path within the region, or it may also interrupt the liquid connection between the bulk and port regions.

A possibility to make an individual member more robust, is to provide in certain parts of the inner region remote from the main liquid flow path, a pocket where air that enters the system is allowed to accumulate without rendering the system non functional.

A further way to address this issue is to have several liquid transport member in a (functionally or geometrically) parallel arrangement instead of a single liquid transport member. If one of the members fails, the others will maintain the functionality of the "liquid transport member battery".

The above functional requirements of the port regions can be satisfied by a wide range of materials or structures described by the following structural properties or parameters.

The pore structure of the region, respectively of the materials therein, is an important parameter impacting on properties like permeability and bubble point pressure.

Two key aspects of the pore structure are the pore size, and pore size distribution. A suitable method to characterize these parameters at least on the surface of the region is by optical analysis. Another suitable method for the characterization of these properties and parameters is the use of a Capillary Flow Porosimeter, such as described hereinafter.

As has been discussed above in the context of permeability, permeability is influenced by the pore size and the thickness of the regions, respectively the part of the thickness which is predominantly determining the permeability.

Henceforth, it has been found, that for example for aqueous systems typical average pore size values for the port region are in the range of 0.5 $\mu$m to 500 $\mu$m. Thus the pores have preferably an average size of less than 100 $\mu$m, preferably less than 50 $\mu$m, more preferably less than 10 $\mu$m or even less than 5 $\mu$m. Typically, these pores are not smaller than 1 $\mu$m.

It is an important feature for example of the bubble point pressure, that this will depend on the largest pores in the region, which are in a connected arrangement therein. For example, having one larger pore embedded in small ones does not necessarily harm the performance, whilst a "cluster" of larger pores together might very well do so.

Henceforth, it will be desirable to have narrow pores size distribution ranges.

Another aspect relate to the pore walls, such as pore wall thickness, which should be a balance of openess and strength requirements. Also the pores should be well connected to each other along the flow direction, to allow liquid passing through readily.

As some of the preferred port region materials can be thin membrane materials, these in themselves may have relatively poor mechanical properties. Henceforth, such membranes can be combined with a support structure, such as a coarser mesh, threads or filaments, a non-woven, apertured films or the like.

Such a support structure could be combined with the membrane such that it is positioned towards the inner/bulk region or towards the outside of the member.

Size/Surface Area of Port Regions

The size of the port regions is essential for the overall performance of the transport member, and needs to be determined in combination with the "permeability to thickness" (k/d) ratio of the port region.

The size has to be adapted to the intended use, so as to satisfy the liquid handling requirements. Generally, it will be desirable to have the liquid handling capability of the inner/bulk region and the port regions to be compatible, such that neither is a grossly limiting factor for liquid transport compared to the other. As for a given driving force the flux (i.e. the flow rate through a unit area) of the membrane port region will generally be lower than the flux through the inner region, it may be preferred to design the membrane port region relatively thin in thickness and/or larger in size (surface) than the cross-section of the inner region.

Thereby, the exact design and shape of the port regions can vary over a wide range.

For example, if the transport members function is intended to provide a trigger or signal from one port region to another, the port regions can be relatively small, such as about the size of the cross-section of the inner region, such that a substantially smaller transport member results.

Or, when liquids are to be quickly captured and transported, distributed or stored, the member can be shaped for example in the shape of a dog bone with relatively large port regions at either end of the transport member or alternatively, the port regions can be spoon shaped so as to increase the receiving area.

Alternatively, the port regions can be non-flat, such as for example corrugated, or folded, or having other forms so as to create relative large surface area to volume ratios, such as well known in the filter technology.

Whilst the inlet port and the outlet port can be designed to satisfy the same basic requirements, and thus can be one and the same material, this does not need to be the case. The inlet and outlet port regions can be different with regard to one or more material or performance parameters. The different port regions can be readily discernible, such as by being represented by different materials and/or by being separated by other materials, or the port regions can differ by a property or parameter gradient, which can be continuous or stepwise.

One essentially continuous material can have a gradient of properties along either the surface of the material, in the thickness dimension, or both, so as to be able to represent several parts of the wall or inlet or outlet port regions.

The port region properties may be constant over time, or they may change with time, such as being different before and during use.

For example, the port regions can have properties unsuitable for functioning in members according to the present invention until the point of use. The port regions may be activated, for example by manual activation, intervention by the person using the member, or by an automatic activation means, such as by wetting of the transport member. Other alternative mechanisms for activation of the port regions can include temperature change, for example from an ambient temperature to the body temperature of a wearer, or pH, for example of the transport liquid, or an electrical or mechanical stimulus.

As has been discussed in the context of osmotic packet materials in the above, membranes useful for the present invention have no specific requirement of a certain salt impermeability.

Whilst the port regions and suitable materials have been described with regard to their properties or descriptive parameters, the following will describe some of the materials that satisfy these various requirements, thereby focusing on the transport of aqueous liquids.

Suitable materials can be open celled foams, such as High Internal Phase Emulsion foams, can be Cellulose Nitrate Membranes, Cellulose Acetate Membranes, Polyvinyidifluorid films, non-wovens, woven materials such as meshes made from metal, or polymers as Polyamide, or Polyester.

Other suitable materials can be apertured Films, such as vacuum formed, hydroapertured, imechanically or Laser apertured, or films treated by electron, ion or heavy-ion beams.

Specific materials are Cellulose acetate membranes, such as also disclosed in U.S. Pat. No. 5,108,383 (White, Allied-Signal Inc.), Nitrocellulose membranes such as available from e.g. from Advanced Microdevices (PVT) LTD, Ambala Cantt. INDIA called CNJ-10 (Lot # F 030328) and CNJ-20 (Lot # F 024248), Cellulose acetat membranes, Cellulose nitrate membranes, PTFE membranes, Polyamide membranes, Polyester membranes as available e.g. from Sartorius in Göttingen, Germany and Millipore in Bedford USA, can be very suitable. Also microporous films, such as PE/PP film filled with $CaCO_3$ particles, or filler containing PET films as disclosed in EP-A-0.451.797.

Other embodiments for such port region materials can be ion beam apertured polymer films, such as made from PE such as described in "Ion Tracks and Microtechnology— Basic Principles and Applications" edited by R. Spohr and K. Bethge, published by Vieweg, Wiesbaden, Germany 1990.

Other suitable materials are woven polymeric meshes, such as polyamide or polyethylene meshes as available from Verseidag in Geldern-Waldbeck, Germany, or SEFAR in Rüschlikon, Switzerland. Other materials which can be suitable for present applications are hydrophilized wovens, such as known under the designation DRYLOFT® from Goretex in Newark, Del. 19711, USA.

Further, certain non-woven materials are suitable, such as available under the designation CoroGard® from BBA Corovin, Peine, Germany, namely if such webs are specially designed towards a relatively narrow pore size distribution, such as by comprising "melt-blown" webs.

For applications with little requirements for flexibility of the members, or where even a certain stiffness is desirable, metal filter meshes of the appropriate pore size can be suitable, such as HIGHFLOW of Haver & Böcker, in Oelde, Germany.

Additional Elements

Whilst the definition of bulk, wall, and outer region has been made in the above in relation to the function of each of these regions, there may optionally elements be added to the materials forming these regions, which can extend into a neighbouring region without extending the liquid handling functionality, but rather improve other properties, such as the mechanical strength, or tactile or visual aspects of the materials forming the regions or of the complete structure. For example, a support structure may be added to the outside of the wall or port region, which may be so open that it does not impact on the fluid handling properties, and as such would be considered functionally to belong to the outer region. When such an open support element extends from the wall region into the inner or bulk region, it will functionally belong to the bulk region. If there is a gradual transition between these materials and/or elements, the definitions made for the respective functional regions will enable a clear distinction of the region forming materials, and the additional elements.

Further, there can be elements attached to or integral with the liquid transport member to aid its implementation into an absorbent system, or an article comprising an liquid transport member.

Transport Member Functionality

During absorption, both liquid transport members according to the present invention as well as certain conventional materials do not draw air into their respective structures, for conventional materials, fibrous materials or conventional foams, the liquid pulled into the structure displaces air within the structure. However, conventional porous materials, such as fibrous structures, typically do draw air into themselves during desorption, air enters as liquid is drawn out of the structure. The liquid transport member according to the present invention does not draw air into the structure under normal usage conditions. The property that determines the point at which air will enter the system is referred to herein as bubble point pressure. Air will not enter the transport member until the bubble point pressure (bpp) is reached, due to the membrane functionality of the port region(s) material.

Thus, once liquid has entered the member, it will not be replaced by air—up to the bpp of the member.

Permeability

A further property of the liquid transport member is the permeability k (liquid transport member) as the average permeability along the flow path of the transported liquid.

The liquid transport member according to the present invention has a permeability which is higher than the permeability of a capillary system with equal liquid transport capability. This property is referred to as the a "critical permeability" k {crit}. The critical permeability of the liquid transport member of the present invention is preferably at least twice as high as a capillary system with equal vertical liquid transport capability more preferably at least four times as high, and most preferably at least ten times greater than a capillary system with equal vertical liquid transport capability.

For capillary tubes, the permeability k {crit} can be determined via the adhesion tension as derived from Darcy's law as follows:

$$k\{crit\}=(\epsilon\{liquid\ transport\ member\}/2)*(\sigma*\cos(\Theta))2/(bpp\ \{liquid\ transport\ member\}2)$$

wherein k {crit} is the critical permeability in units of $[m^2]$;

$\epsilon$ {liquid transport member} is the average porosity of the liquid transport member [-];

$\sigma$ {liqu} is the surface energy of the liquid in [cP];

$\sigma*\cos(\Theta)$ defines the adhesion tension in [cP] with the receding contact angle $\Theta$, bpp {liquid transport member} is the bubble point pressure of the liquid transport member, expressed in [kPa], as discussed in the above.

The maximum value which can be reached for such a system can be approximated by assuming the maximum value for the term $\cos(\Theta)$, namely 1:

$$k\{crit,\ max\}=(\epsilon\{liquid\ transport\ member\}/2)*\sigma\{liquid\}2/(bpp\ \{liquid\ transport\ member\})2$$

Another way to express the k {crit} is via the ability of the member to transport liquid vertically at least against a hydrostatic pressure corresponding to a certain height h and gravity constant g:

$$k\{crit,\ max\}=(\epsilon\{liquid\ transport\ member\}/2)*\sigma\{liqu\}**2/(\rho\{liqu\}*g*h)**2.$$

The permeability of a material or transport member can be determined by various methods, such by using the Liquid Transport Test or by the Permability test, both as described hereinafter, and then compared to the critical permeability as calculated from the above equations.

Whilst the bpp property has already been discussed in the context of the port regions, also the complete transport member can be described thereby. Accordingly, suitable bpp for the member depends on the intended use, and suitable as well as typical values and ranges are essentially the same for the member as for the port region as described above.

A liquid transport member according to the present invention can also be described by being substantially air impermeable up to a certain bpp, whereby the liquid transport member of the present invention has an overall permeability which is higher than the permeability for a given material having a homogeneous pore size distribution and an equivalent bpp.

Yet another way to describe the functionality of a liquid transport member is by using the average fluid permeability $k_b$ of the bulk/inner region, and the bubble point pressure of the member.

Figure 6:
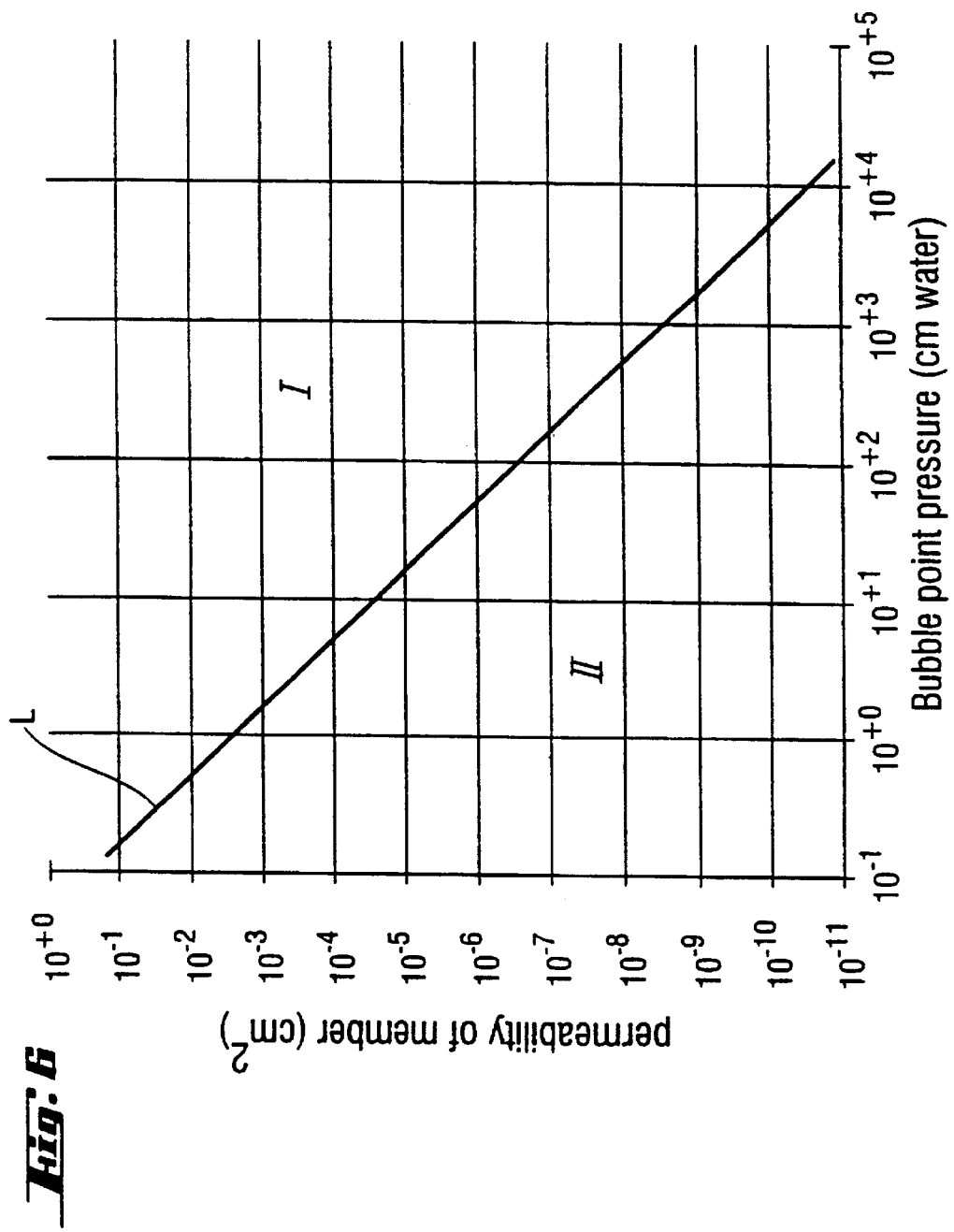
FIG. 6: Correlation of permeability and bubble point pressure.

The liquid transport member according to the present invention should have a relatively high bpp {liquid transport member} and a high k {liquid transport member} at the same time. This can be graphically represented when plotting k{liquid transport member} over bbp in a double logarithmic diagram (as in FIG. 6 wherein the bbp is expressed in "cm height of water column", which then can be readily converted into a pressure).

Therein, for a given surface energy combination of the liquid and the member materials generally a top left to down right correlation can be observed. Members according to the present invention are have properties in the upper right region (I) above the separation line (L), whilst properties of conventional materials are much more in the left lower corner in the region (II), and have the limitations of the pure capillary transport mechanism, as schematically indicated by the straight line in the log-log diagram.

Yet another way to describe the functionality of the liquid transport member is to consider the effect of liquid transport as a function of the driving force.

In contrast, for liquid transport members according to the present invention, the flow resistance is independent from the driving force as long as the pressure differential is less than the bpp of the transparent member. Thus the flux is proportional to the driving pressure (up to the bpp).

A liquid transport member according to the present invention can further be described by having high flux rates, as calculated on the cross-sectional area of the inner region. Thus, the member should have an average flux rate at 0.9 kPa additional suction pressure differential to the height Ho when tested in the Liquid Transport Test at a height $H_0$, as described herein after, of at least 0.1 $g/s/cm^2$, preferably of at least 1 $g/cm^2/sec$, more preferably at least 5 $g/cm^2/sec$, even more preferably at least 10 $g/cm^2/sec$, or even at least 20 $g/cm^2/sec$, and most preferably at least 50 $g/cm^2/sec$.

In addition to the above requirements, the liquid transport member should have a certain mechanical resistance against external pressure or forces.

For certain embodiments, the mechanical resistance to external pressures or forces can be relatively high to prevent squeezing liquid out of the transport member, which for example, can be achieved by using stiff/non-deformable material in the inner region.

For certain other embodiments, this resistance can be in a medium range, thus allowing exploitation of external pressure or forces on the transport member for creating a "pumping effect".

In order to further explain suitable structures for a liquid transport member, the above mentioned simple example of a hollow tube having an inlet and outlet, said inlet and outlet being covered, i.e. closed, by membranes is considered. This type of structure can alternatively include a further support structure such as an open mesh attached to the port region membrane towards the inner region.

Therein, the permeability requirement can be satisfied by the membrane itself, i.e. not considering the effect of the support structure, if the support structure is sufficiently open to have no negative impact on the overall permeability or on the liquid handling properties thereof. Then, the thickness of the port region refers to the thickness of the membrane only—i.e. not including the thickness of the support structure. It will become apparent in the specific context, if for example such a support structure should be seen as an element of the port region having no significant impact on the port region properties, or—for example if the support structure has a significant thickness and thus impacts on the permeability for the liquid after the port region is penetrated—whether the support structure should be considered as a part of the inner region. If, for example, the support structure becomes more extended in thickness, still remaining connected with the membrane, it yet can be considered as functionally belonging to the inner region, such as when the permeability of the composite "support—inner void" is significantly impacted by the permeability of the support structure.

Accordingly, this principle should be considered for each of the respective aspects, such as when looking at the port region(s), the bulk regions or the complete transport member.

The following describes how various elements can be combined to create structures suitable as a liquid transport member. It should be noted, that because of the multiple design options one or the other structure might not be discernible by all of the above described properties, but it will be readily apparent to the skilled person to design even further options following the general teachings in combination with the more specific embodiments.

Relative Permeability

If the permeability of both the inner/bulk region and the port regions can be determined independently, it is preferred that one or both of the port regions have a lower liquid permeability than the inner region.

Thus, a liquid transport member should have a ratio of the permeability of the bulk region to the port region of preferably at least 10:1, more preferably at least 100:1, even more preferably at least 1000:1, even ratios of $10^5$:1 can be suitable.

Relative Arrangement of Regions

Depending on the specific embodiments, there can be various combinations of the inner region and the wall with the port region(s).

At least a portion of the port region(s) have to be in liquid communication with the inner region, so as to allow fluid to be transferred thereto.

The inner/bulk region should comprise larger pores than the wall region. The pore size ratio of inner pores to port region pores are preferably at least 3:1, more preferably at least 10:1, even more preferably at least 30:1 or even 100:1 and most preferable at least 350:1.

The area of the port regions will typically be as large or larger than the cross-section of the inner regions, thereby considering the respective regions together, namely—if present—the inlet regions or respectively the outlet regions. In most instance, the port regions will be twice as large as said inner region cross-section, often four times as large, or even 10 times as large.

Structural Relation of Regions

The various regions can have similar structural properties or different, possibly complementing, structural properties, such as strength, flexibility, and the like.

For example, all regions can comprise flexible material designed to cooperatively deform, whereby the inner region comprises a thin-until-wet material which expands upon contact with the transported liquid, the port region(s) comprise flexible membranes, and the walls can be made of liquid impermeable flexible film.

The liquid transport member can be made of various materials, whereby each region may comprise one or more materials.

For example, the inner region may comprise porous materials, the walls may comprise a film material, and the ports may comprise a membrane material.

Alternatively, the transport member may consist essentially of one material with different properties in various regions, such as a foam with very large pores to provide the functionality of the inner region, and smaller pores surrounding these with membrane functionality as port materials.

One way to look at a liquid transport member is to see the inner region being enclosed by at least one wall and/or port region. A very simple example for this is the above mentioned tube filled with liquid and closed by membranes at both ends, as indicated in FIG. 7.

Such members can be considered to be a "Closed Distribution Member", as the inner region (703) is "enclosed" by the wall region (702) comprising port regions (706, 707). It is characteristic for such systems, that—once the transport member is activated, or equilibrated—a puncturing of the wall region can interrupt the transport mechanism. The transport mechanism can be maintained if only a small amount of air enters the system. This small quantity of air can be accumulated in an area of the inner region wherein it is not detrimental to the liquid transport mechanism.

For the example of the hollow tube with at least one open port, puncturing the walls will result in immediate interruption of the liquid transport and fluid loss.

This mechanism can be exploited to define the "Closed System Test", (as described in the below), which is a "sufficient but not necessary" condition for liquid transport member according to the present invention (i.e. all transport members which satisfy this test can be considered to function within the principles of the present invention, but not all transport members which fail this test are outside the principle).

In a further embodiment as depicted in FIG. 8, the liquid transport member may comprise several inlet and/or several outlet port regions, for example as can be achieved by connecting a number of tubes (802) together and closing several end openings with inlet ports 806 and an outlet port 807, thereby circumscribing the inner region 803, or a "split" system where fluid is transported simultaneously to more than one location (more than one exit port). Alternatively, the transport to different locations may be selective (e.g., the voids in a transport material on the route to one port may be filled with a water soluble material, and the voids in the transport material on the route to a second port may be filled with an oil soluble material. Also, the transport medium may be hydro- and/or oleophilic to further enhance the selectivity.)

Figure 9A:
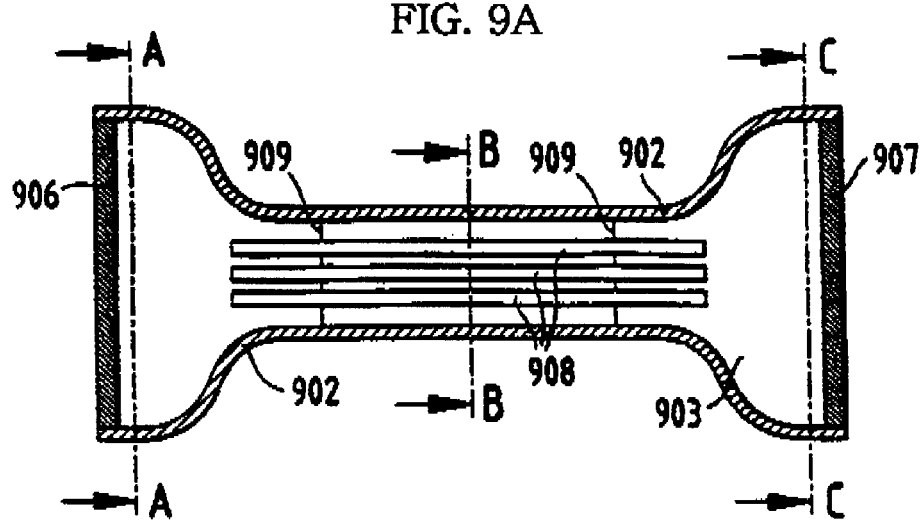
FIG. 9A: Schematic diagram of an embodiment of liquid transport member according to the present invention.
Figure 9C:
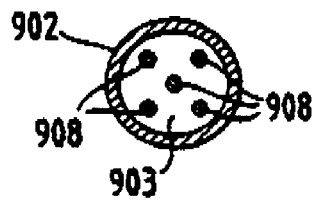
FIG. 9C: Schematic diagram of an embodiment of liquid transport member according to the present invention.
Figure 9B:
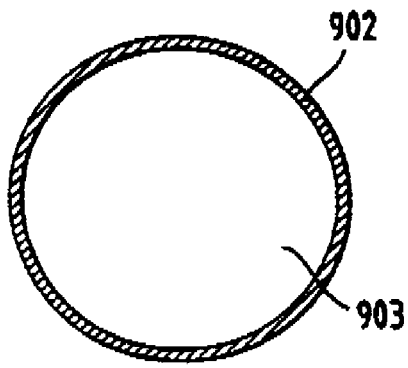
FIG. 9B: Schematic diagram of an embodiment of liquid transport member according to the present invention.
Figure 9D:
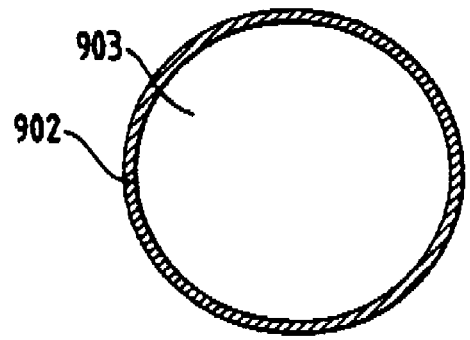
FIG. 9D: Schematic diagram of an embodiment of liquid transport member according to the present invention.

In yet a further embodiment as indicated in FIGS. 9A, B, C, and D, the inner region (903) can be segmented into more than one region, such as can be visualized by looking at a bundle of parallel pipes, held in position by any suitable fixation means (909), circumscribed by a wall region (902), comprising port regions (906, 907), and the inner separation means (908). It also can be contemplated, that at least some of the membrane material is placed inside the inner/bulk regions, and the membrane material can even form the walls of the pipes.

In an even further embodiment (FIG. 10), the wall region consists essentially of permeable port region, i.e., the inner region (1003) is not circumscribed by any impermeable region at all. The port region may have the same permeability, or can have a different degree of permeability, such as is indicated by regions (1006) and (1007). Thus the inner region may be wrapped by a membrane material, whereby the respective inlet and outlet port regions as part of the overall port region (1006 and 1007) can then be determined by the connection to sources/sinks, as more described for liquid transport systems. Also, the port region and the inner region can be connected by a gradual transition region, such that the transport member appears to be a unitary material with varying properties.

Figure 11A:
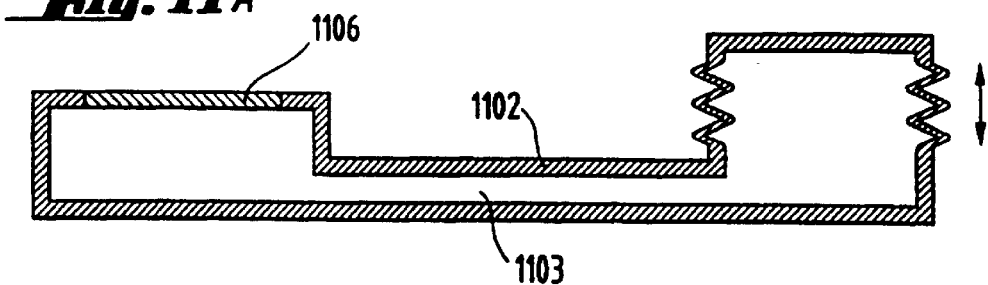
FIG. 11A: Schematic diagram of an embodiment of liquid transport member according to the present invention.
Figure 11B:
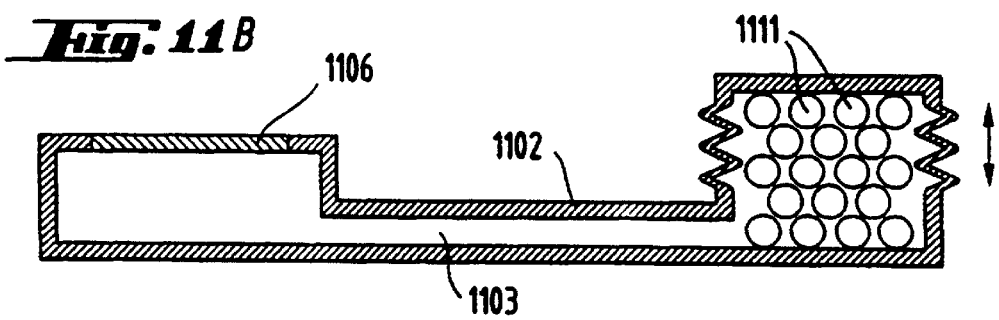
FIG. 11B: Schematic diagram of an embodiment of liquid transport member according to the present invention.
Figure 11C:
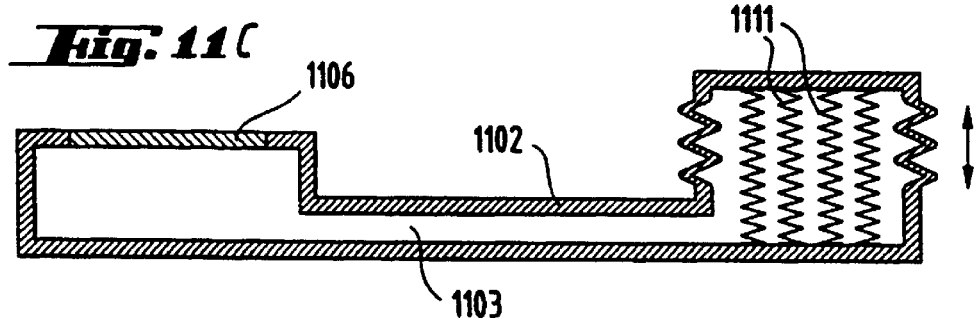
FIG. 11C: Schematic diagram of an embodiment of liquid transport member according to the present invention.
Figure 11D:
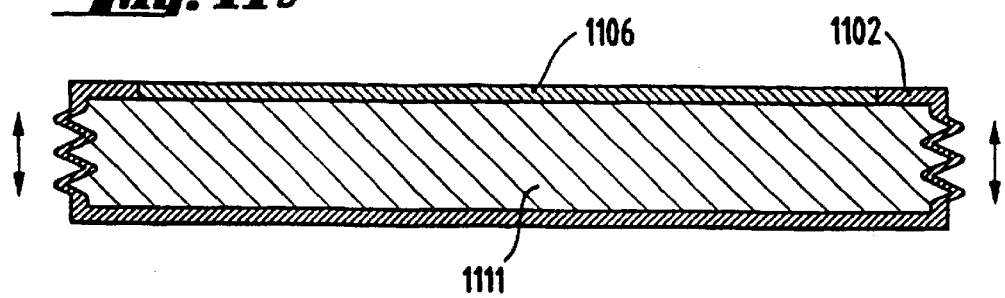
FIG. 11D: Schematic diagram of an embodiment of liquid transport member according to the present invention.

In further embodiments (FIGS. 11A, B, C, and D), the liquid transport member has one inlet port regions (1106) and one outlet port regions (1107). In addition to the transport functionality, such a member can receive and/or release liquid by having parts of the wall region (1102) deformable, such that the total member can increase the volume of the inner region (1103), so as to accommodate the additionally received volume of liquid, or so as to accommodate the initially contained liquid, which then can be released through the port region(s). Thus, in these members, a liquid sink or source can be integrally combined with the liquid transport member, and the liquid transport mernber can have a liquid sink or source integrally incorporated therein, such as depicted by elements (1111) in FIGS. 11B, C, and D.

For example structures made according to the teachings of U.S. Pat. No. 5,108,383 (White) disclosure can be considered as a liquid transport member according to the present invention if—and only if—these are modified according to the requirements for the bulk region and port regions as defined herein above. Because of the specific functioning mechanism, these structures otherwise miss the broad applicability of the present invention, which is—due to the additional requirements for the inner and port regions—not restricted to osmotic driving forces (i.e. the presence of promoters), nor do the membranes of the present invention have to satisfy the salt rejection properties required by the MOP structures according to U.S. Pat. No. 5,108,383.

A further embodiment can comprise highly absorbent materials such as superabsorbent materials or other highly absorbent materials as described in more detail in U.S. patent application Ser. No. 09/042429, filed Mar. 13, 1998 by T. DesMarais et al, which is incorporated herein by reference, combined with a port region made of a suitable membrane, and flexibly expandable walls to allow for an increase in the volume of the storage member. A further embodiment of such an system with a liquid sink integral with the liquid transport member, is a "Thin-until-wet" material in combination with a suitable membrane. Such materials are well known such as from U.S. Pat. No. 5,108,383, which are open celled porous hydrophilic foam materials, such as produced by High Internal Phase Emulsion process. The pore size, polymer strength (Glass Transition Temperature $T_g$) and the hydrophilic properties are designed such that the pores collapse when they are dewatered and at least partially dried, and expand upon wetting. A specific embodiment is a foam layer, which can expand its caliper upon absorption of liquid, and (re-) collapse upon removal of liquid.

Figure 12A:
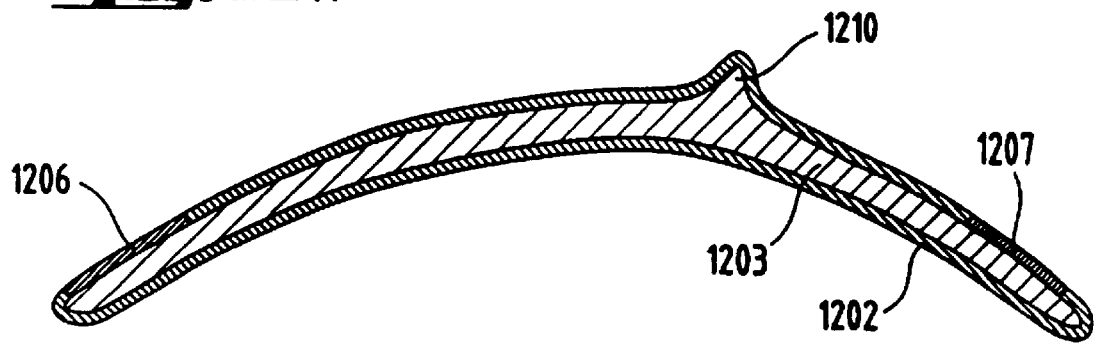
FIG. 12A: Schematic diagram of an embodiment of liquid transport member according to the present invention.
Figure 12B:
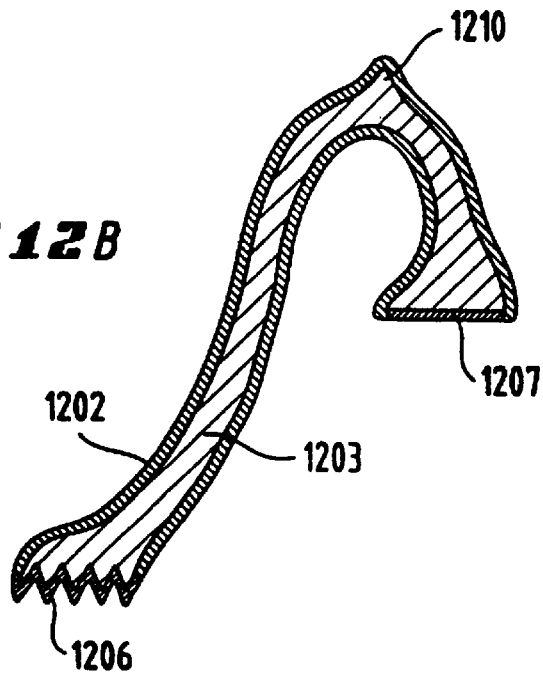
FIG. 12B: Schematic diagram of an embodiment of liquid transport member according to the present invention.

In even a further embodiment, the inner region can be void of liquid at the beginning of the liquid transport process (i.e. contains a gas at a pressure less than the ambient pressure surrounding the liquid transport member). In such cases, the liquid supplied by a liquid source can penetrate through the inlet port region(s) to first fill the voids of the membrane and then the inner region. The wetting then initiates the transport mechanisms according to the present invention thereby wetting, and penetrating the outlet port region. In such an instance, the inner regions may not be completely filled with the transport fluid, but a certain amount of residual gas or vapor may be retained. If the gas or vapor is soluble in the transported liquid, it is possible that after some liquid passes through the member, that substantially all of the initially present gas or vapor is removed, and the inner regions become substantially free of voids. Of course, in cases with some residual gas or vapor being present in the inner region, this may reduce the effective available cross-section of the fluid member, unless specific measures are taken, such as indicated in FIGS. 12A and B, with wall region (1202) comprising port regions (1206 and 1207) circumscribing the inner region (1203) and with region (1210) to allow gas to accumulate.

Yet another embodiment can use different types of fluid—for example, the member can be filled with an aqueous based liquid, and the transport mechanism is such, that a non-aqueous, possibly immiscible liquid (like oil) enters the liquid transport member via the inlet port while the aqueous liquid leaves the member via the outlet port.

In yet even further embodiments of the present invention, one or more of the above described embodiments can be combined.

Liquid Transport System

The following describes suitable arrangement of such a liquid transport member to create a suitable Liquid Transport System (LTS) according to the present invention.

A Liquid Transport System within the scope of the present invention comprises the combination of at least one liquid transport member with at least one further liquid sink or source in liquid communication with the member. A system can further comprise multiple sinks or sources, and also can comprise multiple liquid transport members, such as in a parallel functionality The latter can create a rundancy, so as to ensure functionality of the system, even if a transport member fails.

The source can be any form of free liquid or loosely bound liquid so as to be readily available to be received by the transport member.

For example a pool of liquid, or a freely flowing volume of liquid, or an open porous structure filled with liquid.

The sink can be any form of a liquid receiving region. In certain embodiments, it is preferred to have the liquid more tightly bound than the liquid in the liquid source. The sink can also be an element or region containing free liquid, such that the liquid would be able to flow freely or gravity driven away from the member. Alternatively, the sink can contain absorbent, or superabsorbert material, absorbent foams, expandable foams, alternatively it can be made of a spring activated bellows system, or it can contain osmotically functioning material, or combinations thereof.

Liquid communication in this context refers to the ability of liquids to transfer or to be transferred from the sink or source to the member, such as can be readily achieved by contacting the elements, or bringing the elements so closely together, that the liquid can bridge the remaining gap.

Such a liquid transport system comprises a liquid transport member according to the above description plus at least one liquid sink or source. The term at least applies to systems, where the liquid transport member itself can store or release liquids, such that a liquid transport system comprises a sink and a liquid releasing liquid transport member; or a source and a liquid receiving liquid transport member; or a sink and a source and a liquid transport member.

In each of these options, the liquid transport member can have liquid releasing or receiving properties in addition to a sink or source outside of the member. A system can further comprise multiple sinks or sources, and also can comprise multiple liquid transport members, such as in a parallel arrangement. The latter can create a rundancy, so as to ensure functionality of the system, even if an individual transport member fails.

At least a portion of the port region(s) must be in liquid communication with the source liquid and where applicable the sink material. One approach is to have the port region material form the outer surface of the liquid transport member, in part or as the whole outer surface, so as to allow liquids such as liquids of the liquid source or sink to readily contact the port regions. The effective port region size can be determined by the size of the liquid communication with the sink or source respectively. For example, the total of the port regions can be in contact with the sink or source, or only a part thereof. Alternatively, e.g., when there is one homogeneous port region, this can be distinguished into separate effective inlet port regions and effective outlet port regions where the port region is in contact with the liquid source and/or sink respectively.

It will be apparent, that a sink must be able to receive liquid from the member (and where applicable from the respective port regions), and a source must be able to release liquid to the member (and where applicable to the respective port regions).

Henceforth, a liquid source for a liquid transport member according to the present invention can be a free flowing liquid, such as urine released by a wearer, or a open water reservoir.

A liquid source region can also be an intermediate reservoir, such as a liquid acquisition member in absorbent articles.

Analogously, a liquid sink can be a free flow channel, or an expanding reservoir, e.g., a bellowed element combined with mechanical expansion or spacer means, such as springs.

A liquid sink region can also be an ultimate liquid storage element of absorbent members, such as being useful in absorbent articles and the like.

Figure 13A:
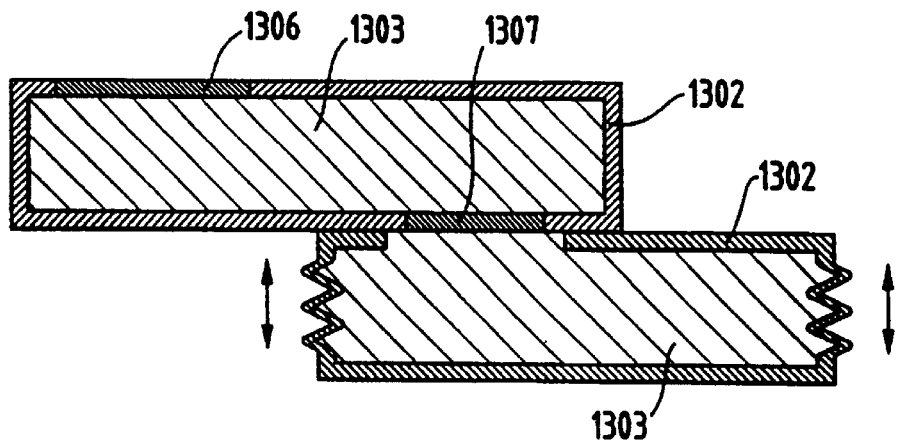
FIGS. 13A, B, C: Liquid Transport Systems according to the present invention.
Figure 13B:
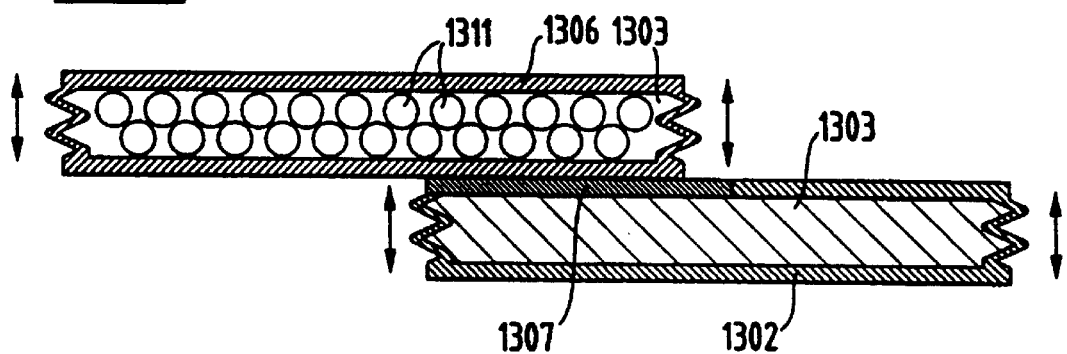
Figure 13C:
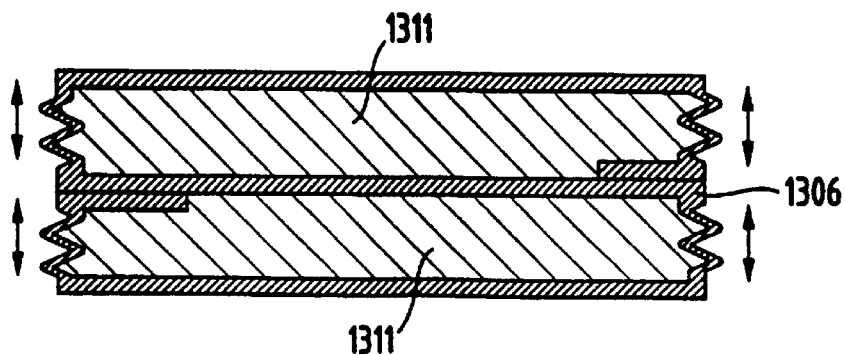

Two or more liquid transport systems according to the present invention can also be arranged in a "cascading design" (FIGS. 13A, B, C), with wall regions (1302), port regions (1306) and liquid sink materials (1311). Therein, the overall fluid flow path will go through one liquid transport system after the next. Thereby, the inlet port region of a subsequent liquid transport system can take over the sink functionality of a previous system, such as when the inlet and outlet port regions are in fluid communication with each other. Such a fluid communication can be direct contact, or can be via an intermediate material.

A specific embodiment of such a "cascade" can be seen in connecting two or more "membrane osmotic packets" comprising membranes of appropriate properties, whereby the osmotic suction power increases with subsequent packets. Each of the packets can then be considered a liquid transport member, and the connection between the packets will define the inlet and outlet port regions of each packet or member. Thereby, the packets can be enclosed by one material (such as one type of flexible membrane), or even several packets can have a unitary membrane element.

In a preferred embodiment, a liquid transport system has an absorption capacity of at least 5 g/g, preferably at least 10 g/g, more preferably at least 50 g/g and most preferably at least 75 g/g on the basis of the weight of the liquid transport system, when measured in the Demand Absorbency Test as described hereinafter.

In yet another preferred embodiment, the liquid transport system contains a sink comprising an absorbent material having an absorption capacity of at least 10 g/g, preferably at least 20 g/g and more preferably at least 50 g/g, on the basis of the weight of the sink material, when measured in the Teabag Centrifuge Capacity Test as described hereinafter.

In yet a further preferred embodiment, the liquid transport system comprises an absorbent material providing an absorbent capacity of at least 5 g/g, preferably at least 10 g/g, more preferably of at least 50 g/g or most preferably of at least 75 g/g up to the capillary suction corresponding to the bubble point pressure of the member, especially of at least 4 kPa, preferably at least 10 kPa, when submitted to the Capillary Sorption test as described herein. Such materials exhibit preferably a low capacity in the capsorption test above the bubble point pressure, such as 4 kPa or even 10 kPa, of less than 5 g/g, preferably less than 2 g/g, more preferably less than 1 g/g, and most preferably less than 0.2 g/g.

In certain specific embodiments, the liquid transport member can contain superabsorbent materials or foam made according to the High Internal Phase Emulsion polymerization, such as described in PCT application US98/05044. which is incorporated herein by reference.

Applications

There is a wide field for applying liquid transport members or systems according to the present invention. The following should not be seen to be limiting in any way, but rather to exemplify areas, where such members or systems are useful.

Suitable applications can be found for a bandage, or other health care absorbent systems. In another aspect, the article can be a water transport system or member, optionally combining transport functionality with filtration functionality, e.g. by purifying water which is transported. Also, the member can be useful in cleaning operation, so as by removing liquids or as by releasing fluids in a controlled manner. A liquid transport member according to the present invention can also be a oil or grease absorber.

One specific application can be seen in self-regulating irrigation systems for plants. Thereby, the inlet port can be immersed into a reservoir, and the transport member can be in the form of a long tube. In contrast to known irrigation systems (such as known under BLUMAT as available from Jade@ National Guild, PO Box 5370, Mt Crested Butte, Colo. 81225), the system according to the present invention will not loose its functionality upon drying of the reservoir, but remain functional until and after the reservoir is refilled.

A further application can be seen in air conditioning systems, with a similar advantage as described for the irrigation systems. Also, because of the small pore sizes of the port regions, this system would be easier to clean than conventional wetting aids, such as porous clay structures, or blotter paper type elements.

Yet a further application is the replacement of miniature pumps, such as can be envisaged in biological systems, or even in the medical field.

An even further application can be seen in selective transport of liquids, such as when aiming at transporting oil away from an oil/water mixture. For example, upon oil spillages on water, a liquid transport member can be used to transfer the oil into a further reservoir. Alternatively, oil can be transported into a liquid transport member comprising therein a sink functionality for oil.

An even further application uses the liquid transport member according to the present invention as a transmitter for a signal. In such an application, the total amount of transported liquid does not need to be very large, but rather the transport times should be short. This can be achieved, by having a liquid filled transport member, which upon receipt of even a little amount of liquid at the inlet port practically immediately releases liquid at the outlet port. This liquid can then be used to stimulate further reaction, such as a signal or activated a response, e.g., dissolving a seal to release stored mechanical energy to create a three dimensional change in shape or structure.

An even further application exploits the very short response times of liquid transport and practically immediate response time.

A particularly useful application for such liquid transport members can be seen in the field of absorbent articles, such as disposable hygiene articles, such as baby diapers or the like for disposable absorbent article.

Absorbent Articles—General Description

An absorbent article generally comprises:
an absorbent core or core structure (which may comprise the improved fluid transport members according to the present invention, and which may consist of additional sub-structures);
a fluid pervious topsheet;
a substantially fluid impervious backsheet;
optionally further features like closure elements or elastification.

FIG. 14 is a plan view of an exemplary embodiment of an absorbent article of the invention which is a diaper.

The diaper 1420 is shown in FIG. 14 in its flat-out, uncontracted state (i.e. with elastic induced contraction pulled out except in the side panels wherein the elastic is left in its relaxed condition) with portions of the structure being cut-away to more clearly show the construction of the diaper 1420 and with the portion of the diaper 1420 which faces away from the wearer, the outer surface 1452, facing the viewer. As shown in FIG. 14, the diaper 1420 comprises a containment assembly 1422 preferably comprising a liquid pervious topsheet 1424, a liquid impervious backsheet 1426 joined with the topsheet 1424, and an absorbent core 1428 positioned between the topsheet 1424 and the backsheet 1426; elasticized side panels 1430; elasticized leg cuffs 1432; an elastic waist feature 1434; and a closure system comprising a dual tension fastening system generally multiply designated as 1436. The dual tension fastening system 1436 preferably comprises a primary fastening system 1438 and a waist closure system 1440. The primary fastening system 1438 preferably comprises a pair of securement members 1442 and a landing member 1444. The waist closure system 1440 is shown in FIG. 14 to preferably comprise a pair of first attachment components 1446 and a second attachment component 1448. The diaper 1420 also preferably comprises a positioning patch 1450 located subjacent each first attachment component 1446.

The diaper 1420 is shown in FIG. 14 to have an outer surface 1452 (facing the viewer in FIG. 14), an inner surface 1454 opposed to the outer surface 1452, a first waist region 1456, a second waist region 1458 opposed to the first waist region 1456, and a periphery 1460 which is defined by the outer edges of the diaper 1420 in which the longitudinal edges are designated 1462 and the end edges are designated 1464. The inner surface 1454 of the diaper 1420 comprises that portion of the diaper 1420 which is positioned adjacent to the wearer's body during use (i.e. the inner surface 1454 generally is formed by at least a portion of the topsheet 1424 and other components joined to the topsheet 1424). The outer surface 1452 comprises that portion of the diaper 1420 which is positioned away from the wearer's body (i.e. the outer surface 1452 generally is formed by at least a portion of the backsheet 1426 and other components joined to the backsheet 1426). The first waist region 1456 and the second waist region 1458 extend, respectively, from the end edges 1464 of the periphery 1460 to the lateral centerline 1466 of the diaper 1420. The waist regions each comprise a central region 1468 and a pair of side panels which typically comprise the outer lateral portions of the waist regions. The side panels positioned in the first waist region 1456 are designated 1470 while the side panels in the second waist region 1458 are designated 1472. While it is not necessary that the pairs of side panels or each side panel be identical, they are preferably mirror images one of the other. The side panels 1472 positioned in the second waist region 1458 can be elastically extensible in the lateral direction (i.e. elasticized side panels 1430). (The lateral direction (x direction or width) is defined as the direction parallel to the lateral centreline 1466 of the diaper 1420; the longitudinal direction (y direction or length) being defined as the direction parallel to the longitudinal centreline 1467; and the axial direction (Z direction or thickness) being defined as the direction extending through the thickness of the diaper 1420).

FIG. 14 shows a specific of the diaper 1420 in which the topsheet 1424 and the backsheet 1426 have length and width dimensions generally larger than those of the absorbent core 1428. The topsheet 1424 and the backsheet 1426 extend beyond the edges of the absorbent core 1428 to thereby form the periphery 1460 of the diaper 1420. The periphery 1460 defines the outer perimeter or, in other words, the edges of the diaper 1420. The periphery 1460 comprises the longitudinal edges 1462 and the end edges 1464.

While each elasticized leg cuff 1432 may be configured so as to be similar to any of the leg bands, side flaps, barrier cuffs, or elastic cuffs described above, it is preferred that each elasticized leg cuff 1432 comprise at least an inner barrier cuff 1484 comprising a barrier flap 1485 and a spacing elastic member 1486 such as described in the above-referenced U.S. Pat. No. 4,909,803. In a preferred embodiment, the elasticized leg cuff 1432 additionally comprises an elastic gasketing cuff 14104 with one or more elastic strands 14105, positioned outboard of the barrier cuff 1484 such as described in the above-references U.S. Pat. No. 4,695,278.

The diaper 1420 may further comprise an elastic waist feature 1434 that provides improved fit and containment. The elastic waist feature 1434 at least extends longitudinally outwardly from at least one of the waist edges 1483 of the absorbent core 1428 in at least the central region 1468 and generally forms at least a portion of the end edge 1464 of the diaper 1420. Thus, the elastic waist feature 1434 comprises that portion of the diaper at least extending from the waist edge 1483 of the absorbent core 1428 to the end edge 1464 of the diaper 1420 and is intended to be placed adjacent the wearer's waist. Disposable diapers are generally constructed so as to have two elastic waist features, one positioned in the first waist region and one positioned in the second waist region.

The elasticized waist band 1435 of the elastic waist feature 1434 may comprise a portion of the topsheet 1424, a portion of the backsheet 1426 that has preferably been mechanically stretched and a bi-laminate material comprising an elastomeric member 1476 positioned between the topsheet 1424 and backsheet 1426 and resilient member 1477 positioned between backsheet 1426 and elastomeric member 1476.

This as well as other components of the diaper are given in more detail in WO 93/16669 which is incorporated herein by reference.

Absorbent Core

The absorbent core should be generally compressible, conformable, non-irritating to the wearers skin, and capable of absorbing and retaining liquids such as urine and other certain body exudates. As shown in FIG. 14, the absorbent core has a garment surface a body surface, side edges, and waist edges. The absorbent core may—in addition to the liquid transport member according to the present invention—comprise a wide variety of liquid-absorbent or liquid handling materials commonly used in disposable diapers and other absorbent articles such as—but not limited to—comminuted wood pulp which is generally referred to as airfelt; meltblown polymers including conform; chemically stiffened, modified or cross-linked cellulosic fibers; tissue including tissue wraps and tissue laminates.

General examples for absorbent structures are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; EP-A-0 640 330 of Bewick-Sonntag et al.; U.S. Pat. No. 5,180,622 (Berg et al.); U.S. Pat. No. 5,102,597 (Roe et al.); U.S. Pat. No. 5,387,207 (Dyer et al.). Such and similar structures might be adapted to be compatible with the requirements outlined below for being used as the absorbent core.

The absorbent core can be a unitary core structure, or it can be a combination of several absorbent structures, which in turn can consist of one or more sub-structures. Each of the structures or sub-structures can have an essentially two-dimensional extension (i.e. be a layer) or a three-dimensional shape.

The liquid transport member according to the present invention can comprise at least one inlet port region, which should be located in the loading zone of the article. This port region can be made from flexible membrane material satisfying the requirements as described herein, which can be connected to a high resiliency, open fibrous structure forming the inner region, which can be wrapped in flexible impermeable films to form the wall regions which can be adhesively closed at all edges except for the port region. In order to allow good overall sealing, the impermeable film can overlap the port region somewhat so as to allow also adhesive bonding there between.

Figure 15:
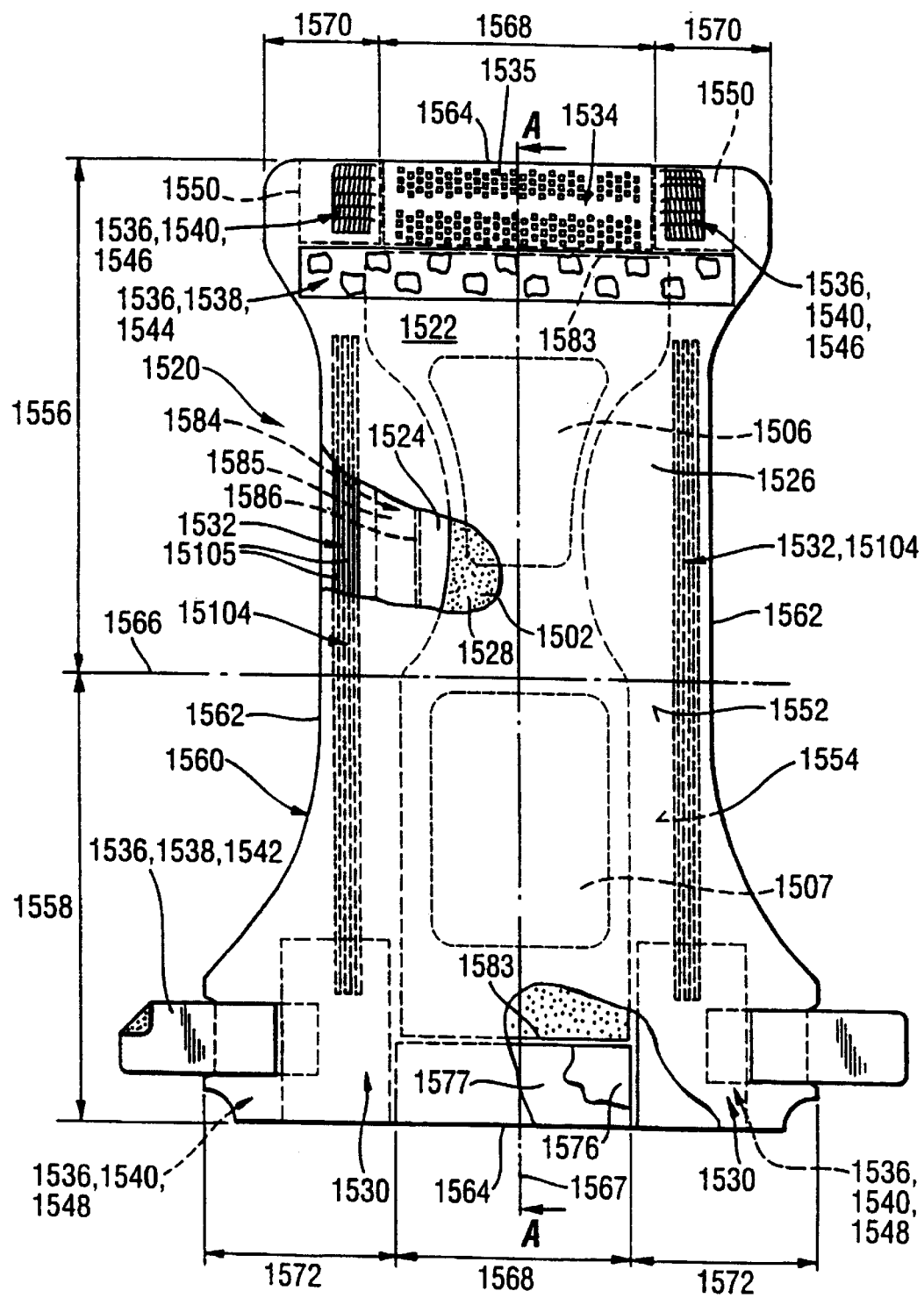
FIGS. 15 to 16A, B: Absorbent Article comprising a liquid transport member.
Figure 16B:
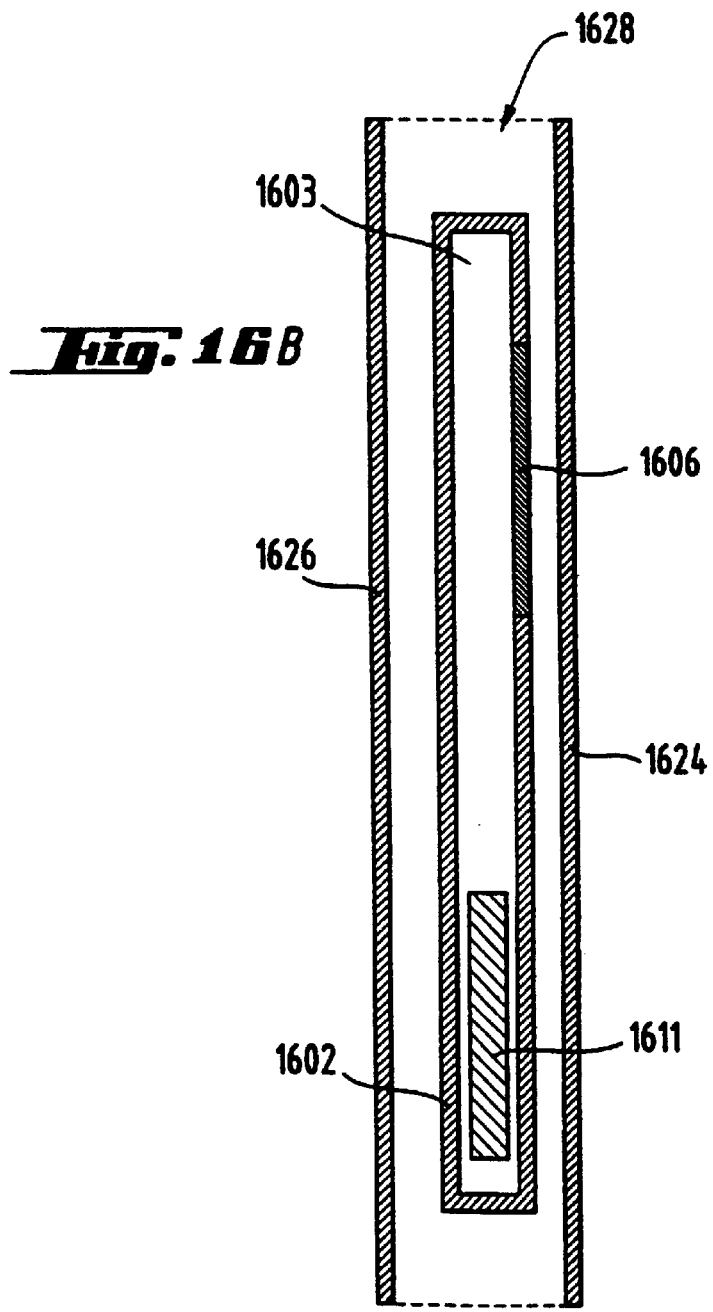

FIG. 15 shows a specific embodiment of an article as shown in FIG. 14,—with analogous numerals—and FIG. 16 shows a partly exploded simplified cross-sectional view along A—A of FIG. 15, again with analogous numbering. Therein, an absorbent core (1528/1628) is made of suitable liquid handling member which is constructed from a wall region (1502,1602), port regions (1506, 1507, 1606, 1607), and inner region (1503, 1603). The member may be connected to a liquid sink (1511, 1611), and optionally a topsheet (1512, 1612) is attached. The sink (1511, 1611) can comprise ultimate storage material, such as superabsorbent material, or highly absorbing porous material.

The inner regions can be filled with liquid, such as water, so as to be ready for liquid transport there through immediately after receipt of the liquid at the inlet port. Alternatively, the inner region can be under a vacuum, which can suck in liquid through the inlet port such as upon activation of a barrier film like a polyvinyl alcohol film which can dissolve upon wetting. Once the inner region is filled with liquid, and thus also the outlet port region becomes wetted by the liquid, the transport mechanism as for a pre-filled system takes place.

The absorbent core can be designed so as to not require any further fluid handling element.

For example, the area of the inlet port region can be adjusted to its permeability and caliper so as to enable the port region to immediately acquire the liquid at the gush rate, and the inner region can be adjusted by its permeability and cross-sectional area so as to immediately transmit the liquid to the ultimate storage region.

Alternatively, the absorbent core may comprise other fluid handling elements, such as acquisition regions, or interim storage regions, or the like. Also, the "cascading liquid transport member" or "MOP" can be suitable elements within the core construction.

Method of Making Liquid Transport Members

The liquid transport members according to the present invention can be produced by various methods, which have to have in common the essential steps of combining a bulk or inner region with a wall region comprising port regions with appropriate selection of the respective properties as described in the above. This can be achieved by starting from a homogeneous material, and imparting therein different properties. For example, if a member is a polymeric foam material, this can be produced form one monomer with varying pore sizes, which will then be polymerized to form a suitable member.

This can also be achieved by starting from various essentially homogeneous materials and combining these into the a member. In this execution, a wall material can be provided, which may have homogeneous or varying properties, and a bulk material can be provided, which can be open porous material, or a void space can be defined to represent the bulk region. The two materials can the be combined by suitable techniques, such as by wrapping or enveloping as well known in the art, such that the wall material completely circumscribes the bulk region or bulk region material.

In order to enable liquid transport, the bulk region can be filled with liquid, or can be subjected to vacuum, or can be equipped with other aids so as to created vacuum, or liquid filling.

Optionally, the method of forming a member according to the present invention can comprise the step of applying activation means, which can be of the mechanical type, such as by providing a removable release element, such as being well known for example as a release paper for covering adhesives, or by providing a packaging design which allows the sealing of the member until use, whereby at the time of use such a packaging sealing is removed or opened. This activation means can also comprise materials which react upon the transport liquid, such as dissolve. Such materials may be applied in the port regions, e.g. to open the port regions upon use, or such materials may be applied to the bulk regions, such as to allow expansion of these regions upon wetting.

The making of members according to the present invention can be done in an essentially continuous way, such as by having various materials provided in roll form, which are then unwound and processed, or any of the materials can be provided in discrete form, such as foam pieces, or particulates.

EXAMPLES

The following section provides specific suitable examples for liquid transport members and systems according to the present invention, thereby starting by describing various samples suitable for being used in certain regions of these members or systems.

S-1 Samples Suitable for Port Regions:

S-1.1:—Woven filter mesh HIFLO®, type 20 such as available from Haver & Boecker, Oelde, Germany, made from stainless steel, having at a porosity of 61%, and a caliper of 0.09 mm, designed for filtering down to 19 $\mu$m to 20 $\mu$m.

S-1.2a:—Polyamide mesh Monodur Type MON PA 20 N such as available from Verseidag in Geldern-Waldbeck, Germany.

S-1.2b: Polyamide mesh Monodur Type MON PA 42.5 N such as available from Verseidag in Geldern-Waldbeck, Germany.

S-1.3a: Polyester mesh such as 07-20/13 of SEFAR in Rüschlikon, Switzerland.

S-1.3b: Polyamide mesh 03-15/10 of SEFAR in Rüschlikon, Switzerland.

S-1.3c: Polyamide mesh 03-20/14 of SEFAR in Rüschlikon, Switzerland.

S-1.3d: Polyamide mesh 03-1/1 of SEFAR in Rüschlikon, Switzerland.

S-1.3e: Polyamide mesh 03-5/1 of SEFAR in Rüschlikon, Switzerland.

S-1.3f: Polyamide mesh 03-10/2 of SEFAR in Rüschlikon, Switzerland.

S-1.3g: Polyamide mesh 03-11/6 of SEFAR in Rüschlikon, Switzerland.

S-1.4: Cellulose acetate membranes such as described in U.S. Pat. No. 5,108,383 (White, Allied-Signal Inc.).

S-1.5: HIPE foam produced according to the teachings of U.S. patent application Ser. No. 09/042429, filed Mar. 13, 1998 by T. DesMarais et al. titled "High Suction polymeric foam", the disclosure of which is incorporated herein by reference.

S-1.6: Nylon Stockings e.g. of 1.5 den type, commercially available in Germany, such as from Hudson.

S-2 Samples Suitable for Wall Regions Not Representing Port Regions

S-2.1: Flexible adhesive coated film, such as commercially available under the trade name "d-c-fix" from Alkor, Gräfelfing, Germany.

S-2.2: Plastic funnel Catalog # 625 617 20 from Fisher Scientific in Nidderau, Germany.

S-2.3: Flexible tubing (inner diameter about 8 mm) such as Masterflex 6404–17 by Norton, distributed by the Barnant Company, Barrington, Ill. 60010 U.S.A.

S-2.4: Conventional polyethylene film such as used as backsheet material in disposable diapers, such as available from Clopay Corp., Cincinnati, Ohio, US, under the code DH-227.

S-2.5: Conventional polyethylene film such as used as backsheet material in disposable diapers, such as available from Nuova Pansac SpA in Milano, Italy under the code BS code 441118.

S-2.6: Flexible PVC tube e.g. Catalog #620 853 84 from Fisher Scientific in Nidderau, Germany.

S-2.7: PTFE Tube e.g. Catalog # 620 456 68 from Fisher Scientific in Nidderau, Germany.

S-3 Samples Suitable Inner Region

S-3.1: Void as created by any stiff wall/port region.

S-3.2: Metallic springs having a outer diameter of 4 mm and a length of about 6 cm with any applied force, as available from FedeCfabrik Dietz in Neustadt, Germany under the designation "fedem" article #DD/100.

S-3.3: Open cell foams from Recticel in Brussels, Belgium such as Filtren TM10 blue, Fiatren TM20 blue, Filtren TM30 blue, Filtren Firend 10 black, Filtren Firend 30 black, Filtren HC 20 grey, Filtren Firend HC 30 grex, Buopren S10 black, Bulpren S20 black, BuGpren S30 black).

S-3.4: HIPE foams as produced according to the teachings of U.S. patent application Ser. No. 09/042418, filed Mar. 13 1998 by T. DesMarais et al. ,titled "Absorbent Materials For Distributing Aqueous Liquids", the disclosure of each of which is incorporated by reference herein.

S-3.5: Particulate pieces of S-3.4 or S-3.3.

S-4 Samples for Pressure Gradient Creation Means

S-4.1: Osmotic pressure gradient materials according to the teachings of U.S. Pat. No. 5,108,383 (White, Allied Signal).

S-4.2: Height difference between inlet and outlet generating a hydrostatic height generated pressure difference.

S-4.3: Various partially saturated porous materials (Absorbent foams, superabsorbent materials, particles, sand, soils) generating a capillary pressure difference.

S-4.4: Difference in air pressure at the inlet and the outlet as e.g. generated by a vacuum pump (airtight sealed) to the outlet.

Example A for Transport Member

Combination of wall region with port region, inner region filled with liquid:

A-1) A ca 20 cm long tube (S-2.6) is connected in an air tight way with a plastic funnel (S-2.2). Sealing can be made with Parafilm M (available from Fischer Scientific in Nidderau, Germany catalog number 617 800 02). A circular piece of port material (S-1.1), slightly larger than the open area of the funnel is sealed in an air tight way with the funnel. Sealing is made with suitable adhesive, e.g., Pattex™ of Henkel KGA, Germany.

Optionally a port region material (S-1.1) may be connected to the lower end of the tube and be sealed in a air tight way. The device is filled with a liquid such as water by putting it under the liquid and removing the air inside the device with a vacuum pump tightly connected to the port region. In order to demonstrate the functionality of a member, the lower end does not need to be sealed with a port region, but then the lower end needs to be in contact with the liquid or needs to be the lowest part of the device in order to not allow air to enter the system.

A-2) Two circular (e.g. of a diameter of about 1.2 cm) port region materials as in S-1.1 are sealed in an air tight way (e.g. by heating the areas intended to become the port regions and pressing the ends of S-2.3 onto these areas, such that the plastic material of S-2.3 starts melting, thereby creating a good connection) at the two ends of a ca 1 m long tube as the one of S-2.3. One end of the tube is dropped into the liquid such as water, the other end is connected to a vacuum pump creating an air pressure substantially smaller than atmospheric pressure. The vacuum pump draws air from the tube until effectively all air is removed from the tube and replaced by the liquid. Then the pump is disconnected from the port and thus the member is created.

A-3) A ca 10 cm×10 cm rectangular sheet of foam material (S-3.3, Filtren TM 10 blue) "sandwiched" on one side by a wall material as S-2.5 of dimensions ca 12 cm×12 cm, on the other side by a port region material of dimensions ca 12 cm×12 cm as S-1.3a. The wall material S-2.5 and the port region material S-1.3a are sealed together in the overlap region in a convenient air tight way, e.g., by gluing with the above mentioned commercially available Pattex™ adhesive of Henkel KGA, Germany. The device is immersed under a liquid such as water, and by squeezing the device, air is forced out. Releasing squeezing pressure from the device whilst keeping it under liquid, the inner region is filled with liquid. Optionally (if necessary) a vacuum pump can suck the remaining air inside the device through the port region while the device is under water.

A-4) FIGS. 17 A, B schematically shows a distribution member, suitable for example for absorbent articles, such as a disposable diapers.

The inlet port region (1706) is made of port region material such as S-1.3a, the outlet port region (1705) is made of port region material such as S-1.3c. In combination with an impermeable film material (1702) such as S-2.3 or S-2.4, each of the port regions forms a pouch, which can have dimensions of about 10 cm by 15 cm for the inlet port region respectively 20 cm by 15 cm for the outlet port region. The port materials of the pouches overlap in the crotch region (1790) of the article, and a tube (1760) is positioned therein.

The inner regions within the pouches (1740, 1750) can be S-3.3 (Filtren TM10 blue), and the inlet and outlet regions respectively inner regions enclosed by them, can be connected by tubes (1760) such as S-2.6 of an inner diameter of about 8 mm.

Wall and port material (1702, 1707, 1706) must be sufficiently larger than the inner material to allow airtight sealing of wail material to port material. Sealing is done by overlapping of a ca 1.5 cm wide stripe of wall and port material and can be done in any convenient air tight way e.g. by using the above mentioned Pattex™ adhesive. Sealing of the tubes to the inner regions (1740 and 1750) is not required, if the tube (1760) is attached to the wall regions (1702, 1706, 1705) such that the distance between the tubing (1760) and the inner regions is such that a void space will be maintained therebetween during use. The rest of the operation to create a functioning liquid distribution member is also analogous to A-3. Optionally the device can be filled with other liquids in a similar fashion.

Figure 18A:
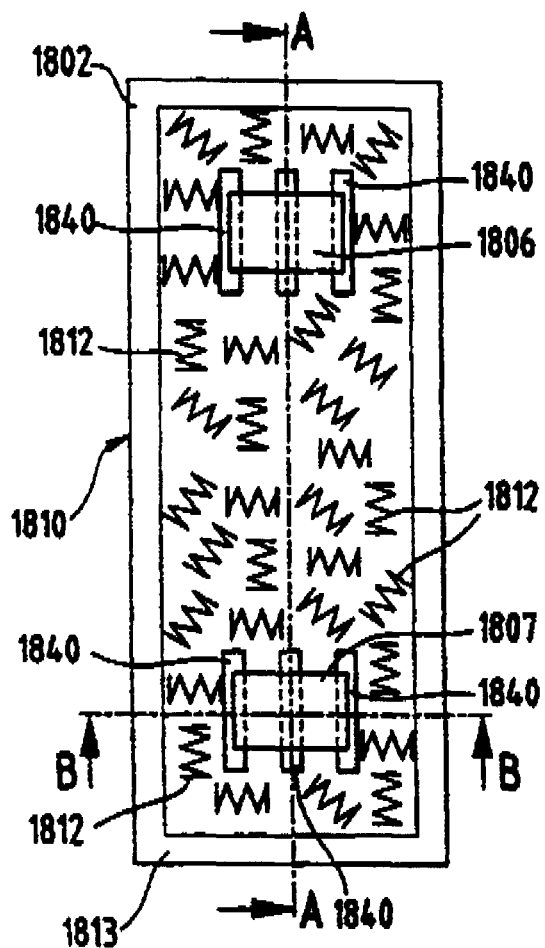
Figure 18B:
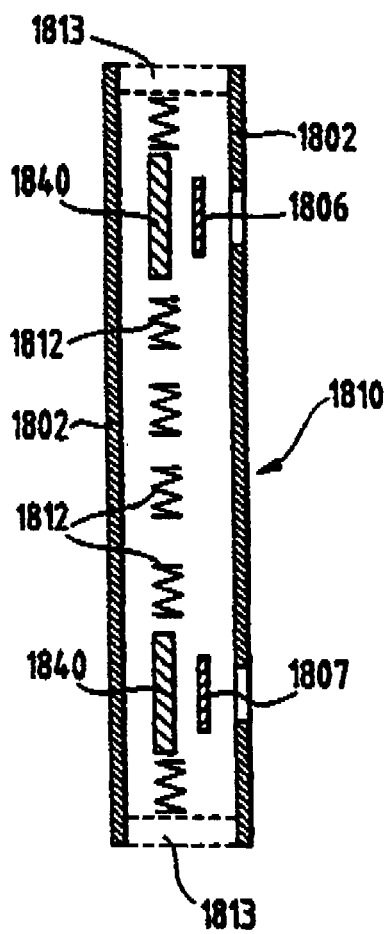
Figure 18C:
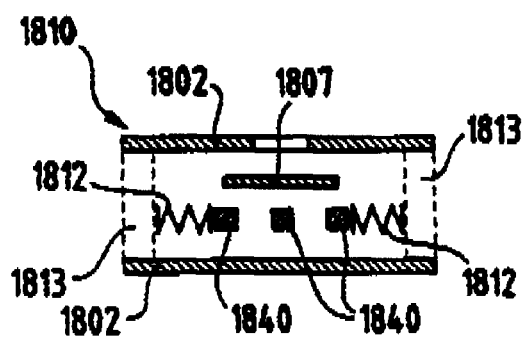

A5) In FIGS. 18 A, B, C, a further example for a liquid distribution member (1810), also useful for construction of disposable absorbent articles, such as diapers, is schematically depicted, omitting other elements such as adhesives and the like.

Therein, inlet (1806) and outlet port (1807) regions having a dimension of about 8 cm by 12 cm are made from sheets of port material S-1.2a, the other wall regions are made of wall material S-2.1. Inner material (1840) are stripes of material S-3.3 (Bulpren S10 black) having dimension of about 0.5 cm by 0.5 cm by 10 cm, placed at a distance of about 1 cm to each other, under the inlet and outlet regions (1806, 1807 respectively) and spacer springs S-3.2 (1812) in the remaining areas. Individual layers (wall and port material) are sealed and further filled with a liquid such as water as described in A-3. Optionally the device can be filled with other liquids in a similar fashion.

A6) Spacer materials such as springs according to S-3.2 are positioned between an upper and a lower sheet of port material S-1.2b, having a dimension of 10 cm by 50 cm, such that the springs are equally distributed over the area in a region of about 7 cm times 47 cm leaving the outer rim of about 1.5 cm free of springs, with a distance of about 2 mm between the individual springs. Upper and lower port material are sealed in an air tight way by overlapping ca 1.5 cm and sealing in a convenient air tight way such as by gluing with the above mentioned Pattex™ adhesive. The device is immersed under the testing liquid, by squeezing the device air is forced to leave the interior of the device. Releasing the squeezing pressure while being immersed, the member will be filled with liquid. Optionally (if necessary) a vacuum pump can suck the remaining air from inside the member through the port region while the device is under the liquid.

Example B for Transport System (i.e. Member and (Source and/or Sink))

B-1) As a first example for a liquid transport system, a liquid transport member according to A-1) is combined with particulate superabsorbent material, such a available under the designation W80232 from HÜLS-Stockhausen GmbH, Marl, Germany, with coarse particles being removed by sieving through a 300 im metal sieve. 7.5 g of this material have been evenly sprinkled over the outlet port region of A-1, thereby creating a liquid sink.

B-2) To exemplify the use of absorbent foam materials to create an absorbent system, a sheet of three layers of HIPE foam produced as for S-1.5 each having a thickness of about 2 mm, and a corresponding basis weight of about 120 g/m$^2$ are positioned on the outlet port of a liquid transport member according to A-1. The sheets were cut circular with a diameter of about 6 cm, and a segment of about 10° was cut out to provide better conformity to the port region surface. Optionally a weight corresponding to a pressure of about 0.2 psi can be applied to enhance liquid contact between outlet and sink material.

B-3) The liquid transport member according to A-1 has been combined with a circular cut out section of ca 6 cm diameter taken from a commercially available diaper core, consisting of a essentially homogeneous blend of superabsorbent material such as ASAP2300 commercially available from CHEMDAL Corp. UK, and conventional airfelt at a 60% by weight superabsorber concentration and a basis weight of the superabsorbent of about 400 g/m$^2$). This cut out is placed in liquid communication with the outlet port region of A-1 to create a liquid transport system.

B-4) To further exemplify an application of a liquid transport system, the liquid transport member of A-2 has been positioned between a liquid source reservoir and a flower pot, such that a portion of the inlet port region is immersed in the liquid reservoir, and the outlet port being put into the soil of the flower pot. The relative height of the reservoir and the flower pot is of no relevance for this length of the member, and would not be up to a length of the member of about 50 cm.

B-5) A further application of a liquid transport system with an integral liquid sink which can be constructed by creating a liquid transport member as in A-3, but filling it with oil (instead of water). When squeezing the member (so as to create expanding voids within the member), and immediately thereafter contacting it with cooking oil (so as to simulate a kitchen frying pan), the system will rapidly absorb the oil in the pan.

B-6) When combining a liquid transport member according to A-4 or A-5 with a liquid sink such as used in B-1 or B-2, optionally covering the sink material by a containment layer, such as a non-woven web, the structure can function as a absorbent pad, whereby the urine as released by the wearer can be seen to provide the liquid source.

METHODS

Activation

As the properties which are relevant for the liquid handling ability of a liquid transport member according to the present invention are considered at the time of liquid transport, and as some of the materials or designs might have properties which differ from these, for example to ease transport or other handling between manufacturing of the member and its intended use, such members should also be activated before they are submitted to a test.

The term "activation" means, that the member is put into the in use condition, such as by establishing a liquid communication along a flow path, or such as by initiating a driving pressure differential, and this can be achieved by mechanical activation simulating the pre-use activation of a user (such as the removal of a constraining means such as a clamp, or a strip of a release paper such as with an adhesive, or removal of a package seal, thereby allowing mechanical expansion optionally with creation of a vacuum within the member).

Activation can further be achieved by another stimulus transmitted to the member, such as pH or temperature change, by radiation or the like. Activation can also be achieved by interaction with liquids, such as having certain solubility properties, or changing concentrations, or are carrying activation ingredients like enzymes. This can also be achieved by the transport liquid itself, and in these instances, the member should be immersed in testing liquid which should be representative for the transport liquid, optionally removing the air by means of a vacuum pump, and allowing equilibration for 30 minutes. Then, the member is removed from the liquid, a put on a coarse mesh (such as a 14 mesh sieve) to allow dripping off of excess liquid.

Closed System Test

Principle:

The test provides a simple to execute tool to assess if a transport material or member satisfies the principles of the present invention. It should be noted, that this test is not useful to exclude materials or members, i.e. if a material or members does not pass the Closed System Test, it may or may not be a liquid transport member according to the present invention.

Execution:

First, the test specimen is activated as described herein above, whilst the weight is monitored. Then, the test specimen is suspended or supported in a position such that the longest extension of the sample is essentially aligned with the gravity vector. For example, the sample can be supported by a support board or mesh arranged at an angle of close to 90° to the horizontal, or the sample can be suspended by straps or bands in a vertical position.

As a next step, the wall region is opened in the uppermost and in the lowermost parts of the sample, i.e., if the sample has opposite corners, then at these corners, if the sample has a curved or rounded periphery, then at the top and bottom of the sample. The size of the opening has to be such as to allow liquid passing through the lower opening and air passing through the upper opening without adding pressure or squeezing. Typically, an opening having an inscribed circular diameter of at least 2 mm is adequate.

The opening can be done by any suitable means, such as by using a pair of scissors, a clipping tongue, needle, a sharp knife or a scalpel and the like. If a slit is applied to the sample, it should be done such that the flankes of the slit can move away from each other, so as to create a two-dimensional opening. Alternatively, a cut can remove a part of the wall material thus creating an opening.

Care should be taken that no additional weight is added, or pressure or squeezing is exerted on the sample. Similarly, care should be take, that no liquid is removed by the opening means, unless this could be accurately considered when calculating the weight differences.

The weight thereof is being monitored (such as by catching the liquid in a Petri dish, which is put on a scale). Alternatively, the weight of the material or member can be determined after 10 minutes and compared to the initial weight.

Care should be taken, that no excessive evaporation takes place, if this would be the case, this can be determined by monitoring the weight loss of a sample without having it opened over the test time, and by then correcting the results accordingly.

If the dripping weight is more than or equal to 3% of the initial liquid weight, then the tested material or member has passed this test, and is a liquid transport member according to the present invention.

If the dripping weight is less than 3% of the initial total weight, then this test does not allow assessment whether the material is a liquid transport member according to the present invention or not.

Bubble Point Pressure (Port Region)

The following procedure applies when it is desired to asses the bubble point pressure of a port region or of a material useful for port regions.

First, the port region respectively the port region material is connected with a funnel and a tube as described in example A-1. Thereby, the lower end of the tube is left open i.e. not covered by a port region material. The tube should be of sufficient length, i.e. up to 10 m length may be required.

In case the test material is very thin, or fragile, it can be appropriate to support it by a very open support structure (as e.g. a layer of open pore non-woven material) before connecting it with the funnel and the tube. In case the test specimen is not of sufficient size, the funnel may be replaced by a smaller one (e.g. Catalog # 625 616 02 from Fisher Scientific in Nidderau, Germany). If the test specimen is too large size, a representative piece can be cut out so as to fit the funnel.

The testing liquid can be the transported liquid, but for ease of comparison, the testing liquid should be a solution 0.03% TRITON X-100, such as available from MERCK KGaA, Darmstadt, Germany, under the catalog number 1.08603, in destined or deionized water, thus resulting in a surface tension of 33 mN/m, when measured according to the surface tension method as described further.

The device is filled with testing liquid by immersing it in a reservoir of sufficient size filled with the testing fluid and by removing the remaining air with a vacuum pump.

Whilst keeping the lower (open) end of the funnel within the liquid in the reservoir, the part of the funnel with the port region is taken out of the liquid. If appropriate—but not necessarily—the funnel with the port region material should remain horizontally aligned.

Whilst slowly continuing to raise the port material above the reservoir, the height is monitored, and it is carefully observed through the funnel or through the port material itself (optionally aided by appropriate lighting) if air bubbles start to enter through the material into the inner of the funnel. At this point, the height above the reservoir is registered to be the bubble point height.

From this height H the bubble point pressure bpp is calculated as: $BPP = \rho \cdot g \cdot H$ with the liquid density $\rho$, gravity constant g ($g \sim 9.81$ m/s$^2$).

In particular for bubble point pressures exceeding about 50 kPa, an alternative determination can be used, such as commonly used for assessing bubble point pressures for membranes used in filtration systems.

Therein, the wetted membrane is separating two gas filled chambers, when one is set under an increased gas pressure (such as an air pressure), and the point is registered when the first air bubbles "break through". Alternatively, the PMI permeater or porosity meter, as described in the test method section hereinafter, can be used for the bubble point pressure determination.

Bubble Point Pressure (Liquid Transport Member)

For measuring the bubble point pressure of a liquid transport member (instead of a port region or a port region material), the following procedure can be followed.

First, the member is activated as described above. The testing liquid can be the tranported liquid, but for ease of comparison, the testing liquid should a solution 0.03% TRITON X-100, such as available from MERCK KGaA, Darmsatdt, Germany, under the catalog number 1.08603, in destined or deionized water, thus resulting in a surface tension of 33 mN/m, when measured according to the surface tension method as described further.

A part of a port region under evaluation is connected to a vacuum pump connected by a tightly sealed tube/pipe (such as with Pattex™ adhesive as described above).

Care must be taken, that only a part of the port region is connected, and a further part of the region next to the one covered with the tube is still uncovered and in contact with ambient air.

The vacuum pump should allow to set various pressures $P_{vac}$, increasing from atmospheric pressure $P_{atm}$ to about 100 kPa. The set up (often integral with the pump) should allow monitoring the pressure differential to the ambient air ($\Delta p = P_{atm} - P_{vac}$) and of the gas flow.

Then, the pump is started to create a light vacuum, which is increased during the test in a stepwise operation. The amount of pressure increase will depend on the desired accuracy, with typical values of 0.1 kPa providing acceptable results.

At each level, the flow will be monitored over time, and directly after the increase of $\Delta p$, the flow will increase primarily because of removing gas from the tubing between the pump and the membrane. This flow will however, rather quickly level off, and upon establishing an equilibrium $\Delta p$, the flow will essentially stop. This is typically reached after about 3 minutes.

This step change increase is continued up to the break through point, which can be observed by the gas flow not decreasing after the step change of the pressure, but remaining after reaching an equilibrium level essentially constant over time.

The pressure $\Delta p$ one step prior to this situation is the bpp of the liquid transport member.

For materials having bubble point pressures in excess of about 90 kPa, it will be advisable or necessary to increase the ambient pressure surrounding the test specimen by a constant and monitored degree, which is the added to $\Delta p$ as monitored.

Surface Tension Test Method

The surface tension measurement is well known to the man skilled in the art, such as with a Tensiometer K10T from Krüss GmbH, Hamburg, Germany using the DuNouy ring method as described in the equipment instructions. After cleaning the glassware with iso-propanol and de-ionized water, it is dried at 105° C. The Platinum ring is heated over a Bunsen-burner until red heat. A first reference measurement is taken to check the accuracy of the tensiometer. A suitable number of test replicates is taken to ensure consistency of the data. The resulting surface tension of the liquid as expressed in units of mN/m can be used to determine the adhesion tension values and surface energy parameter of the respective liquid/solid/gas systems. Destilled water will generally exhibit a surface tension value of 72 mN/m, a 0.03% X-100 solution in water of 33 mN/m.

Liquid Transport Test

The following test can be applied to liquid transport members having defined inlet and outlet port regions with a certain transport path length $H_0$ between inlet and outlet port regions. For members, where the respective port regions cannot be determined such as because they are made of one homogeneous material, these regions may be defined by considering the intended use thus defining the respective port regions.

Before executing the test, the liquid transport member should be activated if necessary, as described in the above.

The test specimen is placed in a vertical position over a liquid reservoir, such as by being suspended from a holder, whereby the inlet port remains completely immersed in liquid in the reservoir The outlet port is connected such as via a flexible tubing of 6 mm outer diameter to a vacuum pump—optionally with a separator flask connected between the sample and the pump—and sealed in an air tight way as described in the above bubble point pressure method for a liquid transport member. The vacuum suction pressure differential can be monitored and adjusted.

The lowermost point of the outlet port is adjusted to be at a height $H_0$ above the liquid level in the reservoir.

The pressure differential is slowly increased to a pressure $P_0 = 0.9$ kPa $+ \rho g H_0$ with the liquid density $\rho$, and gravitational constant g (g∨9.81 m/s^2).

After reaching this pressure differential, the decrease of the weight of the liquid in the reservoir is monitored, preferably by positioning the reservoir on a scale measuring the weight of the reservoir, and connecting the scale to a computing equipment. After an initial unsteady decrease (typically taking not more than about one minute), the weight decrease in the reservoir will become constant (i.e. showing a straight line in a graphical data presentation). This constant weight decrease over time is the flow rate (in g/s) of the liquid transport member at suction of 0.9 kPa and a height $H_0$.

The corresponding flux rate of the liquid transport member at 0.9 kPa suction and a height $H_0$ is calculated from the flow rate by dividing the flow rate with the average cross section of the liquid transport member along a flow path, expressed in g/slcm$^2$.

Care should be take, that the reservoir is large enough so that the fluid level in the reservoir does not change by more than 1 mm.

In addition, the effective permeability of the liquid transport member can be calculated by dividing the flux rate by the average length along a flow path and the driving pressure difference (0.9 kPa).

Liquid Permeability Test

Generally, the test can be carried out with a suitable test fluid representing the transport fluid, such as with Jayco SynUrine as available from Jayco Pharmaceuticals Company of Camp Hill, Pa., and can be operated under controlled laboratory conditions of about 23+/−2° C. and at 50+/−10% relative humidity. However, for the present applications, and in particular when using polymeric foam materials, such as disclosed in U.S. Pat. No. 5,563,179 or U.S. Pat. No. 5.387.207, it has been found more useful to operate the test at an elevated temperature of 31° C., and by using de-ionized water as test fluid.

The present Permeability Test provides a measure for permeability for two special conditions: Either the permeability can be measured for a wide range of porous materials (such as non-wovens made of synthetic fibres, or cellulosic structures) at 100% saturation, or for materials, which reach different degrees of saturation with a proportional change in caliper without being filled with air (respectively the outside vapour phase), such as the collapsible polymeric foams, for which the permeability at varying degrees of saturation can readily be measured at various thicknesses.

In principle, this tests is based on Darcy's law, according to which the volumetric flow rate of a liquid through any porous medium is proportional to the pressure gradient, with the proportionality constant related to permeability.

$$Q/A=(k/\eta)*(\Delta P/L)$$

where:
Q=Volumetric Flow Rate [cm$^3$/s];
A=Cross Sectional Area [cm$^2$];
k=Permeability (cm$^2$) (with 1 Darcy corresponding to 9.869*10$^{-13}$ m$^2$);
$\eta$=Viscosity (Poise) [Pa*s];
$\Delta P/L$=Pressure Gradient [Pa/m];
L=caliper of sample [cm].

Hence, permeability can be calculated—for a fixed or given sample cross-sectional area and test liquid viscosity—by measurement of pressure drop and the volumetric flow rate through the sample:

$$k=(Q/A)*(L/\Delta P)*\eta$$

The test can be executed in two modifications, the first referring to the transplanar permeability (i.e. the direction of flow is essentially along the thickness dimension of the material), the second being the in-plane permeability (i.e. the direction of flow being in the x-y-direction of the material).

Figure 19:
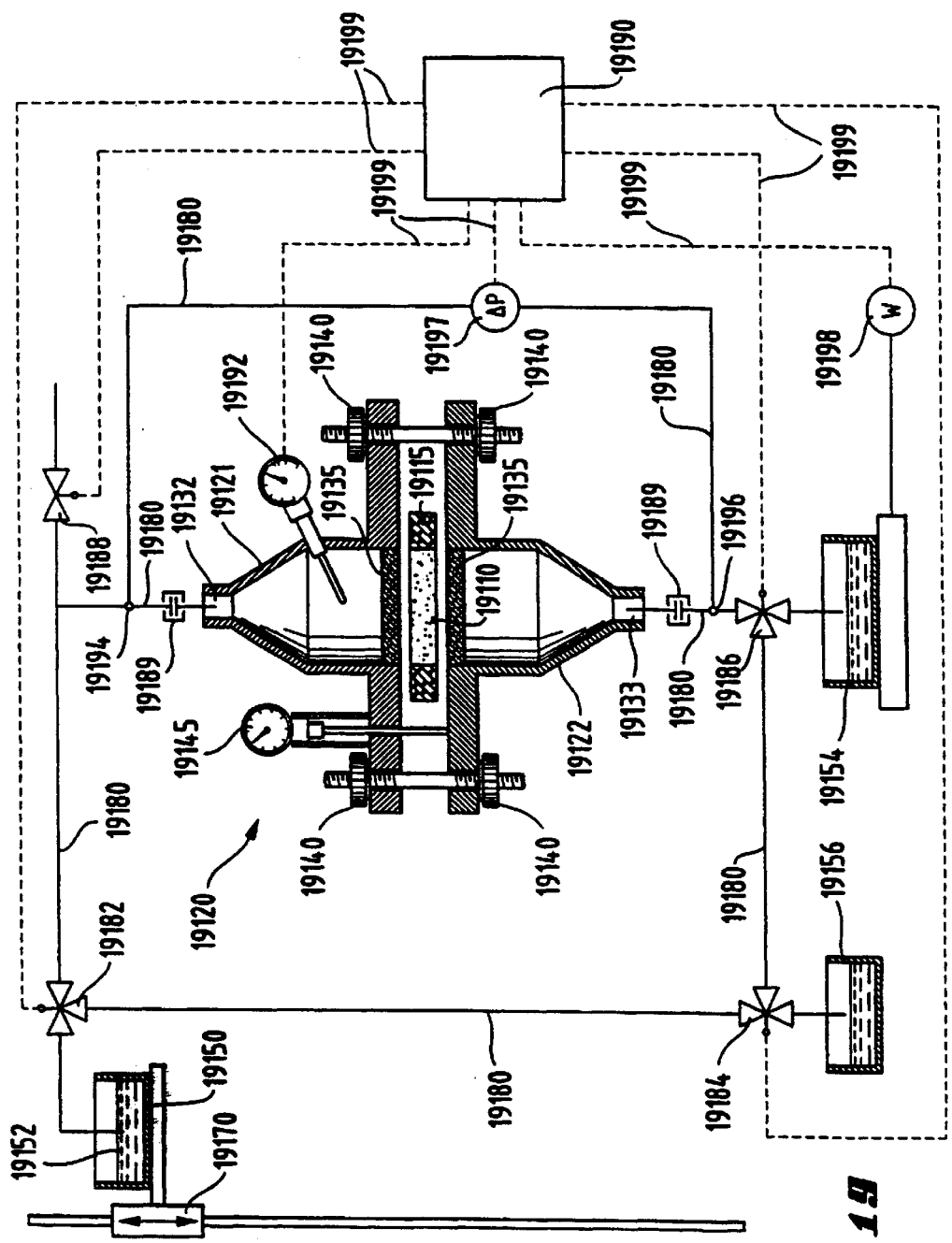
FIGS. 19 to 20A, B: Liquid permeability test.

The test set-up for the transplanar permeability test can be see in FIG. 19 which is a schematic diagram of the overall equipment and—as an insert diagram—a partly exploded cross-sectional, not to scale view of the sample cell.

The test set-up comprises a generally circular or cylindrical sample cell (19120), having an upper (19121) and lower (19122) part. The distance of these parts can be measured and hence adjusted by means of each three circumferentially arranged caliper gauges (19145) and adjustment screws (19140). Further, the equipment comprises several fluid reservoirs (19150, 19154, 19156) including a height adjustment (19170) for the inlet reservoir (19150) as well as tubings (19180), quick release fittings (19189) for connecting the sample cell with the rest of the equipment, further valves (19182, 19184, 19186, 19188). The differential pressure transducer (19197) is connected via tubing (19180) to the upper pressure detection point (19194) and to the lower pressure detection point (19196). A Computer device (19190) for control of valves is further connected via connections (19199) to differential pressure transducer (19197), temperature probe (19192), and weight scale load cell (19198).

The circular sample (19110) having a diameter of 1 in (about 2.54 cm) is placed in between two porous screens (19135) inside the sample cell (19120), which is made of two 1 in (2.54 cm) inner diameter cylindrical pieces (19121, 19122) attached via the inlet connection (19132) to the inlet reservoir (19150) and via the outlet connection (19133) to the outlet reservoir (19154) by flexible tubing (19180), such as tygon tubing. Closed cell foam gaskets (19115) provide leakage protection around the sides of the sample. The test sample (19110) is compressed to the caliper corresponding to the desired wet compression, which is set to 0.2 psi (about 1.4 kPa) unless otherwise mentioned. Liquid is allowed to flow through the sample (19110) to achieve steady state flow. Once steady state flow through the sample (19110) has been established, volumetric flow rate and pressure drop are recorded as a function of time using a load cell (19198) and the differential pressure transducer (19197). The experiment can be performed at any pressure head up to 80 cm water (about 7.8 kPa), which can be adjusted by the height adjusting device (19170). From these measurements, the flow rate at different pressures for the sample can be determined.

The equipment is commercially available as a liquid Permeameter such as supplied by Porous Materials, Inc, Ithaca, N.Y., US under the designation PMI Liquid Permeameter, such as further described in respective user manual of 2/97, and modified according to the present description. This equipment includes two Stainless Steel Frits as porous screens (19135), also specified in said brochure. The equipment consists of the sample cell (19120), inlet reservoir (19150), outlet reservoir (19154), and waste reservoir (19156) and respective filling and emptying valves and connections, an electronic scale, and a computerized monitoring and valve control unit (19190).

The gasket material (19115) is a Closed Cell Neoprene Sponge SNC-1 (Soft), such as supplied by Netherland Rubber Company, Cincinnati, Ohio, US. A set of materials with varying thickness in steps of 1/16" (about 0.159 cm) should be available to cover the range from 1/16"–1/2" (about 0.159 cm to about 1.27 cm) thickness.

Further a pressurized air supply is required, of at least 60 psi (4.1 bar), to operate the respective valves.

The test is then executed by the following steps:
1) Preparation of the Test Sample(s):

In a preparatory test, it is determined, if one or more layers of the test sample are required, wherein the test as outlined below is run at the lowest and highest pressure. The number of layers is then adjusted so as to maintain the flow rate during the test between 0.5 cm$^3$/seconds at the lowest pressure drop and 15 cm$^3$/second at the highest pressure drop. The flow rate for the sample should be less than the flow rate for the blank at the same pressure drop. If the sample flow rate exceeds that of the blank for a given pressure drop, more layers should be added to decrease the flow rate.

Sample size: Samples are cut to 1" (about 2.54 cm) diameter, by using an arch punch, such as supplied by McMaster-Carr Supply Company, Cleveland, Ohio, US. If samples have too little internal strength or integrity to maintain their structure during the required manipulation, a conventional low basis weight support means can be added, such as a PET scrim or net.

Thus, at least two samples (made of the required number of layers each, if necessary) are precut. Then, one of these is saturated in deionized water at the temperature the experiment is to be performed (70° F., (31° C.) unless otherwise noted).

The caliper of the wet sample is measured (if necessary after a stabilization time of 30 seconds) under the desired compression pressure for which the experiment will be run by using a conventional caliper gauge (such as supplied by AMES, Waltham, Mass., US) having a pressure foot diameter of 1⅛" (about 2.86 cm), exerting a pressure of 0.2 psi (about 1.4 kPa) on the sample (19110), unless otherwise desired.

An appropriate combination of gasket materials is chosen, such that the total thickness of the gasketing foam (19115) is between 150 and 200% of the thickness of the wet sample (note that a combination of varying thicknesses of gasket material may be needed to achieve the overall desired thickness). The gasket material (19115) is cut to a circular size of 3" in diameter, and a 1 inch (2.54 cm) hole is cut into the center by using the arch punch.

In case, that the sample dimensions change upon wetting, the sample should be cut such that the required diameter is taken in the wet stage. This can also be assessed in this preparatory test, with monitoring of the respective dimensions. If these change such that either a gap is formed, or the sample forms wrinkles which would prevent it from smoothly contacting the porous screens or frits, the cut diameter should be adjusted accordingly.

The test sample (19110) is placed inside the hole in the gasket foam (19115), and the composite is placed on top of the bottom half of the sample cell, ensuring that the sample is in flat, smooth contact with the screen (19135), and no gaps are formed at the sides.

The top of the test cell (19121) is laid flat on the lab bench (or another horizontal plane) and all three caliper gauges (19145) mounted thereon are zeroed.

The top of the test cell (19121) is then placed onto the bottom part (19122) such that the gasket material(19115) with the test sample (19110) lays in between the two parts. The top and bottom part are then tightened by the fixation screws (19140), such that the three caliper gauges are adjusted to the same value as measured for the wet sample under the respective pressure in the above.

2) To prepare the experiment, the program on the computerized unit (19190) is started and sample identification, respective pressure etc. are entered.

3) The test will be run on one sample (19110) for several pressure cycles, with the first pressure being the lowest pressure. The results of the individual pressure runs are put on different result files by the computerized unit (19190). Data are taken from each of these files for the calculations as described below. (A different sample should be used for any subsequent runs of the material.)

4) The inlet liquid reservoir (19150) is set to the required height and the test is started on the computerized unit (19190).

5) Then, the sample cell (19120) is positioned into the permeameter unit with Quick Disconnect fittings (19189).

6) The sample cell (19120) is filled by opening the vent valve (19188) and the bottom fill valves (19184, 19186). During this step, care must be taken to remove air bubbles from the system, which can be achieved by turning the sample cell vertically, forcing air bubbles—if present—to exit the permeameter through the drain.

Once the sample cell is filled up to the tygon tubing attached to the top of the chamber (19121), air bubbles are removed from this tubing into the waste reservoir (19156).

7) After having carefully removed air bubbles, the bottom fill valves (19184, 19186) are closed, and the top fill (19182) valve is opened, so as to fill the upper part, also carefully removing all air bubbles.

8) The fluid reservoir is filled with test fluid to the fill line (19152).

Then the flow is started through the sample by initiating the computerized unit (19190).

After the temperature in the sample chamber has reached the required value, the experiment is ready to begin.

Upon starting the experiment via the computerized unit (19190), the liquid outlet flow is automatically diverted from the waste reservoir (19156) to the outlet reservoir (19154), and pressure drop, and temperature are monitored as a function of time for several minutes.

Once the program has ended, the computerized unit provides the recorded data (in numeric and/or graphical form).

If desired, the same test sample can be used to measure the permeability at varying pressure heads, with thereby increasing the pressure from run to run.

The equipment should be cleaned every two weeks, and calibrated at least once per week, especially the frits, the load cell, the thermocouple and the pressure transducer, thereby following the instructions of the equipment supplier.

The differential pressure is recorded via the differential pressure transducer connected to the pressure probes measurement points (19194, 19196) in the top and bottom part of the sample cell. Since there may be other flow resistances within the chamber adding to the pressure that is recorded, each experiment must be corrected by a blank run. A blank run should be done at 10, 20, 30, 40, 50, 60, 70, 80 cm requested pressure, each day. The permeameter will output a Mean Test Pressure for each experiment and also an average flow rate.

For each pressure that the sample has been tested at, the flow rate is recorded as Blank Corrected Pressure by the computerized unit (19190), which is further correcting the Mean Test Pressure (Actual Pressure) at each height recorded pressure differentials to result in the Corrected Pressure. This Corrected Pressure is the DP that should be used in the permeability equation below.

Permeability can then be calculated at each requested pressure and all permeabilities should be averaged to determine the k for the material being tested.

Three measurements should be taken for each sample at each head and the results averaged and the standard deviation calculated. However, the same sample should be used, permeability measured at each head, and then a new sample should be used to do the second and third replicates.

Figure 20A:
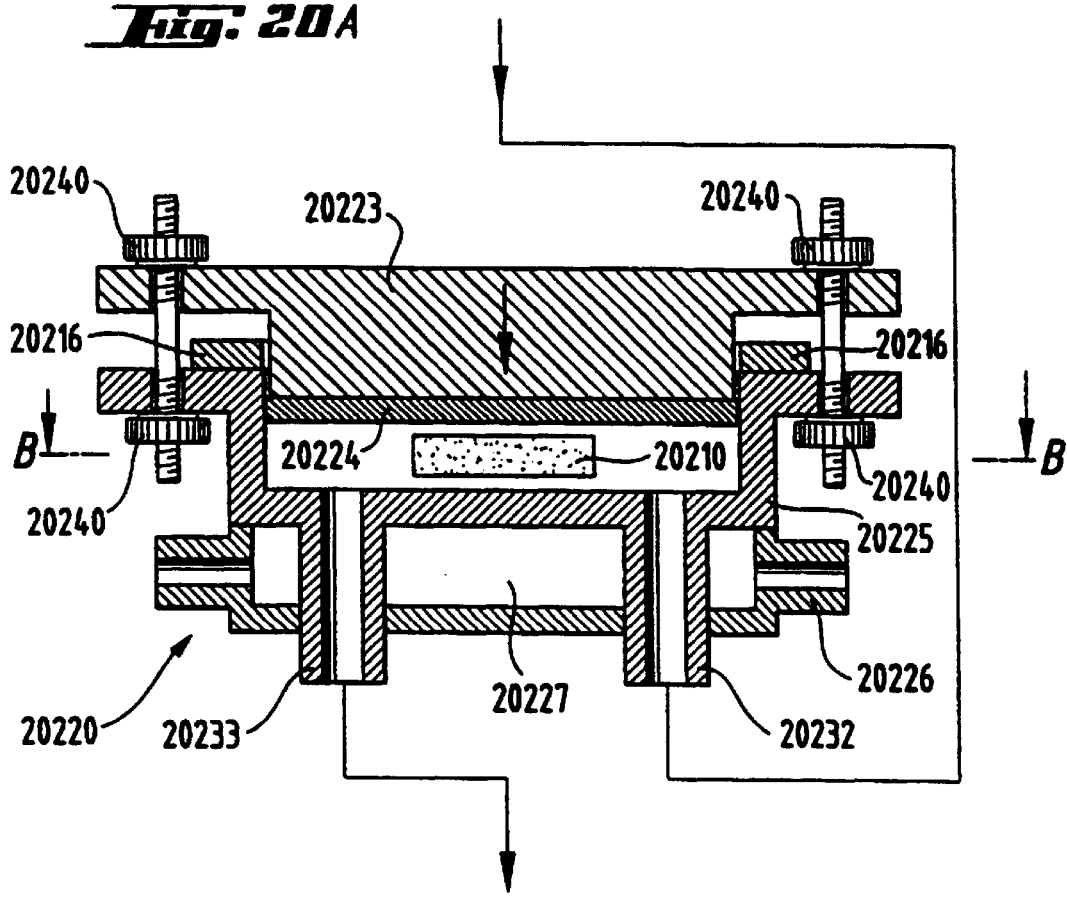
Figure 20B:
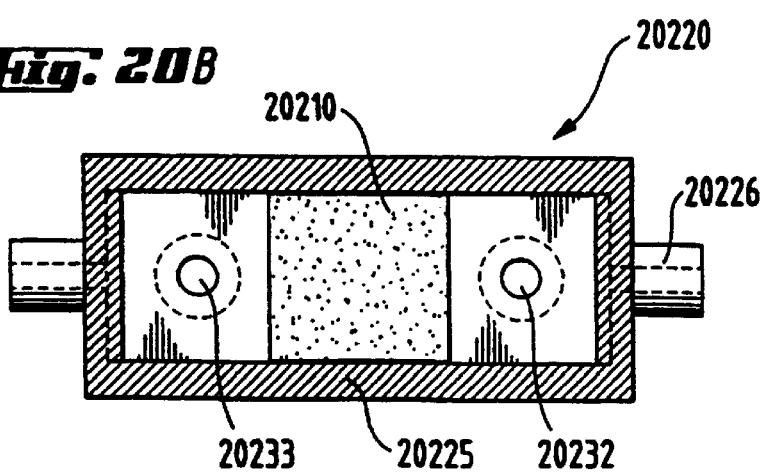

The measuring of the in-plane permeability under the same conditions as the above described transplanar permeability, can be achieved by modifying the above equipment such as schematically depicted in FIGS. 20A and 20B showing the partly exploded, not to scale view of the sample cell only. Equivalent elements are denoted equivalently, such that the sample cell of FIG. 20 is denoted (20210), correlating to the numeral (19110) of FIG. 19, and.so on. Thus, the transplanar simplified sample cell (19120) of FIG. 19 is replaced by the in-plane simplified cell (20220), which is designed so that liquid can flow only in one direction (either machine direction or cross direction depending on how the sample is placed in the cell). Care should be taken to minimize channeling of liquid along the walls (wall effects), since this can erroneously give high permeability reading. The test procedure is then executed quite analogous to the transplanar test.

The sample cell (20220) is designed to be positioned into the equipment essentially as described for the sample cell (20120) in the above transplanar test, except that the filling tube is directed to the inlet connection (20232) the bottom of the cell (20220). FIG. 20A shows a partly exploded view of the sample cell, and FIG. 20B a cross-sectional view through the sample level.

The test cell (20220) is made up of two pieces: a bottom piece (20225) which is like a rectangular box with flanges, and a top piece (20223) that fits inside the bottom piece (20225) and has flanges as well. The test sample is cut to the size of 2" in×2" in (about 5.1 cm by 5.1 cm) and is placed into the bottom piece. The top piece (20223) of the sample chamber is then placed into the bottom piece (20225) and sits on the test sample (20210). An incompressible neoprene rubber seal (20224) is attached to the upper piece (20223) to provide tight sealing. The test liquid flows from the inlet reservoir to the sample space via Tygon tubing and the inlet connection (20232) further through the outlet connection (20233) to the outlet reservoir. As in this test execution the temperature control of the fluid passing through the sample cell can be insufficient due to lower flow rates, the sample is kept at the desired test temperature by the heating device (20226), whereby thermostated water is pumped through the heating chamber (20227). The gap in the test cell is set at the caliper corresponding to the desired wet compression, normally 0.2 psi (about 1.4 kPa). Shims (20216) ranging in size from 0.1 mm to 20.0 mm are used to set the correct caliper, optionally using combinations of several shims.

At the start of the experiment, the test cell (20220) is rotated 90° (sample is vertical) and the test liquid allowed to enter slowly from the bottom. This is necessary to ensure that all the air is driven out from the sample and the inlet/outlet connections (20232/20233). Next, the test cell (20220) is rotated back to its original position so as to make the sample (20210) horizontal. The subsequent procedure is the same as that described earlier for transplanar permeability, i.e. the inlet reservoir is placed at the desired height, the flow is allowed to equilibrate, and flow rate and pressure drop are measured. Permeability is calculated using Darcy's law. This procedure is repeated for higher pressures as well.

For samples that have very low permeability, it may be necessary to increase the driving pressure, such as by extending the height or by applying additional air pressure on the reservoir in order to get a measurable flow rate. In plane permeability can be measured independently in the machine and cross directions, depending on how the sample is placed in the test cell.

Determination of Pore Size

Optical determination of pore size is especially used for thin layers of porous system by using standard image analysis procedures know to the skilled artisan.

The principle of the method consists of the following steps: 1) A thin layer of the sample material is prepared by either slicing a thick sample into thinner sheets or if the sample itself is thin by using it directly. The term "thin" refers to achieving a sample caliper low enough to allow a clear cross-section image under the microscope. Typical sample calipers are below 200 $\mu$m. 2) A microscopic image is obtained via a video microscope using the appropriate magnification. Best results are obtained if about 10 to 100 pores are visible on said image. The image is then digitized by a standard image analysis package such as OPTIMAS by BioScan Corp. which runs under Windows 95 on a typical IBM compatible PC. Frame grabber of sufficient pixel resolution (preferred at least 1024×1024 pixels) should be used to obtain good results. 3) The image is converted to a binary image using an appropriate threshold level such that the pores visable on the image are marked as object areas in white and the rest remains black. Automatic threshold setting procedures such as available under OPTIMAS can be used. 4) The areas of the individual pores (objects) are determined. OPTIMAS offers fully automatic determination of the areas. 5) The equivalent radius for each pore is determined by a circle that would have the same area as the pore. If A is the area of the pore, then the equivalent radius is given by $r=(A/\pi)^{1/2}$. The average pore size can then be determined from the pore size distribution using standard statistical rules. For materials that have a not very uniform pore size it is recommended to use at least 3 samples for the determination.

Alternative equipments useful for determining pores sizes are commercially available Porosimeter or Permeater Tester, such as a Permeameter supplied by Porous Materials, Inc, Ithaca, N.Y., US under the designation PMI Liquid Permeameter model no. CFP-1200AEXI, such as further described in respective user manual of 2/97.

Demand Absorbency Test

The demand absorbency test is intended to measure the liquid capacity of liquid handling member and to measure the absorption speed of liquid handling member against zero hydrostatic pressure. The test may also be carried out for devices for managing body liquids containing a liquid handling member.

The apparatus used to conduct this test consists of a square basket of a sufficient size to hold the liquid handling member suspended on a frame. At least the lower plane of the square basket consists of an open mesh that allows liquid penetration into the basket without substantial flow resistance for the liquid uptake. For example, an open wire mesh made of stainless steel having an open area of at least 70 percent and having a wire diameter of 1 mm, and an open mesh size of at about 6 mm is suitable for the setup of the present test. In addition, the open mesh should exhibit sufficient stability such that it substantially does not deform under load of the test specimen when the test specimen is filled up to its full capacity.

Below the basket, a liquid reservoir is provided. The height of the basket can be adjusted so that a test specimen which is placed inside the basket may be brought into contact with the surface of the liquid in the liquid reservoir. The liquid reservoir is placed on the electronic balance connected to a computer to read out the weight of the liquid about every 0.01 sec during the measurement. The dimensions of the apparatus are chosen such that the liquid handling member to be tested fits into the basket and such that the intended liquid acquisition zone of the liquid handling member is in contact with the lower plane of the basket. The dimensions of the liquid reservoir are chosen such that the level of the liquid surface in the reservoir does not substantially change during the measurement. A typical reservoir useful for testing liquid handling members has a size of at least 320 mm×370 mm and can hold at least about 4500 g of liquid.

Before the test, the liquid reservoir is filled with synthetic urine. The amount of synthetic urine and the size of the liquid reservoir should be sufficient such that the liquid level in the reservoir does not change when the liquid capacity of the liquid handing member to be tested is removed from the reservoir.

The temperature of the liquid and the environment for the test should reflect in-use conditions of the member. Typical temperature for use in baby diapers are 32 degrees Celsius for the environment and 37 degrees Celsius for the synthetic urine. The test may be done at room temperature if the member tested has no significant dependence of its absorbent properties on temperature.

The test is setup by lowering the empty basket until the mesh is just completely immersed in the synthetic urine in the reservoir. The basket is then raised again by about 0.5 to 1 mm in order to establish an almost zero hydrostatic suction, care should be taken that the liquid stays in contact with the mesh. If necessary, the mesh needs to be brought back into contact with the liquid and zero level be readjusted.

The test is started by:
1. starting the measurement of the electronic balance;
2. placing the liquid handling member on the mesh such that the acquisition zone of the member is in contact with the liquid;

3. immediately adding a low weigh on top of the member in order to provide a pressure of 165 Pa for better contact of the member to the mesh.

During the test, the liquid uptake by the liquid handing member is recorded by measuring the weight decrease of the liquid in the liquid reservoir. The test is stopped after 30 minutes.

At the end of the test, the total liquid uptake of the liquid handing member is recorded. In addition, the time after which the liquid handling member had absorbed 80 percent of its total liquid uptake is recorded. The zero time is defined as the time where the absorption of the member starts. The initial absorption speed of the liquid handling member is—from the initial linear slope of the weight vs. time measurement curve.

Capillary Sorption

Purpose

The purpose of this test is to measure the capillary sorption absorbent capacity, as a function of height, of storage absorbent members of the present invention. This test may also be used to measure the capillary sorption absorbent capacity of devices for handling body liquids according to the present invention. Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B.V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

Principle

A porous glass frit is connected via an uninterrupted column of fluid to a fluid reservoir on a balance. The sample is maintained under a constant confining weight during the experiment. As the porous structure absorbs fluid upon demand, the weight loss in the balance fluid reservoir is recorded as fluid uptake, adjusted for uptake of the glass frit as a function of height and evaporation. The uptake or capacity at various capillary suctions (hydrostatic tensions or heights) is measured. Incremental absorption occurs due to the incremental lowering of the frit (i.e., decreasing capillary suction).

Time is also monitored during the experiment to enable calculation of initial effective uptake rate (g/g/h) at a 200 cm height.

Reagents

Test Liquid: Synthetic Urine is Prepared by Completely Dissolving the Following Materials in Distilled Water.

| Compound | weight | Concentration (g/l) |
|---|---|---|
| KCl | 74.6 | 2.0 |
| $Na_2SO_4$ | 142 | 2.0 |
| $(NH_4)H_2PO_4$ | 115 | 0.85 |
| $(NH_4)_2HPO_4$ | 132 | 0.15 |
| $CaCl_2.2H_2O$ | 147 | 0.25 |
| $MgCl_2.6H_2O$ | 203 | 0.5 |

General Description of Apparatus Set Up

Figure 21A:
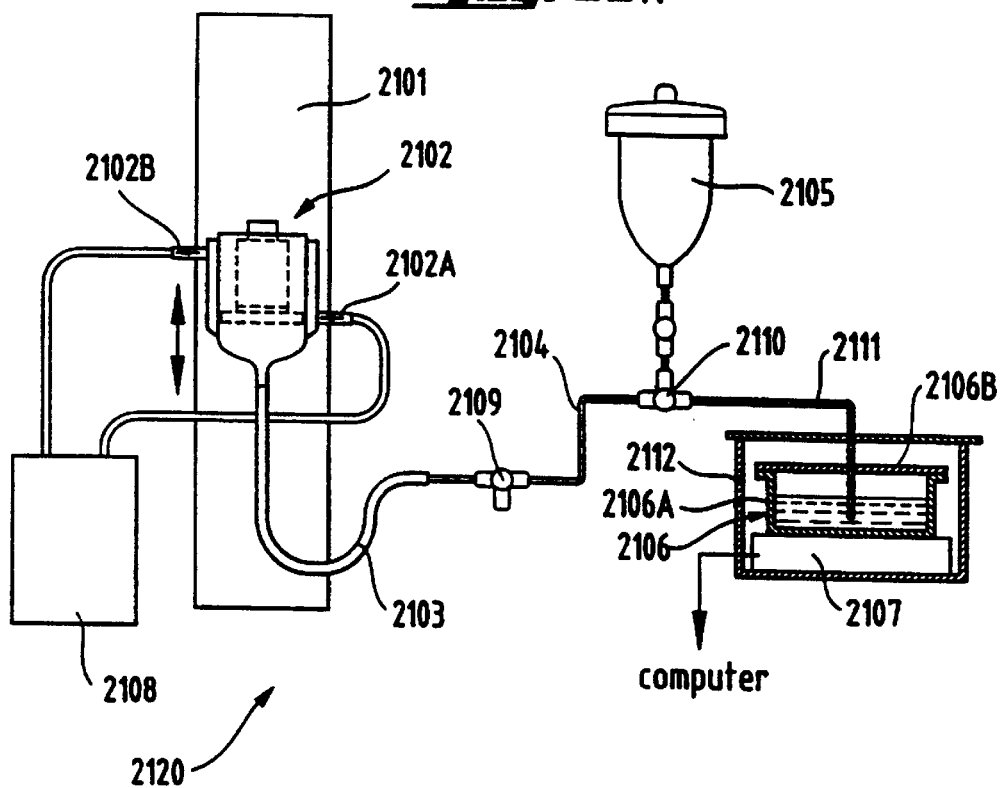
FIGS. 21A, B, C, D: Capillary absorption test.

The Capillary Sorption equipment, depicted generally as 2120 in FIG. 21A, used for this test is operated under TAPPI conditions (50% RH, 25° C.). A test sample is placed on a glass frit shown in FIG. 21A as 2102 that is connected via a continuous column of test liquid (synthetic urine) to a balance liquid reservoir, shown as 2106, containing test liquid. This reservoir 2106 is placed on a balance 2107 that is interfaced with a computer (not shown). The balance should be capable of reading to 0.001 g; such a balance is available from Meftler Toledo as PR1203 (Hightstown, N.J.). The glass frit 2102 is placed on a vertical slide, shown generally in FIG. 21A as 2101, to allow vertical movement of the test sample to expose the test sample to varying suction heights. The vertical slide may be a rodless actuator which is attached to a computer to record suction heights and corresponding times for measuring liquid uptake by the test sample. A preferred rodless actuator is available from Industrial Devices (Novato, Calif.) as item 202X4X34N-1D4B-84-P-C-S-E, which may be powered by motor drive ZETA 6104-83-135, available from CompuMotor (Rohnert, Calif.). Where data is measured and sent from actuator 2101 and balance 2107, capillary sorption absorbent capacity data may be readily generated for each test sample. Also, computer interface to actuator 2101 may allow for controlled vertical movement of the glass frit 2102. For example, the actuator may be directed to move the glass frit 2102 vertically only after "equilibrium" (as defined below) is reached at each suction height.

The bottom of glass frit 2102 is connected to Tygon® tubing 2103 that connects the frit 2105 to three-way drain stopcock 2109. Drain stopcock 2109 is connected to liquid reservoir 2105 via glass tubing 2104 and stopcock 2110. (The stopcock 2109 is open to the drain only during cleaning of the apparatus or air bubble removal.) Glass tubing 2111 connects fluid reservoir 2105 with balance fluid reservoir 2106, via stopcock 2110. Balance liquid reservoir 2106 consists of a lightweight 12 cm diameter glass dish 2106A and cover 2106B. The cover 2106B has a hole through which glass tubing 2111 contacts the liquid in the reservoir 2106. The glass tubing 2111 must not contact the cover 2106B or an unstable balance reading will result and the test sample measurement cannot be used. In this context, it is to be understood that the volume of the liquid reservoir needs to be compatible with the absorbent capacity of the liquid handing member or the device to be tested. Hence, it may be necessary to choose a different liquid reservoir.

The glass frit diameter must be sufficient to accommodate the piston/cylinder apparatus, discussed below, for holding the test sample. The glass frit 2102 is jacketed to allow for a constant temperature control from a heating bath. The frit is a 350 ml fritted disc funnel specified as having 4 to 5.5 $\mu$m pores, available from Corning Glass Co. (Corning, N.Y.) as #36060-350F. The pores are fine enough to keep the frit surface wetted at capillary suction heights specified (the glass frit does not allow air to enter the continuous column of test liquid below the glass frit).

As indicated, the frit 2102 is connected via tubing to fluid reservoir 2105 or balance liquid reservoir 2106, depending on the position of three-way stopcock 2110.

Glass frit 2102 is jacketed to accept water from a constant temperature bath. This will ensure that the temperature of the glass frit is kept at a constant temperature of 88° F. (31°

C.) during the testing procedure. As is depicted in FIG. 21A, the glass frit 2102 is equipped with an inlet port 2102A and outlet port 2102B, which make a closed loop with a circulating heat bath shown generally as 2108. (The glass jacketing is not depicted in FIG. 21A. However, the water introduced to the jacketed glass frit 2102 from bath 2108 does not contact the test liquid and the test liquid is not circulated through the constant temperature bath. The water in the constant temperature bath circulates through the jacketed walls of the glass frit 2102.)

Reservoir 2106 and balance 2107 are enclosed in a box to minimize evaporation of test liquid from the balance reservoir and to enhance balance stability during performance of the experiment. This box, shown generally as 2112, has a top and walls, where the top has a hole through which tubing 2111 is inserted.

Figure 21D:
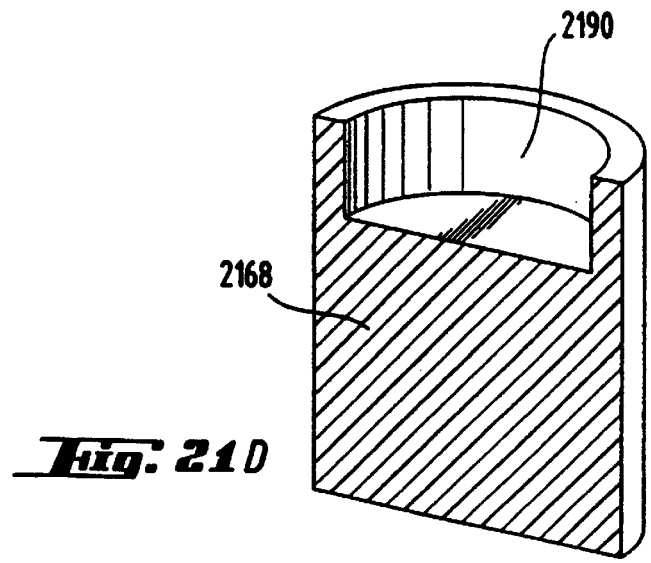
Figure 21B:
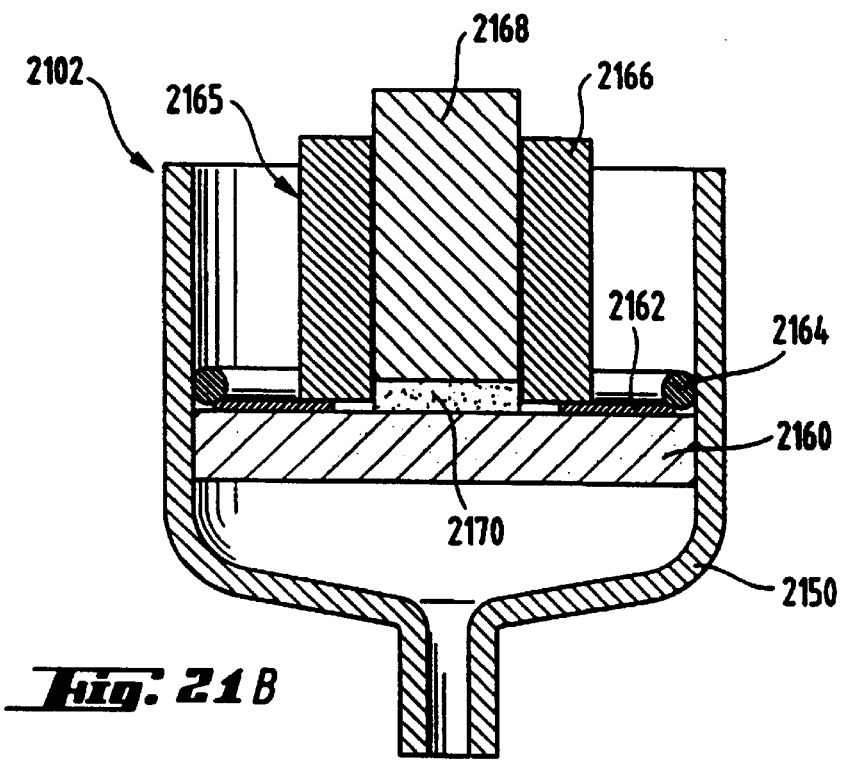

The glass frit 2102 is shown in more detail in FIG. 21B. FIG. 21B is a cross-sectional view of the glass frit, shown without inlet port 2102A and outlet port 2102B. As indicated, the glass frit is a 350 ml fritted disc funnel having specified 4 to 5.5 $\mu$m pores. Referring to FIG. 21B, the glass frit 2102 comprises a cylindrical jacketed funnel designated as 2150 and a glass frit disc shown as 2160. The glass frit 2102 further comprises a cylinder/piston assembly shown generally as 2165 (which comprises cylinder 2166 and piston 2168), which confines the test sample, shown as 2170, and provides a small confining pressure to the test sample. To prevent excessive evaporation of test liquid from the glass frit disc 2160, a Teflon ring shown as 2162 is placed on top of the glass frit disc 2160. The Teflon® ring 2162 is 0.0127 cm thick (available as sheet stock from McMaster-Carr as # 8569K16 and is cut to size) and is used to cover the frit disc surface outside of the cylinder 2166, and thus minimizes evaporation from the glass frit. The ring outer diameter and inner diameter is 7.6 and 6.3 cm, respectively. The inner diameter of the Teflon® ring 2162 is about 2 mm less than the outer diameter of cylinder 2166. A Viton® O-ring (available from McMasterCarr as # AS568A-150 and AS568A-151) 2164 is placed on top of Teflon® ring 2162 to seal the space between the inner wall of cylindrical jacketed funnel 2150 and Teflon® ring 2162, to further assist in prevention of evaporation. If the O-ring outer diameter exceeds the inner diameter of cylindrical jacketed funnel 2150, the O-ring diameter is reduced to fit the funnel as follows: the O-ring is cut open, the necessary amount of O-ring material is cut off, and the O-ring is glued back together such that the O-ring contacts the inner wall of the cylindrical jacketed funnel 2150 all around its periphery. While the above described frit represents one suitable example of frit, it may be necessary to use of frit having dimensions different from the above dimensions in order to better fit the dimensions of the liquid handling member or the device to be tested. The surface area of the frit should resemble as closely as possible the surface area of the acquisition zone of the liquid handling member or the device in order to fully use the acquisition zone and in order to minimize the evaporation from the frit.

Figure 21C:
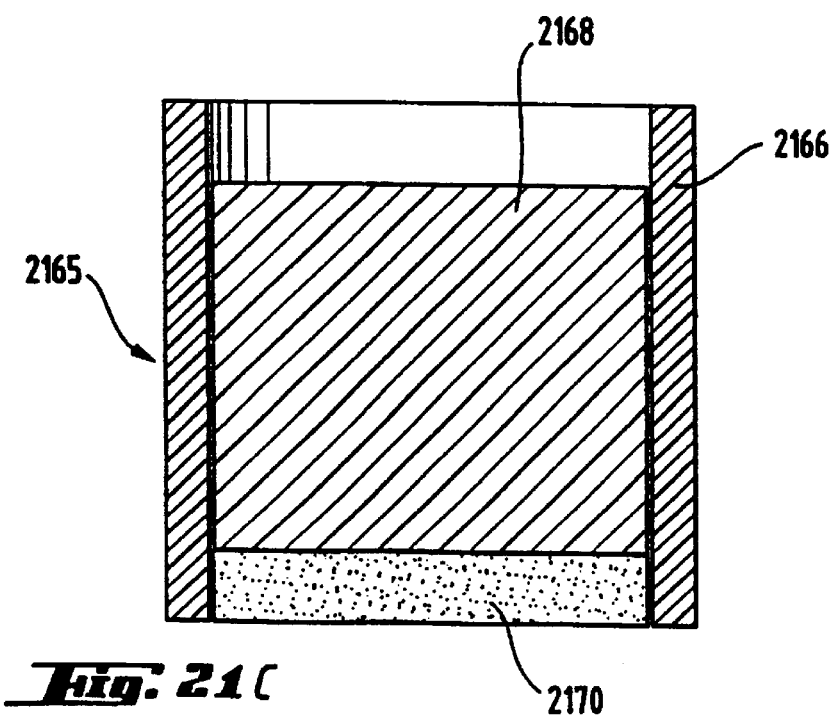

As indicated, a cylinder/piston assembly shown generally in FIG. 21B as 2165 confines the test sample and provides a small confining pressure to the test sample 2170. Referring to FIG. 21C, assembly 2165 consists of a cylinder 2166, a cup-like Teflon® piston indicated by 2168 and, when necessary, a weight or weights (not shown) that fits inside piston 2168. (Optional weight will be used when necessary to adjust the combined weight of the piston and the optional weight so a confining pressure of 0.2 psi is attained depending on the test sample's dry diameter. This is discussed below.) The cylinder 2166 is Lexan® bar stock and has the following dimensions: an outer diameter of 7.0 cm, an inner diameter of 6.0 cm and a height of 6.0 cm. The Teflon® piston 2168 has the following dimensions: an outer diameter that is 0.02 cm less than the inner diameter of cylinder 2166. As shown in FIG. 21D, the end of the piston 2168 that does not contact the test sample is bored to provide a 5.0 cm diameter by about 1.8 cm deep chamber 2190 to receive optional weights (dictated by the test sample's actual dry diameter) required to attain a test sample confining pressure of 0.2 psi (1.4 kPa). In other words, the total weight of is the piston 2168 and any optional weights (not shown in figures) divided by the test sample's actual diameter (when dry) should be such that a confining pressure of 0.2 psi is attained. Cylinder 2166 and piston 2168 (and optional weights) are equilibrated at 31° C. for at least 30 minutes prior to conducting the capillary sorption absorbent capacity measurement. Again, the above described dimensions are chosen to fit the above described exemplary frit. When a different frit is chosen the dimensions of the cylinder/piston assembly need to be adjusted accordingly.

A non-surfactant treated or incorporated apertured film (14 cm×14 cm) (not shown) is used to cover the glass frit 2102 during Capillary Sorption experiments to minimize air destablization around the sample. Apertures are large enough to prevent condensation from forming on the underside of the film during the experiment.

Test Sample Preparation

For the present procedure, it is important, that the simensions of the sample and of the frit should not be too different. To achieve this, two approaches can be taken:

a) For test samples, which can be readiliy adjusted to a suitable size, such as by cutting these, both the size of this cutting as well as of the frit are choosen to be a circualr shaped structure of 5.4 cm diameter, such as can be done by using a conventional arc puch.

b) When the test sample cannot readily be cut to this dimension, the size and preferably also the shape of the frit has to be adjusted to the size and shape of the test sample.

In both cases, the test sample can be a readily separatable element of a member or a device, it can be a particular component of any of these, or can be a combination of componets thereof. It might also be necesseray to adjust the sze of the liquid reservoir to macth the varying requirements.

The dry weight of the test sample (used below to calculate capillary sorption absorbent capacity) is the weight of the test sample prepared as above under ambient conditions.

Experimental Set Up

1. Place a clean, dry glass frit 2102 in a funnel holder attached to the vertical slide 2101. Move the funnel holder of the vertical slide such that the glass frit is at the 0 cm height.

2. Set up the apparatus components as shown in FIG. 21A, as discussed above.

3. Place 12 cm diameter balance liquid reservoir 2106 on the balance 2107. Place plastic lid 2106B over this balance liquid reservoir 2106 and a plastic lid over the balance box 2112 each with small holes to allow the glass tubing 2111 to fit through. Do not allow the glass tubing to touch the lid 2106B of the balance liquid reservoir or an unstable balance reading will result and the measurement cannot be used.

4. Stopcock 2110 is closed to tubing 2104 and opened to glass tubing 2111. Fluid reservoir 2105, previously filled with test fluid, is opened to allow test fluid to enter tubing 2111, to fill balance fluid reservoir 2106.

5. The glass frit 2102 is leveled and secured in place. Also, ensure that the glass frit is dry.

6. Attach the Tygon® tubing 2103 to stopcock 2109. (The tubing should be long enough to reach the glass frit 2102 at its highest point of 200 cm with no kinks.) Fill this Tygon® tubing with test liquid from liquid reservoir 2105.

7. Attach the Tygon® tubing 2103 to the level glass frit 2102 and then open stopcock 2109 and stopcock 2110 leading from fluid reservoir 2105 to the glass frit 2102. (Stopcock 2110 should be closed to glass tubing 2111.) The test liquid fills the glass frit 2102 and removes all trapped air during filling of the level glass frit. Continue to fill until the fluid level exceeds the top of the glass frit disc 2160. Empty the funnel and remove all air bubbles in the tubing and inside the funnel. Air bubbles may be removed by inverting glass frit 2102 and allowing air bubbles to rise and escape through the drain of stopcock 2109. (Air bubbles typically collect on the bottom of the glass frit disc 2160.) Relevel the frit using a small enough level that it will fit inside the jacketed funnel 2150 and onto the surface of glass frit disc 2160.

8. Zero the glass frit with the balance liquid reservoir 2106. To do this, take a piece of Tygon® tubing of sufficient length and fill it with the test liquid. Place one end in the balance liquid reservoir 2106 and use the other end to position the glass frit 2102. The test liquid level indicated by the tubing (which is equivalent to the balance liquid reservoir level) is 10 mm below the top of the glass frit disc 2160. If this is not the case, either adjust the amount of liquid in the reservoir or reset the zero position on the vertical slide 2101.

9. Attach the outlet and inlet ports from the temperature bath 2108 via tubing to the inlet and outlet ports 2102A and 2102B, respectively, of the glass frit. Allow the temperature of the glass frit disc 2160 to come to 31° C. This can be measured by partially filling the glass frit with test liquid and measuring its temperature after it has reached equilibrium temperature. The bath will need to be set a bit higher than 31° C. to allow for the dissipation of heat during the travel of water from the bath to the glass frit.

10. The glass frit is equilibrated for 30 minutes.

Capillary Sorption Parameters

The following describes a computer program that will determine how long the glass frit remains at each height.

In the capillary sorption software program; a test sample is at some specified height from the reservoir of fluid. As indicated above, the fluid reservoir is on a balance, such that a computer can read the balance at the end of a known time interval and calculate the flow rate (Delta reading/time interval) between the test sample and reservoir. For purposes of this method, the test sample is considered to be at equilibrium when the flow rate is less than a specified flow rate for a specified number of consecutive time intervals. It is recognized, that for certain material, actual equilibrium may not be reached when the specified "EQUILIBRIUM CONSTANT" is reached. The time interval between readings is 5 seconds.

The number of readings in the delta table is specified in the capillary sorption menu as "EQUILIBRIUM SAMPLES". The maximum number of deltas is 500. The flow rate constant is specified in the capillary sorption menu as "EQUILIBRIUM CONSTANT".

The Equilibrium Constant is entered in units of grams/sec, ranging from 0.0001 to 100.000.

The following is a simplified example of the logic. The table shows the balance reading and Delta Flow calculated for each Time Interval.

Equilibrium Sample=3
Equilibrium Constant=0.0015

| Time Interval | Balance Value (g) | Delta Flow (g/sec) |
|---|---|---|
| 0 | 0 | |
| 1 | 0.090 | 0.0180 |
| 2 | 0.165 | 0.0150 |
| 3 | 0.225 | 0.0120 |
| 4 | 0.270 | 0.0090 |
| 5 | 0.295 | 0.0050 |
| 6 | 0.305 | 0.0020 |
| 7 | 0.312 | 0.0014 |
| 8 | 0.316 | 0.0008 |
| 9 | 0.318 | 0.0004 |

Delta Table:

| Time | 0 | 1 | 2 | 3 | 4 | 5 | 6 | 7 | 8 | 9 |
|---|---|---|---|---|---|---|---|---|---|---|
| Delta 1 | 9999 | 0.0180 | 0.0180 | 0.0180 | 0.0090 | 0.0090 | 0.0090 | 0.0014 | 0.0014 | 0.0014 |
| Delta 2 | 9999 | 9999 | 0.0150 | 0.0150 | 0.0150 | 0.0050 | 0.0050 | 0.0050 | 0.0008 | 0.0008 |
| Delta 3 | 9999 | 9999 | 9999 | 0.0120 | 0.0120 | 0.0120 | 0.0020 | 0.0020 | 0.0020 | 0.0004 |

The equilibrium uptake for the above simplified example is 0.318 gram.

The following is the code in C language used to determine equilibrium uptake:

```
/*                    takedata.c                    */
int take_data(int equil_samples.double equilibrium_constant)
{
double    delta:
static    double deltas[500]; /* table to store up to 500 deltas */
double    value;
double    prev_value;
clock_t   next_time;
int       i;
for (i=0; i<equil_samples; i++)
     deltas[i] = 9999.;                  /* initialize all values in the delta
table to 9999. gms/sec */
delta_table_index = 0;                   /* initialize where in the table to store
the next delta */
equilibrium_reached = 0;                 /* initialize flag to indicate equilibrium
has not been reached */
next_time = clock( );                    /* initialize when to take the next
reading */
prev_reading = 0.;                       /* initialize the value of the previous
reading from the balance */
while (!equilibrium_reached) {           /* start of loop for checking for
equilibrium */
    next_time += 5000L;                  /* calculate when to take next reading
*/
    while   (clock( ) < next_time};      /* wait until 5 seconds has elasped
from prev reading =/
    value = get_balance_reading( ) ;     /* read the balance in grams */
    delta = fabs(prev_value - value) / 5.0;  /* calculate absolute value of flow in
last 5 seconds */
    prev_value = value;                  /* store current value for next loop
*/
    deltas(delta_table_index) = delta;   /* store current delta value in the
table of deltas */
    delta_table_index++;                 /* increment pointer to next position
in table */
    if (delta_table_index == equil_samples)  /* when the number of deltas = the
number of */
        delta_table_index = 0;           /* equilibrium samples specified. /*
                                         /* reset the pointer to the start of
the table. This way */
                                         /* the table always contains the last
xx current samples. */
    equilibrium_reached = 1;             /* set the flag to indicate
equilibrium is reached */
    for (i=0; i < equil_samples; i++)    /* check all the values in the delta
table */
        if (deltas[i] >= equilibrium_constant)  /* if any value is > or = to the
equilibrium constant */
            equilibrium reached = 0;     /* set the equlibrium flag to 0 (not
at equilibrium) */
    }                                    /* go back to the start of the loop */
}
```

Capillary Sorption Parameters

Load Description (Confining Pressure): 0.2 psi load

Equilibrium Samples (n): 50

Equilibrium Constant: 0.0005 g/sec

Setup Height Value: 100 cm

Finish Height Value: 0 cm

Hydrostatic Head Parameters: 200, 180, 160, 140, 120, 100, 90, 80, 70, 60, 50, 45, 40, 35, 30, 25, 20, 15, 10, 5 and 0 cm.

The capillary sorption procedure is conducted using all the heights specified above, in the order stated, for the measurement of capillary sorption absorbent capacity. Even if it is desired to determine capillary sorption absorbent capacity at a particular height (e.g., 35 cm), the entire series of hydrostatic head parameters must be completed in the order specified. Although all these heights are used in performance of the capillary sorption test to generate capillary sorption isotherms for a test sample, the present disclosure describes the storage absorbent members in terms of their absorbent properties at specified heights of 200, 140, 100, 50, 35 and 0 cm.

Capillary Sorption Procedure

1) Follow the experimental setup procedure.

2) Make sure the temperature bath 2108 is on and water is circulating through the glass frit 2102 and that the glass frit disc 2160 temperature is 31° C.

3) Position glass frit 2102 at 200 cm suction height. Open stopcocks 2109 and 2110 to connect glass frit 2102 with the balance liquid reservoir 2106. (Stopcock 2110 is closed to liquid reservoir 2105.) Glass frit 2102 is equilibrated for 30 minutes.

4) Input the above capillary sorption parameters into the computer.

5) Close stopcocks 2109 and 2110.

6) Move glass frit 2102 to the set up height, 100 cm.
7) Place Teflon® ring 2162 on surface of glass frit disc 2160. Put O-ring 2164 on Teflon® ring. Place preheated cylinder 2166 concentrically on the Teflon® ring. Place test sample 2170 concentrically in cylinder 2166 on glass frit disc 2160. Place piston 2168 into cylinder 2166. Additional confining weights are placed into piston chamber 2190, if required.
8) Cover the glass frit 2102 with apertured film.
9) The balance reading at this point establishes the zero or tare reading.
10) Move the glass frit 2102 to 200 cm.
11) Open stopcocks 2109 and 2110 (stopcock 2110 is closed to fluid reservoir 2105) and begin balance and time readings.

Glass Frit Correction (Blank Correct Uptake)

Since the glass frit disc 2160 is a porous structure, the glass frit 2102 capillary sorption absorption uptake (blank correct uptake) must be determined and subtracted to get the true test sample capillary sorption absorption uptake. The glass frit correction is performed for each new glass frit used. Run the capillary sorption procedure as described above, except without test sample, to obtain the Blank Uptake (g). The elapsed time at each specified height equals the Blank Time (s).

Evaporation Loss Correction

1) Move the glass frit 2102 to 2 cm above zero and let it equilibrate at this height for 30 minutes with open stopcocks 2109 and 2110 (closed to reservoir 2105).
2) Close stopcocks 2109 and 2110.
3) Place Teflon® ring 2162 on surface of glass frit disc 2160. Put O-ring 2164 on Teflon® ring. Place preheated cylinder 2166 concentrically on the Teflon® ring. Place piston 2168 into cylinder 2166. Place apertured film on glass frit 2102.
4) Open stopcocks 2109 and 2110 (closed to reservoir 2105) and record balance reading and time for 3.5 hours. Calculate Sample Evaporation (g/hr) as follows: [balance reading at 1 hr—balance reading at 3.5 hr]/2.5 hr Even after taking all the above precautions, some evaporative loss will occur, typically around 0.10 gm/hr for both the test sample and the frit correction. Ideally, the sample evaporation is measured for each newly installed glass frit 2102.

Cleaning the Equipment

New Tygon® tubing 2103 is used when a glass frit 2102 is newly installed. Glass tubing 2104 and 2111, fluid reservoir 2105, and balance liquid reservoir 2106 are cleaned with 50% Clorox Bleach® in distilled water, followed by distilled water rinse, if microbial contamination is visible.

a. Cleaning After Each Experiment

At the end of each experiment (after the test sample has been removed), the glass frit is forward flushed (i.e., test liquid is introduced into the bottom of the glass frit) with 250 ml test liquid from liquid reservoir 2105 to remove residual test sample from the glass frit disc pores. With stopcocks 2109 and 2110 open to liquid reservoir 2105 and closed to balance liquid reservoir 2106, the glass frit is removed from its holder, turned upside down and is rinsed out first with test liquid, followed by rinses with acetone and test liquid (synthetic urine). During rinsing, the glass frit must be tilted upside down and rinse fluid is squirted onto the test sample contacting surface of the glass frit disc. After rinsing, the glass frit is forward flushed a second time with 250 ml test liquid (synthetic urine). Finally, the glass frit is reinstalled in its holder and the frit surface is leveled.

b. Monitoring Glass Frit Performance

Glass frit performance must be monitored after each cleaning procedure and for each newly installed glass frit, with the glass frit set up at 0 cm position. 50 ml of test liquid are poured onto the leveled glass frit disc surface (without Teflon® ring, O-ring and the cylinder/piston components). The time it takes for the test fluid level to drop to 5 mm above the glass frit disc surface is recorded. A periodic cleaning must be performed if this time exceeds 4.5 minutes.

c. Periodic Cleaning

Periodically, (see monitoring frit performance, above) the glass frits are cleaned thoroughly to prevent clogging. Rinsing fluids are distilled water, acetone, 50% Clorox Bleach® in distilled water (to remove bacterial growth) and test liquid. Cleaning involves removing the glass frit from the holder and disconnecting all tubing. The glass frit is forward flushed (i.e., rinse liquid is introduced into the bottom of the glass frit) with the frit upside down with the appropriate fluids and amounts in the following order:

1. 250 ml distilled water.
2. 100 ml acetone.
3. 250 ml distilled water.
4. 100 ml 50:50 Clorox®/distilled water solution.
5. 250 ml distilled water.
6. 250 ml test fluid.

The cleaning procedure is satisfactory when glass frit performance is within the set criteria of fluid flow (see above) and when no residue is observable on the glass frit disc surface. If cleaning can not be performed successfully, the frit must be replaced.

Calculations

The computer is set up to provide a report consisting of the capillary suction height in cm, time, and the uptake in grams at each specified height. From this data, the capillary suction absorbent capacity, which is corrected for both the frit uptake and the evaporation loss, can be calculated. Also, based on the capillary suction absorbent capacity at 0 cm, the capillary absorption efficiency can be calculated at the specified heights. In addition, the initial effective uptake rate at 200 cm is calculated.

Blank Correct Uptake $$\text{Blank Correct Uptake(g)} = \text{Blank Uptake(g)} - \frac{\text{Blank Time(s)} * \text{Sample Evap. (g/hr)}}{3600 \ (\text{s/hr})}$$

Capillary Suction Absorbent Capacity ("CSAC")

$$CSAC \ (g/g) = \frac{\text{Sample Uptake(g)} - \frac{\text{Sample Time (s)} * \text{Sample Evap. (g/hr)}}{36000 \ \text{s/hr}} - \text{Blank Correct Uptake(g)}}{\text{Dry Weight of Sample(g)}}$$

Initial Effective Uptake Rate at 200 cm ("IEUR")

$$IEUR \ (g/g/hr) = \frac{CSAC \ \text{at 200 cm (g/g)}}{\text{Sample Time at 200 cm (s)}}$$

Reporting

A minimum of two measurements should be taken for each sample and the uptake averaged at each height to calculate Capillary Sorption Absorbent Capacity (CSAC) for a given absorbent member or a given high surface area material.

With these data, the respective values can be calculated:

The Capillary Sorption Desorption Height at which the material has released x% of its capacity at 0 cm (i.e. of CSAC 0), (CSDH x) expressed in cm;

The Capillary Sorption Absorption Height at which the material has absorbed y% of its capacity at 0 cm (i.e. of CSAC 0), (CSAH y) expressed in cm;

The Capillary Sorption Absorbent Capacity at a certain height z (CSAC z) expressed in units of g {of fluid}/g {of material}; especially at the height zero (CSAC 0), and at heights of 35 cm, 40 cm, etc;

The Capillary Sorption Absorption Efficiency at a certain height z (CSAE z) expressed in %, which is the ratio of the values for CSAC 0 and CSAC z.

If two materials are combined (such as the first being used as acquisition/distribution material, and the second being used as liquid storage material), the CSAC value (and hence the respective CSAE value) of the second material can be determined for the CSDHxvalue of the first material.

Teabag Centrifuge Capacity Test (TCC Test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two litres of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately. After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately. The Teabag Centrifuge Capacity (TCC) for the sample of absorbent material is calculated as follows:

TCC=[(sample teabag weight after centrifuging)−(blank teabag weight after centrifuging)−(dry absorbent material weight)] ÷(dry absorbent material weight).

What is claimed is:

1. Liquid transport member comprising at least one bulk region and a wall region that completely circumscribes said bulk region, said wall region further comprising at least one inlet port region and at least one outlet port region, wherein said bulk region has an average fluid permeability $k_b$ which is higher than the average fluid permeability $k_p$ of the port regions and said port regions have a ratio of fluid permeability to thickness in the direction of fluid transport, $k_g/d_g$ of at least $3*10^{-15}$ m.

2. Liquid transport member according to claim 1, wherein said bulk region has a fluid permeability of at least $10^{-11}$ m$^2$.

3. Liquid transport member according to claim 1, wherein said port regions have a fluid permeability of at least $6*10^{-20}$ m$^2$.

4. Liquid transport member according to claim 1, wherein said port regions have a ratio of fluid permeability to thickness in the direction of fluid transport, $k_p/d_p$ of at least $7*10^{-14}$ m.

5. A liquid transport member according to claim 1, wherein the member further comprises an additional element in contact with said wall region.

6. A liquid transport member according to claim 5, wherein said additional element is in contact with the wall region and extends into said at least one bulk region, and has a capillary pressure for absorbing the liquid that is lower than the bubble point pressure of said member.

7. A liquid transport mtnember according to claim 5, wherein said additional element comprises a softness layer.

8. Liquid transport member according to claim 1, wherein the ratio of permeability of the bulk region and the permeability of the port region is at least 10.

9. Liquid transport member according to claim 1, wherein the member has a bubble point pressure when measured with water having a surface tension of 72 mN/m of at least 1 kPa.

10. Liquid transport member according to claim 1, wherein said port region has a bubble point pressure when measured with water having a surface tension of 72 mN/m of at least 1 kPa.

11. Liquid transport member according to claim 1, wherein said port region has a bubble point pressure when measured with an aqueous test solution having a surface tension of 33 mN/m of at least 0.67 kPa.

12. Liquid transport member according to claim 1, wherein each of said at least one bulk region and said port regions comprise pores.

13. Liquid transport member according to claim 12, wherein said bulk region has a larger average pore size than said port regions, preferably such that the ratio of average pore size of the bulk region and the average pore size of the port region is at least 3.

14. Liquid transport member according to claim 12, wherein said bulk region has an average pore size of at least 200 μm.

15. Liquid transport member according to claim 12, wherein said bulk region has a porosity of at least 50.

16. A Liquid transport member according to claim 12, wherein said port regions have a porosity of at least 10.

17. Liquid transport member according to claim 12, wherein said port regions have an average pore size of no more than 100 μm.

18. Liquid transport member according to claim 12, wherein said port regions have a pore size of at least 1 μm.

19. Liquid transport member according to claim 1, wherein said port regions have an average thickness of no more than 100 μm.

20. Liquid transport member according to claim 1, wherein said bulk region to said wall region have a volume ratio of at least 10.

21. Liquid transport member according to claim 1, wherein said port region is hydrophilic.

22. Liquid transport member according to claim 1, wherein the port regions do not substantially decrease the liquid surface tension of the liquid that is to be transported.

23. Liquid transport member according to claim 1, wherein said port region is oleophilic.

24. Liquid transport member according to claim 1, wherein said bulk region is deformable and expandable during liquid transport.

25. Liquid transport member according to claim 1, wherein said member is expandable upon contact and collapsible upon liquid removal bulk region.

26. A liquid transport member according to claim 25, wherein said member has a volume expansion factor of at least 5 between the original state and when fully immersed in liquid.

27. Liquid transport member according to claim 1 wherein said member is shaped either as a sheet or a cylinder.

28. Liquid transport member according to claim 1, wherein the cross-section area of the member along the direction of liquid transport is not constant.

29. Liquid transport member according to claim 28, wherein the port regions have a larger area than the average cross-section of the member along the direction of liquid transport.

30. Liquid transport member according to claim 1, wherein said bulk region comprises a material in a form selected from the groups of fibers, particulates, foams, spirals, films, corrugated sheets, or tubes.

31. Liquid transport member according to claim 1, wherein said wall region comprises a material in a form selected from the groups of fibers, particulates, foams, spirals, films, corrugated sheets, tubes, woven webs, woven fiber meshes, apertured films, or monolithic films.

32. Liquid transport member according to claim 30, wherein said foam is a open cell reticulated foam.

33. Liquid transport member according to claim 30, wherein said fibers are made of polyolefins, polyesters, polyamids, polyethers, polyacrylics, polyurethanes, metal, glass, cellulose, cellulose derivatives.

34. Liquid transport member according to claim 1 wherein the member is made by a porous bulk region that is wrapped by a separate wall region.

35. Liquid transport member according to claim 1 comprising water soluble materials.

36. Liquid transport member according to claim 35, wherein at least one of the port regions comprises a water soluble material.

37. Liquid transport member according to claim 1 for transport of water-based liquids or of viscoelastic liquids.

38. Liquid transport member according to claim 37 for transport of bodily discharges, as urine, blood menses, sweat or feces.

39. Liquid transport mnember according to claim 1 for transport of oil, grease, or other non-water based liquids.

40. Liquid transport member according to claim 39 for selective transport of oil or grease, but not water based liquids.

41. Liquid transport member according to claim 1, wherein any of the member properties or parameter are established prior to or at the liquid handling.

42. A liquid transport system comprising a liquid transport member according to any of the preceding claims and a source of liquid that is outside the liquid transport member, or a sink of liquid that is outside the liquid transport member, or both a source of liquid and a sink of liquid that are outside the liquid transport member.

43. A liquid transport system according to claim 42 having an absorption capacity of at least 5 g/g when submitted to the Demand Absorbency Test.

44. Liquid transport system according to claim 42 comprising superabsorbent material or open celled foam made from a High Internal Phase Emulsion (HIPE).

45. An article comprising a liquid transport member according to claim 1.

46. An article according to claim 45 which is a baby or adult incontinence diaper, a feminine protection pad, a pantiliner, or a training pant.

47. An article according to claim 45 which is a grease absorber.

48. An article according to claim 45 which is a water transport member.

* * * * *

UNITED STATES PATENT AND TRADEMARK OFFICE
CERTIFICATE OF CORRECTION

PATENT NO.     : 6,811,842 B1
DATED          : November 2, 2004
INVENTOR(S)    : Ehrnsperger et al.

It is certified that error appears in the above-identified patent and that said Letters Patent is hereby corrected as shown below:

Title page,
Item [86], PCT Filing Date, insert
-- PCT No.:     PCT/US98/13497,
   PCT Filed:   June 29, 1998 --.

Column 8,
Line 60, delete "flowerd" and insert -- lower --.

Column 9,
Line 9, delete "nvironmentally" and insert -- environmentally --.

Column 14,
Line 27, delete "extemally" and insert -- externally --.
Line 39, delete "mpermeable" and insert -- impermeable --.
Line 42, delete "articular" and insert -- particular --.

Column 16,
Line 52, delete "regionscan" and insert -- regions can --.

Column 17,
Line 32, delete "Afternatively" and insert -- Alternatively --.

Column 18,
Line 2, delete "ta" and insert -- to --.
Line 49, delete "weuting" and insert -- wetting --.

Column 28,
Line 2, delete "imechanically" and insert -- mechanically --.

Column 32,
Line 64, delete "mcans" and insert -- means --.

Column 33,
Line 26, delete "mernber" and insert -- member --.
Line 27, delete "intcgrally" and insert -- integrally --.

Column 41,
Line 65, delete "FedeCfabrik" and insert -- Federnfabrik --.
Line 68, delete "Fiatren" and insert -- Filtren --.

UNITED STATES PATENT AND TRADEMARK OFFICE
CERTIFICATE OF CORRECTION

PATENT NO. : 6,811,842 B1
DATED : November 2, 2004
INVENTOR(S) : Ehrnsperger et al.

It is certified that error appears in the above-identified patent and that said Letters Patent is hereby corrected as shown below:

Column 42,
Line 2, delete "Buopren" and insert -- Bulpren --.
Line 3, delete "BuGpren" and insert -- Bulpren --.

Column 43,
Line 23, delete "wail" and insert -- wall --.

Column 46,
Line 35, delete "destined" and insert -- distilled --.

Column 47,
Line 10, delete "destined" and insert -- distilled --.

Column 52,
Line 36, delete "and.so" and insert -- and so --.

Column 66,
Line 28, delete "mtnember" and insert -- member --.

Column 68,
Line 14, delete "mnember" and insert -- member --.

Signed and Sealed this

Eighteenth Day of October, 2005

JON W. DUDAS
*Director of the United States Patent and Trademark Office*